US012758243B2

(12) United States Patent
Choi

(10) Patent No.: US 12,758,243 B2
(45) Date of Patent: Oct. 13, 2026

(54) SURGICAL INSTRUMENT

(71) Applicant: LIVSMED INC., Seongnam-si (KR)

(72) Inventor: Woo Jung Choi, Siheung-si (KR)

(73) Assignee: LIVSMED INC., Seongnam-si (KR)

( * ) Notice: Subject to any disclaimer, the term of this patent is extended or adjusted under 35 U.S.C. 154(b) by 44 days.

(21) Appl. No.: 18/938,534

(22) Filed: Nov. 6, 2024

(65) Prior Publication Data

US 2025/0169839 A1 May 29, 2025

(30) Foreign Application Priority Data

Nov. 24, 2023 (KR) ........................ 10-2023-0166043

(51) Int. Cl.
*A61B 17/29* (2006.01)

(52) U.S. Cl.
CPC ...... *A61B 17/29* (2013.01); *A61B 2017/2912* (2013.01); *A61B 2017/2938* (2013.01)

(58) Field of Classification Search
CPC ... A61B 17/29; A61B 17/1155; A61B 17/105; A61B 17/072; A61B 17/068
USPC ...................................................... 227/175.1
See application file for complete search history.

(56) References Cited

U.S. PATENT DOCUMENTS 9,492,146 B2 * 11/2016 Kostrzewski .......... A61B 17/29

* cited by examiner

*Primary Examiner* — Nathaniel C Chukwurah
(74) *Attorney, Agent, or Firm* — Bridgeway IP Law Group, PLLC; Sang Ho Lee; Hyun Woo Shin

(57) ABSTRACT

Provided is a surgical instrument. The surgical instrument includes an end tool configured to rotate in at least one direction, and a manipulation part configured to control a motion of the end tool, wherein the end tool includes a pair of jaws including a first jaw and a second jaw, a working member configured to move in a lengthwise direction of the pair of jaws, a moving member formed to extend to have a length corresponding to a movement direction of the working member, and configured to transmit, to the working member, power for moving the working member, while linearly moving in a lengthwise direction, and a clutch assembly arranged in the working member and configured to allow or block transmission of power from the moving member to the working member.

21 Claims, 49 Drawing Sheets

(a)

(b)

(c)

(a)

(b)

SURGICAL INSTRUMENT

CROSS-REFERENCE TO RELATED APPLICATION

This application is based on and claims priority under 35 U.S.C. § 119 to Korean Patent Application No. 10-2023-0166043, filed on Nov. 24, 2023, in the Korean Intellectual Property Office, the disclosure of which is incorporated by reference herein in its entirety.

BACKGROUND

1. Field

The present disclosure relates to a surgical instrument, and more particularly, to a surgical instrument that is mountable on a robotic arm or manually operable for use in laparoscopic surgery or various other surgeries.

2. Description of the Related Art

In medical terms, surgery refers to the treatment of diseases by cutting, incising, or manipulating a skin, a mucous membrane, or other tissues by using medical devices. In particular, open surgery for incising and opening the skin of a surgical site to treat, shape, or remove an organ or the like therein causes issues such as bleeding, side effects, patient's pain, or scarring. Therefore, recently, surgery performed by forming a certain hole on a skin and inserting only a medical device, for example, a laparoscopic instrument or a surgical instrument, or surgery using a robot has been spotlighted as an alternative.

Here, a surgical robot refers to a robot that has a function of replacing a surgical action performed by a surgeon. Advantageously, the surgical robot may operate more accurately and precisely as compared with a human and enable remote surgery.

Surgical robots that are currently being developed worldwide may include a bone surgical robot, a laparoscopic surgical robot, a stereotactic surgical robot, and the like. Here, the laparoscopic surgical robot is a robot that performs minimum invasive surgery by using a laparoscope and small surgical instruments.

Laparoscopic surgery is a cutting-edge surgery technique that involves perforating one or more small holes in the abdomen and inserting a laparoscope, which is an endoscope for looking inside the abdomen to perform the surgery, and is a field that is expected to advance in the future. Today's laparoscopes are mounted with computer chips and have been developed to the extent that magnified images, which are clearer than images seen with the naked eye, may be obtained, and when used with specially-designed laparoscopic surgical tools while looking at a monitor screen, any type of surgery is possible.

Moreover, laparoscopic surgery offers the same range of surgical procedures as open surgery, but with several advantages including fewer complications, the ability to initiate treatment shortly after the procedure, and the capability to maintain the patient's stamina and immune functions. As a result, laparoscopic surgery is becoming increasingly recognized as the standard surgery for treating colorectal cancer or the like in places such as the United States and Europe.

Meanwhile, a surgical robot is generally composed of a master robot and a slave robot. When a surgical operator manipulates a control lever (e.g., a handle) provided on the master robot, a surgical tool coupled to or held by a robotic arm on the slave robot is manipulated to perform surgery.

The above-mentioned background art is technical information possessed by the inventor for the derivation of the present disclosure or acquired during the derivation of the present disclosure, and cannot necessarily be said to be a known technique disclosed to the general public prior to the filing of the present disclosure.

SUMMARY

The present disclosure provides a surgical instrument capable of controlling a movement of a working member provided in the surgical instrument, in a one-way clutch manner.

In addition, the present disclosure provides a surgical instrument capable of simultaneously moving or relatively moving a working member and a moving member both provided in the surgical instrument.

However, the above objectives are examples, and the objectives of the present disclosure are not limited thereto.

Additional aspects will be set forth in part in the description which follows and, in part, will be apparent from the description, or may be learned by practice of the presented embodiments of the disclosure.

An aspect of the present disclosure provides a surgical instrument including an end tool configured to rotate in at least one direction, and a manipulation part configured to control a motion of the end tool, wherein the end tool includes a pair of jaws including a first jaw and a second jaw, a working member configured to move in a lengthwise direction of the pair of jaws, a moving member formed to extend to have a length corresponding to a movement direction of the working member, and configured to transmit, to the working member, power for moving the working member, while linearly moving in a lengthwise direction, and a clutch assembly arranged in the working member and configured to allow or block transmission of power from the moving member to the working member.

In addition, the second jaw may be rotatable with respect to the first jaw.

In addition, the working member may apply a force while moving in a direction from proximal ends of the pair of jaws toward distal ends of the pair of jaws, such that the first jaw and the second jaw perform a clamping motion.

In addition, the working member may include a body part, a first flange arranged on one side of the body part and formed to have a width greater than a width of the body part, and a second flange arranged on another side of the body part and formed to have a width greater than the width of the body part.

In addition, the first jaw may include a first slit extending in the lengthwise direction of the first jaw, and the working member may move while at least a portion of the body part is accommodated in the first slit.

In addition, the in the working member, the second flange may be arranged at a lower portion of the first jaw, the body part may be arranged to pass through the first slit from the first jaw, and at least a portion of the second flange may come into contact with the first jaw when the working member moves in the lengthwise direction of the pair of jaws.

In addition, the second jaw may include a second slit extending in the lengthwise direction of the second jaw, and the working member may move while at least a portion of the body part is accommodated in the second slit.

In addition, in the working member, the first flange may be arranged at an upper portion of the first jaw, the body part may be arranged to pass through the second slit from the second jaw, and at least a portion of the first flange may come into contact with the second jaw when the working member moves in the lengthwise direction of the pair of jaws.

In addition, the working member may further include a clutch room formed from one surface of the body part toward an inside of the body part, and the clutch assembly may be arranged in the clutch room.

In addition, the clutch assembly may include a clutch member formed to come into contact with the moving member, and when the moving member moves toward the distal ends of the pair of jaws, the clutch member and the moving member may come into close contact with each other such that the moving member and the working member move together.

In addition, in the clutch assembly, when the moving member moves toward proximal ends of the pair of jaws, the close contact between the clutch member and the moving member may be released such that the moving member moves with respect to the working member.

In addition, the clutch assembly may further include inclined portions that are formed to be inclined at least in part to have a shape that is farther from center of the clutch assembly toward the distal ends of the pair of jaws, and are formed to come into contact with the clutch member as the moving member moves.

In addition, in the clutch assembly, when the moving member moves toward the distal ends of the pair of jaws, the clutch member may also move in the same direction to come into contact with the inclined portions, and when the moving member moves toward the proximal ends of the pair of jaws, the clutch member may also move in the same direction such that a contact state between the clutch member and the inclined portions is released.

In addition, the clutch assembly may further include a first elastic member configured to apply a force to the clutch member in a direction corresponding to the movement direction of the working member.

In addition, the clutch member may have a circular cross-section.

In addition, the clutch assembly may further include a backward wire configured to transmit power for moving the working member toward the proximal ends of the pair of jaws, and the inclined portions may be formed to be deformed or moved at least in part based on a movement direction of the backward wire.

In addition, the clutch assembly may further include an internal space arranged between the inclined portions in a direction corresponding to the movement direction of the working member, a backward block arranged in the internal space, and a backward wire connected to the backward block to transmit power for moving the working member toward the proximal ends of the pair of jaws.

In addition, the backward block may be arranged between the inclined portions to prevent at least portions of the inclined portions from being deformed or moved toward each other by a force applied to the inclined portions.

In addition, when the backward block moves along the internal space toward the proximal ends of the pair of jaws, at least portions of the inclined portions may be deformed or moved toward each other.

In addition, the clutch assembly may further include a second elastic member arranged on a side of a proximal end of the backward block.

In addition, when the backward block moves toward the proximal ends of the pair of jaws, the working member may move with respect to the moving member.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
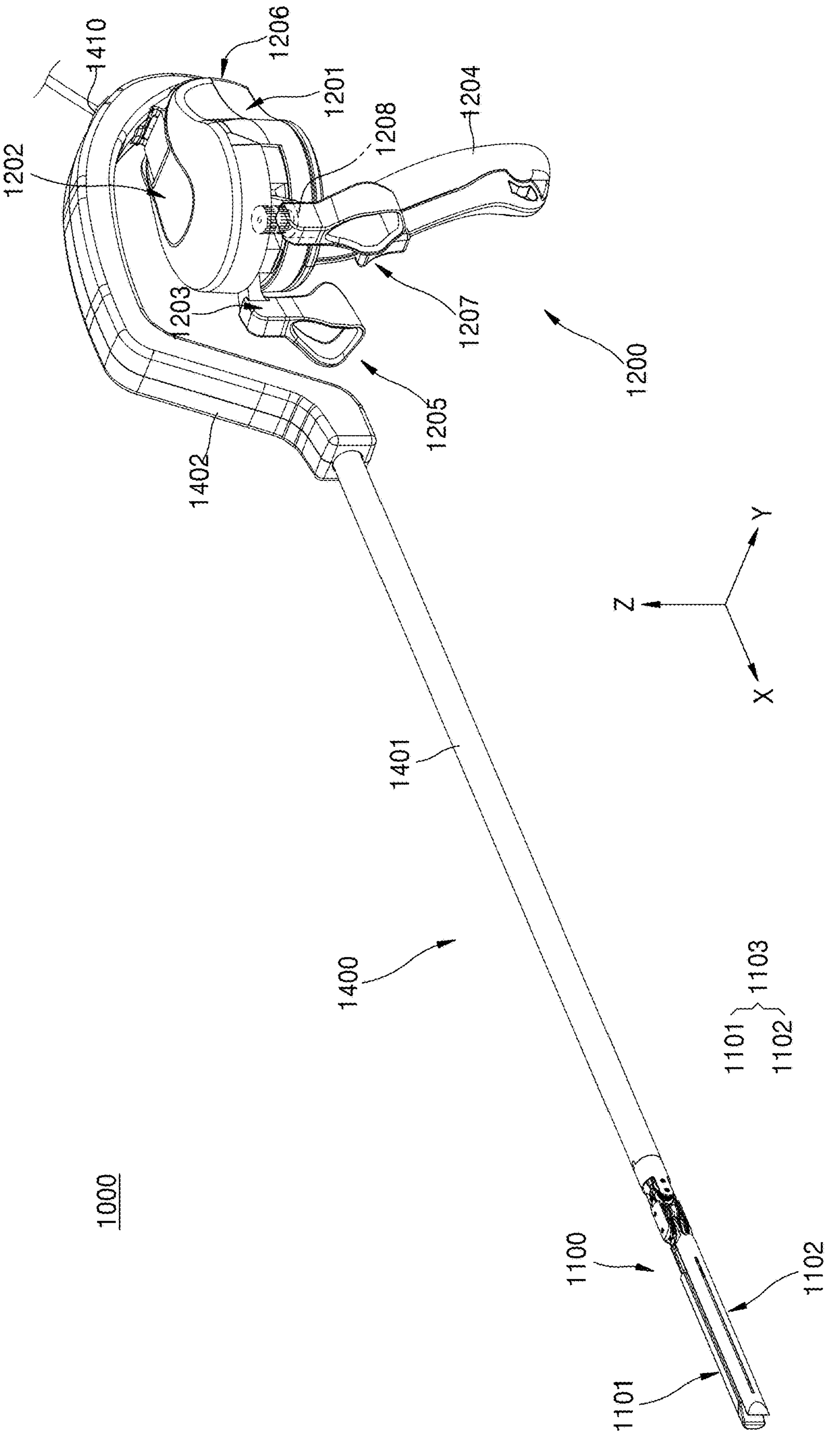
FIG. 1 is a perspective view illustrating a surgical instrument according to an embodiment of the present disclosure.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

As the present disclosure allows for various changes and numerous embodiments, particular embodiments will be illustrated in the drawings and described in detail. Advantages and features of the present disclosure and a method of achieving the same should become clear with embodiments described below in detail with reference to the drawings. However, the present disclosure is not limited to the embodiments disclosed below, but may be implemented in various forms.

Hereinafter, embodiments will be described in detail with reference to the accompanying drawings, and the same or corresponding components will be denoted by the same reference numerals when described with reference to the accompanying drawings, and thus, their descriptions that are already provided will be omitted.

In the following embodiments, terms such as "first," "second," etc., are used only to distinguish one component from another, and such components must not be limited by these terms.

In the following embodiments, the singular expression also includes the plural meaning as long as it is not inconsistent with the context.

In the following embodiments, the terms "comprises," "includes," "has", and the like used herein specify the presence of stated features or components, but do not preclude the presence or addition of one or more other features or components.

For convenience of description, the magnitude of components in the drawings may be exaggerated or reduced. For example, because the size and thickness of each component illustrated in the drawing are arbitrarily shown for convenience of description, the present disclosure is not necessarily limited to those illustrated in the drawing.

In the following embodiments, the x-axis, y-axis, and z-axis are not limited to three axes on a Cartesian coordinate system, and may be interpreted in a broad sense including them. For example, the x-axis, the y-axis, and the z-axis may be orthogonal to each other, but may refer to different directions that are not orthogonal to each other.

In a case in which a particular embodiment is realized otherwise, a particular process may be performed out of the order described. For example, two processes, which are successively described herein, may be substantially simultaneously performed, or may be performed in a process sequence opposite to a described process sequence.

Hereinafter, based on the above-described principles, a surgical instrument according to the present disclosure will be described in detail with reference to the drawings.

Figure 2:
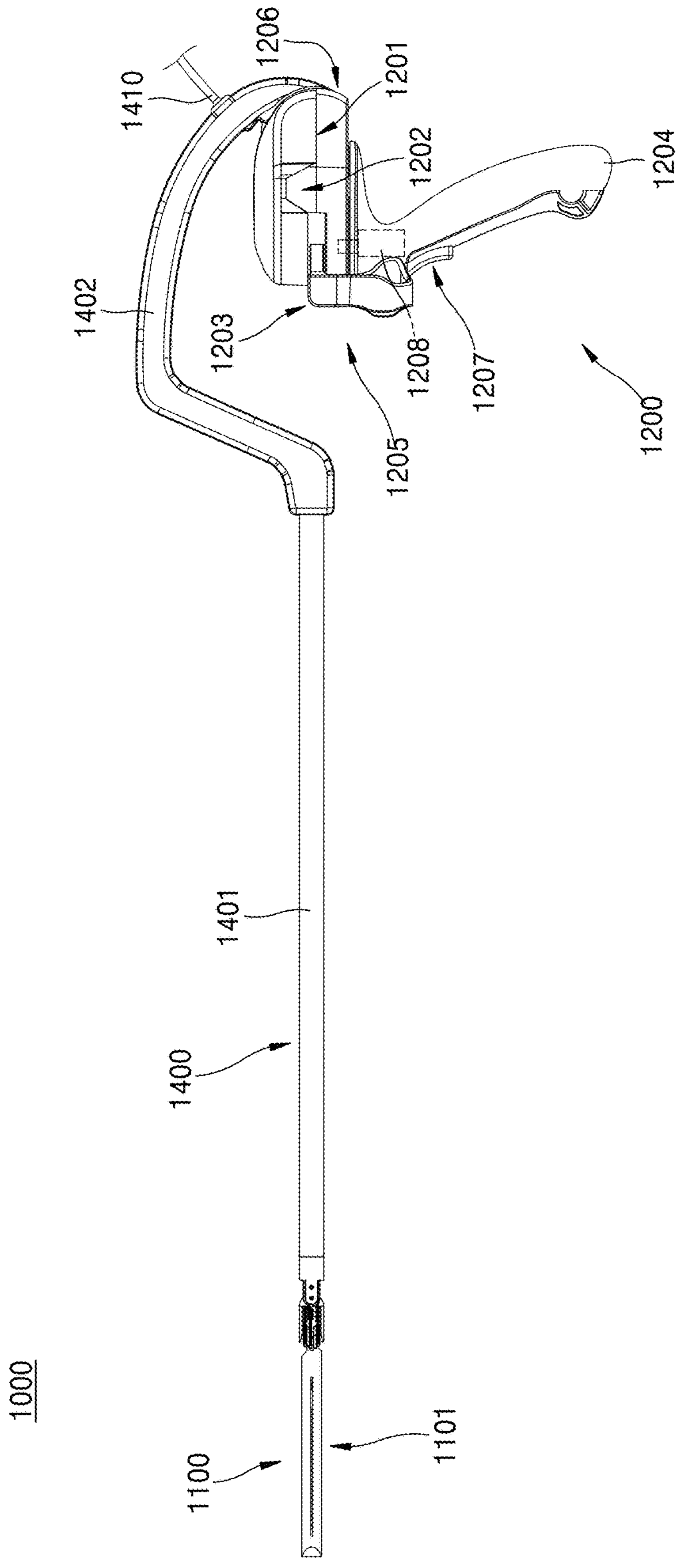
FIG. 2 is a side view of the surgical instrument of FIG. 1, viewed from the side.

FIG. 1 is a perspective view illustrating a surgical instrument according to an embodiment of the present disclosure, and FIG. 2 is a side view of the surgical instrument of FIG. 1, viewed from the side.

First, referring to FIGS. 1 and 2, a surgical instrument 1000 according to the present embodiment includes an end tool 1100, a manipulation part 1200, a power transmission part (not shown), and a connection part 1400.

Here, the connection part 1400 may be formed in the shape of a hollow shaft, to accommodate therein one or more wires and electric wires. As the manipulation part 1200 is coupled to one end of the connection part 1400, and the end tool 1100 is coupled to the other end, the connection part 1400 may serve to connect the manipulation part 1200 to the end tool 1100. The connection part 1400 has a straight portion 1401 formed on the side where the connection part 1400 is coupled to the end tool 1100, and a bent portion 1402 formed on the side where the connection part 1400 is coupled to the manipulation part 1200. As such, as the end of the connection part 1400 on the side of the manipulation part 1200 is formed to be bent, a pitch manipulation part 1201, a yaw manipulation part 1202, and an actuation manipulation part 1203 are formed along or adjacent to the extension line of the end tool 1100. In other words, it may also be described that the pitch manipulation part 1201 and the yaw manipulation part 1202 are at least partially accommodated in a concave portion formed by the bent portion 1402. Through the above-described shape of the bent portion 1402, the shapes and motions of the manipulation part 1200 and the end tool 1100 may match each other more intuitively.

Meanwhile, a plane on which the bent portion 1402 is formed may be a pitch plane, that is, a plane substantially the same as an XZ plane of FIG. 1. As such, as the bent portion 1402 is formed on a plane substantially the same as the XZ plane, interference with the manipulation part may be reduced. Obviously, for intuitive motions of the end tool and the manipulation part, any form other than the XZ plane may be possible.

Meanwhile, a connector 1410 may be formed on the bent portion 1402. The connector 1410 may be connected to an external power source (not shown), and the connector 1410 may also be connected to the end tool 1100 via an electric wire, and thus may transmit, to the end tool 1100, electric energy supplied from the external power source (not shown). In addition, the electric energy transmitted to the end tool 1100 as described above may be used to generate a driving force for rotating a staple pulley (see 1161 of FIG. 6), which will be described below, clockwise or counterclockwise. In addition, the electric energy may also be supplied to drive a driving part 1208. Obviously, a built-in battery may be used.

The manipulation part 1200 may be formed at one end of the connection part 1400 and may include an interface which may be directly manipulated by a doctor, for example, an interface in the shape of a pincer, a stick, a lever, etc. When the doctor manipulates the interface, the end tool 1100, which is connected to the interface and inserted into the body of a patient, operates in a certain manner to perform surgery. Here, although FIG. 1 illustrates that the manipulation part 1200 is formed in the shape of a handle that may be rotated while fingers are inserted therein, the present disclosure is not limited thereto, and various types of manipulation parts that may be connected to the end tool 1100 to manipulate the end tool 1100 may be possible.

The end tool 1100 may be formed at the other end of the connection part 1400 and may be inserted into a surgical site to perform a motion necessary for surgery. As an example of the end tool 1100 as described above, a pair of jaws 1103 for performing a grip motion as illustrated in FIG. 1 may be used. However, the present disclosure is not limited thereto, and various other surgical instruments may be used as the end tool 1100. For example, a one-armed cautery may be used as the end tool. As the end tool 1100 is connected to the manipulation part 1200 by the power transmission part (not shown), the end tool 1100 may receive a driving force of the manipulation part 1200 through the power transmission part (not shown) to perform motions required for a surgery, such as a grip motion, a cutting motion, or a suturing motion.

Here, the end tool 1100 of the surgical instrument 1000 according to a first embodiment of the present disclosure is formed to be rotatable in at least one direction, and for example, the end tool 1100 may be formed to perform a pitch motion around the Y-axis of FIG. 1 and simultaneously perform a yaw motion and an actuation motion around the Z-axis of FIG. 1.

Here, the pitch, yaw, and actuation motions used in the present disclosure are defined as follows.

First, the pitch motion refers to a motion of the end tool 1100 rotating in a vertical direction with respect to an extension direction of the connection part 1400 (the X-axis direction of FIG. 1), that is, a motion of rotating around the Y-axis of FIG. 1. In other words, the pitch motion refers to a motion in which the end tool 1100 extending from the connection part 1400 in the extension direction of the connection part 1400 (the X-axis direction of FIG. 1) rotates up and down around the Y-axis with respect to the connection part 1400.

Next, the yaw motion refers to a motion of the end tool 1100 rotating in a horizontal direction with respect to the extension direction of the connection part 1400 (the X-axis direction of FIG. 1), that is, a motion of rotating around the Z-axis of FIG. 1. In other words, the yaw motion refers to a motion in which the end tool 1100 extending from the connection part 1400 in the extension direction of the connection part 1400 (the X-axis direction of FIG. 1) rotates left and right around the Z-axis with respect to the connection part 1400. That is, the yaw motion refers to a motion of the two jaws 101 and 102, which are formed on the end tool 1100, rotating around the Z-axis in the same direction.

In addition, the actuation motion refers to a motion of the end tool 1100 rotating around the same rotation axis as in the yaw motion, but with the two jaws 1103 rotating in the opposite directions to be closed or opened. That is, the actuation motion refers to a motion of the two jaws 1103, which are formed on the end tool 1100, rotating around the Z-axis in the opposite directions.

The power transmission part (not shown) may serve to connect the manipulation part 1200 to the end tool 1100 to transmit the driving force of the manipulation part 1200 to the end tool 1100, and may include a plurality of wires, pulleys, links, joints, gears, and the like.

The end tool 1100, the manipulation part 1200, and the like of the surgical instrument 1000 of FIG. 1 will be described in detail below.

(Intuitive Operation)

Hereinafter, an intuitive operation of the surgical instrument 1000 of the present disclosure will be described.

First, a user may perform a pitch motion by rotating a handle 1204 around the X-axis while holding the handle 1204 with the palm of his or her hand, and may perform a yaw motion by rotating the handle 1204 around the Z-axis. In addition, the user may perform the actuation motion by manipulating the actuation manipulation part 1203 while inserting his or her thumb and index finger into an extending portion formed in the shape of a hand ring at one end of the actuation manipulation part 1203.

Here, in the surgical instrument 1000 according to the first embodiment of the present disclosure, when the manipulation part 1200 is rotated in any one direction with respect to the connection part 1400, the end tool 1100 rotates in the intuitively same direction as the manipulation direction of the manipulation part 1200. In other words, when the handle 1204 of the manipulation part 1200 is rotated in any one direction, the end tool 1100 also rotates in the intuitively same direction as the one direction, to perform a pitch motion or a yaw motion. Here, "the intuitively same direction" may indicate that the movement direction of a finger of the user holding the manipulation part 1200 is substantially the same as the movement direction of the distal end of the end tool 1100. Obviously, "the same direction" as used herein may not be a perfectly matching direction on a three-dimensional coordinate, and may be understood to be equivalent to the extent that, for example, when the user's finger moves to the left, the distal end of the end tool 1100 moves to the left, and when the user's finger moves downward, the end portion of the end tool 1100 moves downward.

In addition, to this end, in the surgical instrument 1000 according to the present embodiment, the manipulation part 1200 and the end tool 1100 are formed in the same direction with respect to a plane perpendicular to the extension axis (the X-axis) of the connection part 1400. That is, when viewed with respect to the YZ plane of FIG. 1, the manipulation part 1200 is formed to extend in the positive (+) X-axis direction, and the end tool 1100 is also formed to extend in the positive (+) X-axis direction. In other words, it may also be described that the formation direction of the end tool 1100 on one end of the connection part 1400 is the same as the formation direction of the manipulation part 1200 on the other end of the connection part 1400, with respect to the YZ plane. Alternatively, in other words, it may also be described that the manipulation part 1200 is formed in a direction proceeding away from the body of the user holding the manipulation part 1200, that is, in the direction in which the end tool 1100 is formed. That is, in the first handle 1204 or the like that is held and moved by the user for an actuation motion, a yaw motion, and a pitch motion, a part that moves to perform each motion extends in the positive (+) X-axis direction beyond the center of rotation of each joint for the motion. Through this, the manipulation part 1200 may be configured in the same manner as the end tool 1100 in which each moving part is formed to extend in the positive (+) X-axis direction from the center of rotation of a corresponding joint for the motion, the manipulation direction of the user may match the motion direction of the end tool from the viewpoint of the rotation directions and the left and right directions, and accordingly, intuitively the same manipulation may be possible.

In detail, in a related-art surgical instrument, a direction in which a user manipulates the manipulation part is different from a direction in which the end tool is actually operated, that is, intuitively different from the direction in which the end tool is actually operated, and thus, a surgical operator may not easily intuitively manipulate the surgical instrument and may spend a long time to learn a skill of operating the end tool in desired directions, and in some cases, malfunctions may occur, which may cause damage to a patient.

To overcome such an issue, in the surgical instrument 1000 according to the first embodiment of the present disclosure, the manipulation direction of the manipulation part 1200 may be intuitively identical to the operation direction of the end tool 1100, and to this end, a portion of the manipulation part 1200 that actually moves for an actuation motion, a yaw motion, and a pitch motion may extend in the positive (+) X-axis direction beyond the center of rotation of a joint for each motion as in the end tool 1100.

Hereinafter, the end tool 1100, the manipulation part 1200, and the like of the surgical instrument 1000 of FIG. 1 will be described in more detail.

(End Tool)

Hereinafter, the end tool 1100 of the surgical instrument 1000 will be described in more detail.

Figure 3:
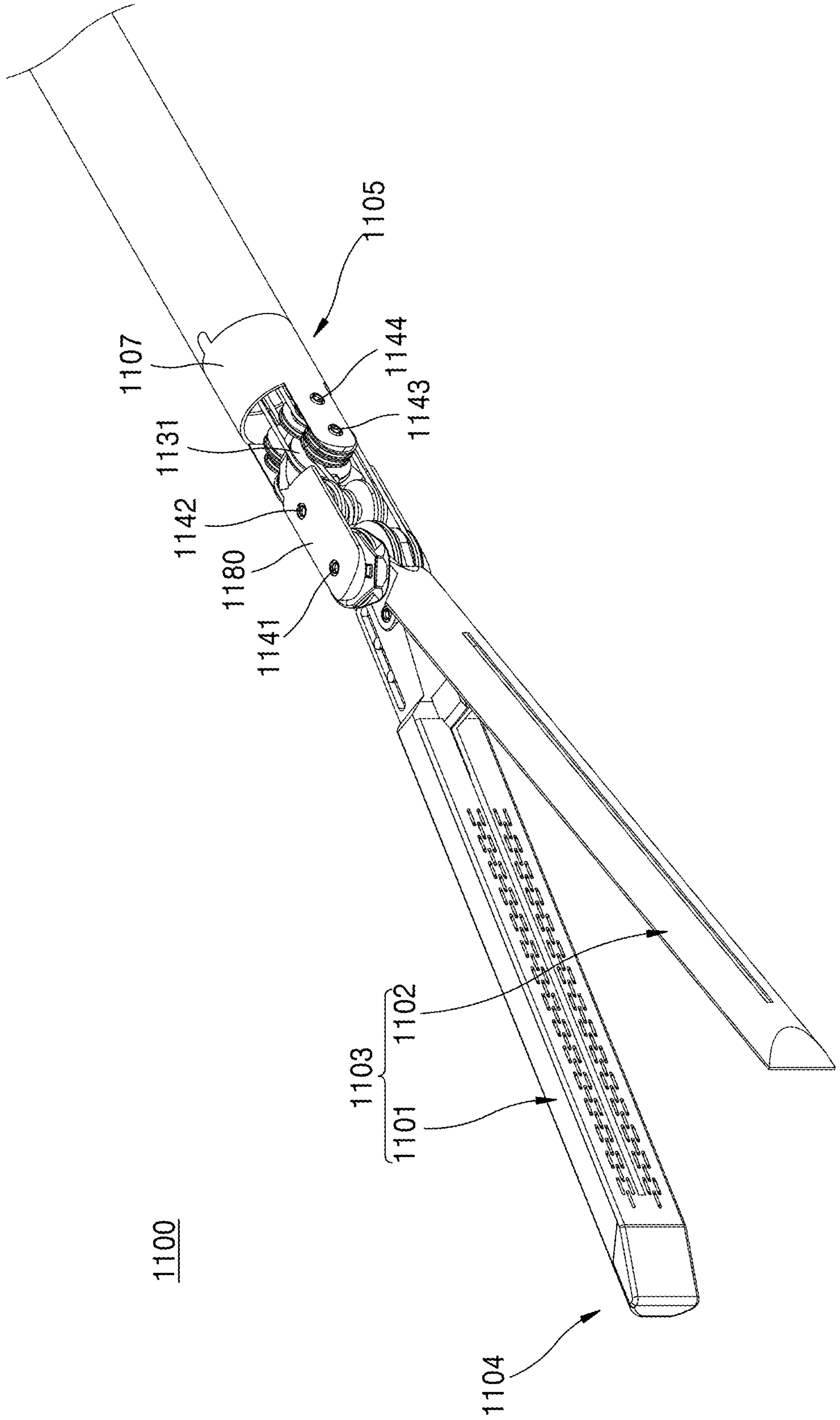
FIG. 3 is a perspective view illustrating an end tool of the surgical instrument of FIG. 1.
Figure 4:
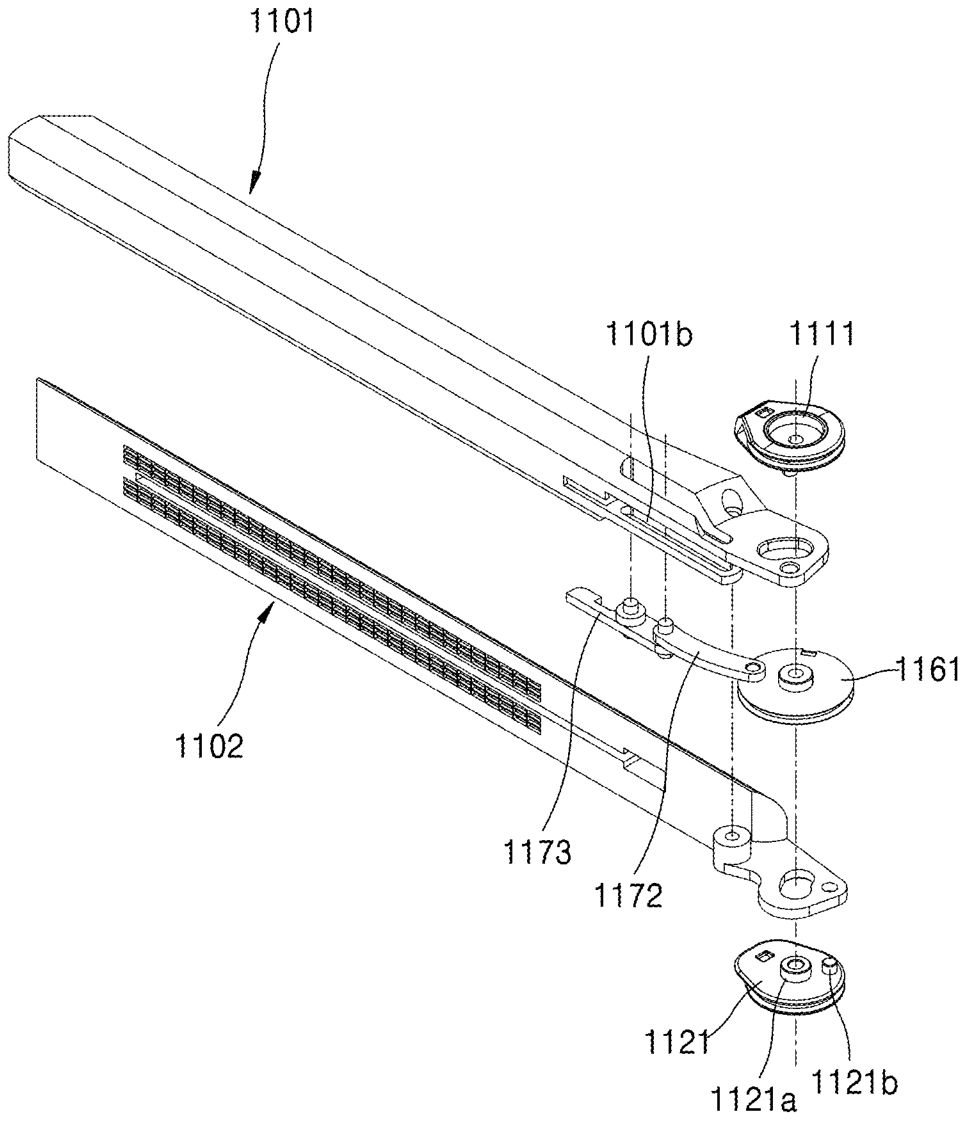
FIGS. 4 and 5 are exploded perspective views of the end tool of the surgical instrument of FIG. 3.
Figure 5:
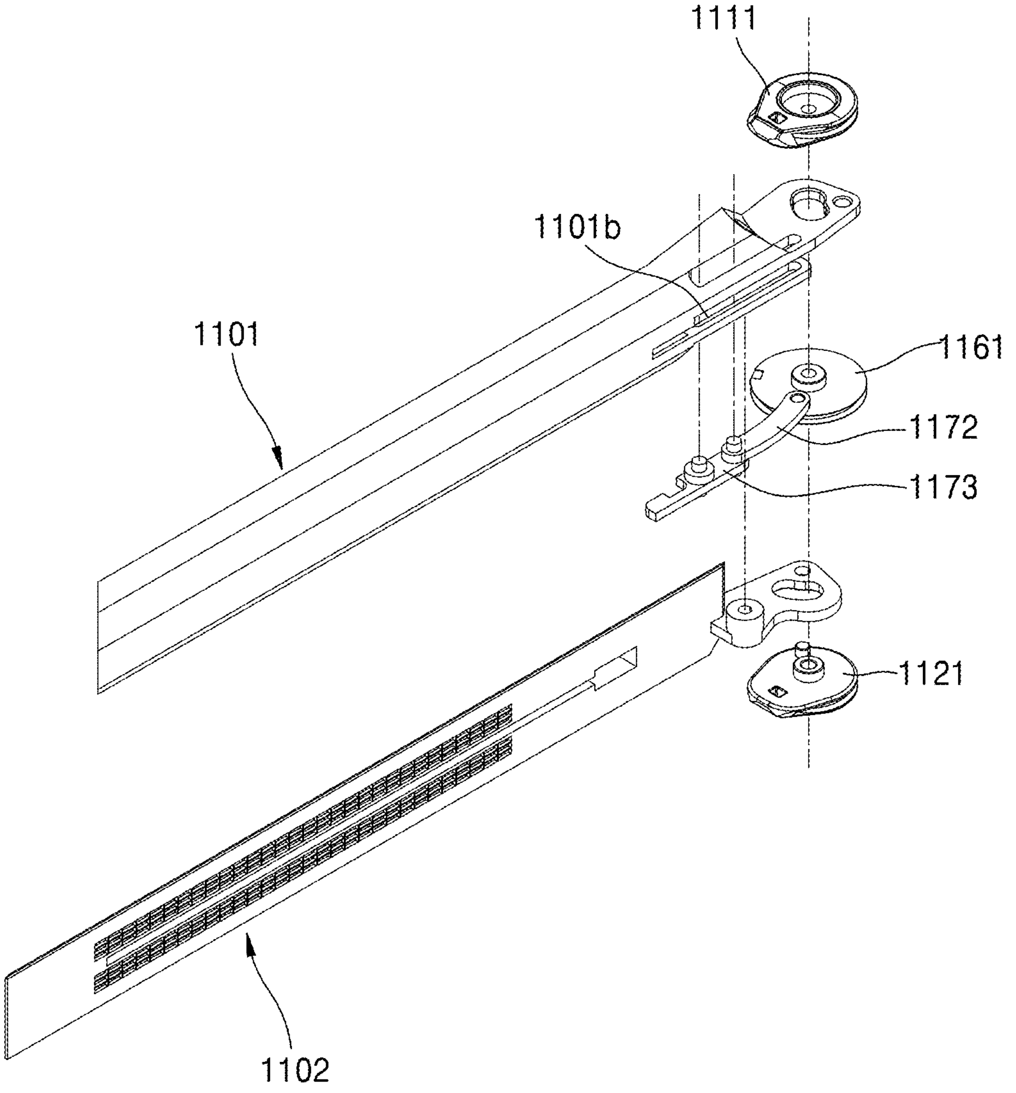

FIG. 3 is a perspective view illustrating the end tool of the surgical instrument of FIG. 1, and FIGS. 4 and 5 are exploded perspective views of the end tool of the surgical instrument of FIG. 3.

The end tool 1100 for a surgical instrument according to an embodiment of the present disclosure includes a pair of jaws for performing a grip motion, that is, a first jaw 1101 and a second jaw 1102. Here, a component encompassing each of the first jaw 1101 and the second jaw 1102 or both the first jaw 1101 and the second jaw 1102 may be referred to as jaws 1103.

In addition, the end tool 1100 may include a plurality of pulleys including a pulley 1111 associated with a rotational motion of the first jaw 1101. In addition, the end tool 1100 may include a plurality of pulleys including a pulley 1121 associated with a rotational motion of the second jaw 1102.

Here, although the drawings illustrate that the pulleys facing each other are arranged in parallel to each other, the present disclosure is not limited thereto, and the pulleys may be formed in various positions and sizes suitable for the configuration of the end tool.

In addition, the end tool 1100 of the present embodiment may include an end tool hub 1180 and a pitch hub 1107.

A rotation shaft 1141 and a rotation shaft 1142 may be inserted through the end tool hub 1180, and the end tool hub 1180 may accommodate therein at least portions of one or more pulleys that are axially coupled to the rotation shaft 1141. In addition, the end tool hub 1180 may accommodate therein at least portions of one or more pulleys that are axially coupled to the rotation shaft 1142.

In addition, at least portions of a staple pulley assembly (see 1160 of FIG. 6) and a staple link assembly (see 1170 of FIG. 6), which will be described below, may be formed on one side of the end tool hub 1180, for example, in a space adjacent to the center.

In addition, a pulley 1131 serving as an end tool pitch pulley may be formed at one end of the end tool hub 1180. The pulley 1131 may be formed as one body with the end tool hub 1180. That is, a disk-shaped pulley may be formed at one end of the end tool hub 1180, and a groove around which a wire may be wound may be formed on an outer circumferential surface of the end tool hub 1180. Alternatively, the pulley 1131 may be formed as a separate member from the end tool hub 1180 and then coupled to the end tool hub 1180.

A rotation shaft 1143 and a rotation shaft 1144 may be inserted through the pitch hub 1107, and the pitch hub 1107 may be axially coupled to the end tool hub 1180 (and the pulley 1131) by the rotation shaft 1143. Thus, the end tool hub 1180 and the pulley 1131 may be formed to be rotatable around the rotation shaft 1143 with respect to the pitch hub 1107.

In addition, the pitch hub 1107 may accommodate therein at least portions of one or more pulleys that are axially coupled to the rotation shaft 1143. In addition, the pitch hub 1107 may accommodate therein at least portions of one or more pulleys that are axially coupled to the rotation shaft 1144.

In addition, the end tool 1100 of the present embodiment may include the rotation shaft 1141, the rotation shaft 1142, the rotation shaft 1143, and the rotation shaft 1144. As described above, the rotation shaft 1141 and the rotation shaft 1142 may be inserted through the end tool hub 1180, and the rotation shaft 1143 and the rotation shaft 1144 may be inserted through the pitch hub 1107.

The rotation shaft 1141, the rotation shaft 1142, the rotation shaft 1143, and the rotation shaft 1144 may be arranged sequentially from a distal end 1104 of the end tool 1100 toward a proximal end 1105. Accordingly, starting from the distal end 1104, the rotation shaft 1141 may be referred to as a first pin, the rotation shaft 1142 may be referred to as a second pin, the rotation shaft 1143 may be referred to as a third pin, and the rotation shaft 1144 may be referred to as a fourth pin.

Here, the rotation shaft 1141 may function as an end tool jaw pulley rotation shaft, the rotation shaft 1142 may function as an end tool jaw auxiliary pulley rotation shaft, the rotation shaft 1143 may function as an end tool pitch rotation shaft, and the rotation shaft 1144 may function as an end tool pitch auxiliary rotation shaft of the end tool 1100.

One or more pulleys may be fit into each of the rotation shafts 1141, 1142, 1143, and 1144.

In addition, a rotation shaft may be further formed on one side of the rotation shaft 1141, specifically, on the side of the distal end 1104 of the rotation shaft 1141.

The pulley 1111 functions as an end tool first jaw pulley, and the pulley 1121 functions as an end tool second jaw pulley. The pulley 1111 may be referred to as a first jaw pulley, the pulley 1121 may be referred to as a second jaw pulley, and these two components may be collectively referred to as end tool jaw pulleys or simply as jaw pulleys.

The pulley 1111 and the pulley 1121, which are end tool jaw pulleys, are formed to face each other, and are formed to be rotatable independently of each other around the rotation shaft 1141, which is an end tool jaw pulley rotation shaft. Here, the pulley 1111 and the pulley 1121 may be formed to be spaced apart from each other to a certain extent, and a staple assembly accommodation part may be formed therebetween. In addition, at least portions of a staple pulley assembly 1160 and a staple link assembly 1170, which will be described below, may be arranged in the staple assembly accommodation part.

Here, the drawings illustrate that the pulley 1111 and the pulley 1121 are formed to rotate around one rotation shaft 1141, but it is needless to say that each end tool jaw pulley may be formed to be rotatable around a separate shaft. Here, the first jaw 1101 may be fixedly coupled to the pulley 1111 to rotate together with the pulley 1111, and the second jaw 1102 may be fixedly coupled to the pulley 1121 to rotate together with the pulley 1121. A yaw motion and an actuation motion of the end tool 1100 are performed according to rotation of the pulley 1111 and the pulley 1121. That is, when the pulley 1111 and the pulley 1121 rotate in the same direction around the rotation shaft 1141, the yaw motion is performed, and when the pulley 1111 and the pulley 1121 rotate in opposite directions around the rotation shaft 1141, the actuation motion is performed.

Here, the first jaw 1101 and the pulley 1111 may be formed as separate members and then coupled to each other, or the first jaw 1101 and the pulley 1111 may be formed as one body. Similarly, the second jaw 1102 and the pulley 1121 may be formed as separate members and then coupled to each other, or the second jaw 1102 and the pulley 1121 may be formed as one body.

In addition, one or more auxiliary pulleys may be arranged adjacent to the pulley 1111 and the pulley 1121.

These pulleys may be formed such that one or more wires are wound therearound, the pulleys may be rotated by the wires, and the wires may move along the pulleys to transmit power to the end tool 1100.

(Components Associated with Staple Pulley)

Hereinafter, a staple driving assembly of the end tool 1100 of the surgical instrument of FIG. 1 will be described in more detail.

Figure 6:
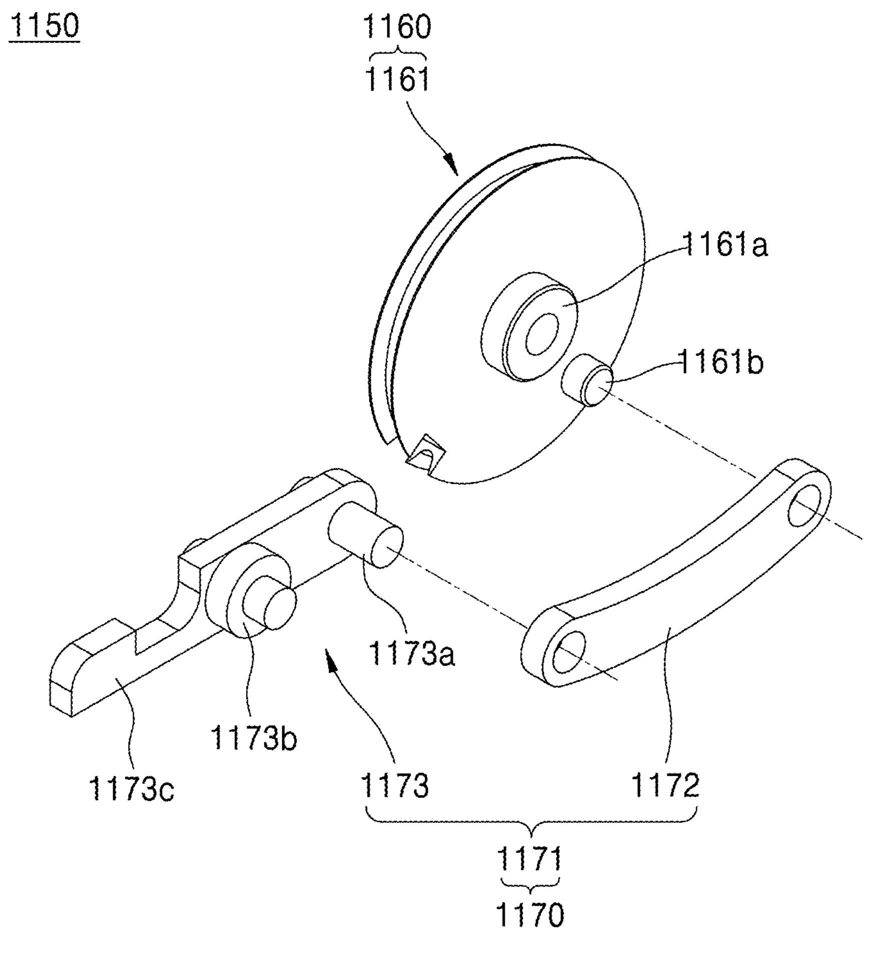
FIG. 6 is an exploded perspective view illustrating an embodiment of a staple driving assembly of the surgical instrument of FIG. 3.

FIG. 6 is an exploded perspective view illustrating an embodiment of a staple driving assembly of the surgical instrument of FIG. 3.

The end tool 1100 of the present embodiment may include one or more pulleys including a staple pulley 1161 associated with linear/rotational motions of each pulley and link for stapling and cutting.

The staple pulley 1161 is formed to face the pulley 1111 and the pulley 1121, which are end tool jaw pulleys, and is formed to be rotatable independently around the rotation shaft 1141, which is an end tool jaw pulley rotation shaft. Here, although the drawings illustrate that the staple pulley 1161 is arranged between the pulley 1111 and the pulley 1121, the present disclosure is not limited thereto, and the staple pulley 1161 may be arranged at various positions adjacent to the pulley 1111 or the pulley 1121.

Here, in the present disclosure, the staple pulley 1161, the pulley 1111, and the pulley 1121 are formed to rotate around substantially the same shaft. As the staple pulley 1161, the pulley 1111, and the pulley 1121 are formed to rotate around the same shaft as described above, it is possible to perform a pitch motion/yaw motion/actuation motion as well as stapling and cutting motions.

The drawings illustrate that the staple pulley 1161, the pulley 1111, and the pulley 1121 are formed to rotate around one rotation shaft 1141, but it is needless to say that the jaw pulleys may be formed to be rotatable around separate concentric shafts, respectively.

In other words, it may also be described as a structure in which the pulley 1111, which is a first jaw pulley, the staple pulley 1161, and the pulley 1121, which is a second jaw pulley, are sequentially stacked along the rotation shaft 1141. Alternatively, it may also be described as a structure in which the staple pulley 1161 is arranged between the pulley 1111 and the pulley 1121 facing each other. Here, the pulley 1111, which is a first jaw pulley, the staple pulley 1161, and the second jaw pulley 1121 may be formed to be rotatable independently of each other.

One or more staple auxiliary pulleys (not shown) may be additionally provided on one side of the staple pulley 1161.

In addition, one or more pulleys (not shown) may function as staple pitch main pulleys, and one or more other pulleys may function as staple pitch sub-pulleys.

When one or more wires are pulled and released by the driving part 1208 of FIG. 1, the staple pulley 1161 coupled to the wires may rotate in one direction, and accordingly, stapling may be performed.

In addition, in an alternative embodiment, as one or more staple auxiliary pulleys (not shown) are arranged, the radius of rotation of the staple pulley 1161 increases, enabling the effect of widening the range of a yaw motion in which normal stapling and cutting motions may be performed.

(Staple Driving Assembly)

Hereinafter, a staple driving assembly 1150 will be described in more detail.

Referring to FIG. 6 and the like, the staple driving assembly 1150 may include the staple pulley assembly 1160 and the staple link assembly 1170. Here, the staple driving assembly 1150 is connected to a moving member 1550 of a cartridge 1500 to be described below, to convert a rotational motion of the staple pulley 1161 into a linear motion of the moving member 1550. In other embodiments of the present disclosure to be described below, the staple drive assembly may be understood as including the staple pulley assembly and the staple link assembly. A driving force is transmitted to the staple driving assembly 1150 through the driving part 1208, and the moving member 1550 and a working member 1540 connected thereto is moved by a motion of the staple driving assembly 1150.

The staple pulley assembly 1160 may include one or more staple pulleys 1161. The staple pulley assembly 1160 may be formed between the pulley 1111 and the pulley 1121, to be adjacent to the pulley 1111 and the pulley 1121. In the present embodiment, it is assumed that the staple pulley assembly 1160 includes one staple pulley 1161.

A shaft pass-through part 1161*a* may be formed in the staple pulley 1161. The shaft pass-through part 1161*a* may be formed in the form of a hole, and the rotation shaft 1141, which is an end tool jaw pulley rotation shaft, may be inserted through the shaft pass-through part 1161*a*. In addition, a link coupling part 1161*b* may be formed on the staple pulley 1161. The staple link assembly 1170 to be described below may be coupled to the link coupling part 1161*b*. This will be described in more detail below.

In addition, the end tool 1100 of the present embodiment may further include the staple link assembly 1170 connected to the staple pulley assembly 1160. The staple link assembly 1170 may include one or more link members 1171. The staple link assembly 1170 may serve to connect the staple pulley assembly 1160 to the moving member 1550 of the cartridge 1500, which will be described below. In the present embodiment, it is assumed that the staple link assembly 1170 includes one link member 1171, and the link member 1171 includes a first link 1172 and a second link 1173.

The first link 1172 may be formed in the shape of an elongated bar, and may have through holes formed at both ends thereof. The link coupling part 1161*b* of the staple pulley 1161 may be inserted through the through hole at one end of the first link 1172. The second link 1173 may be inserted through the through hole at the other end of the first link 1172.

The second link 1173 may be formed in the shape of an elongated bar and may be coupled to the first link 1172. The second link 1173 may include a first protrusion 1173*a*, a second protrusion 1173*b*, and a fastening part 1173*c*.

In detail, the first protrusion 1173*a* may be formed at one end of the second link 1173. As the through hole of the first link 1172 is fit into the first protrusion 1173*a* and thus axially coupled to the first link 1172, the second link 1173 may be coupled to the first link 1172. In addition, the first protrusion 1173*a* may be fit into a guide groove 1101*b* of the first jaw 1101, which will be described below.

In addition, the second protrusion 1173*b* may be formed in a central area of the second link 1173. The second protrusion 1173*b* may be fit into the guide groove 1101*b* of the first jaw 1101, which will be described below.

As such, as the first protrusion 1173*a* and the second protrusion 1173*b* move along the guide groove 1101*b* in a state in which the first protrusion 1173*a* and the second protrusion 1173*b* of the second link 1173 formed in a protruding shape are fit into the groove-shaped guide groove 1101*b*, the staple link assembly 1170 moves with respect to the first jaw 1101 (and the cartridge 1500 therein). This will be described in more detail below.

In addition, the fastening part 1173*c* may be formed at the other end of the second link 1173. The fastening part 1173*c* may be coupled to the moving member 1550 of the cartridge 1500, which will be described below.

In the state as illustrated in FIG. 6, when the staple pulley 1161 rotates clockwise, the link member 1171 connected to the staple pulley 1161 may move as a whole toward the distal end (see 1101*f* of FIG. 7) of the first jaw 1101. On the contrary, when the staple pulley 1161 rotates counterclockwise, the link member 1171 connected to the staple pulley 1161 may move as a whole toward the proximal end (see 1101*g* of FIG. 7) of the first jaw 1101.

Thus, a bidirectional rotational motion of the staple pulley assembly 1160 causes a reciprocating linear motion of the moving member 1550 of the cartridge 1500 through the staple link assembly 1170. This will be described in more detail below.

(First and Second Jaws and Motions)

Figure 7:
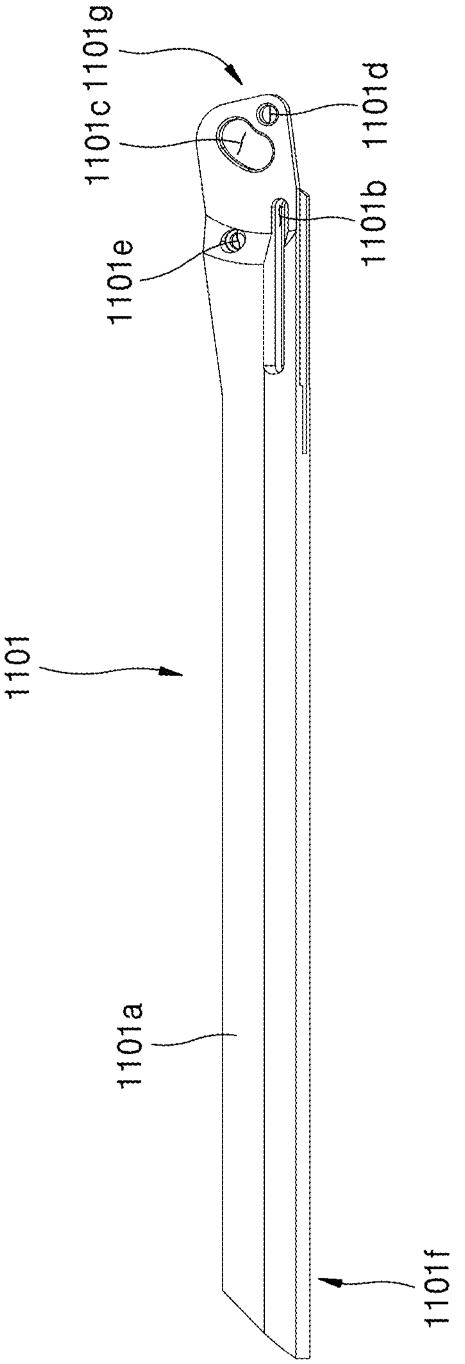
FIG. 7 is a plan view illustrating a first jaw of the end tool of the surgical instrument of FIG. 3.

FIG. 7 is a plan view illustrating a first jaw of the surgical instrument of FIG. 3.

Figure 8:
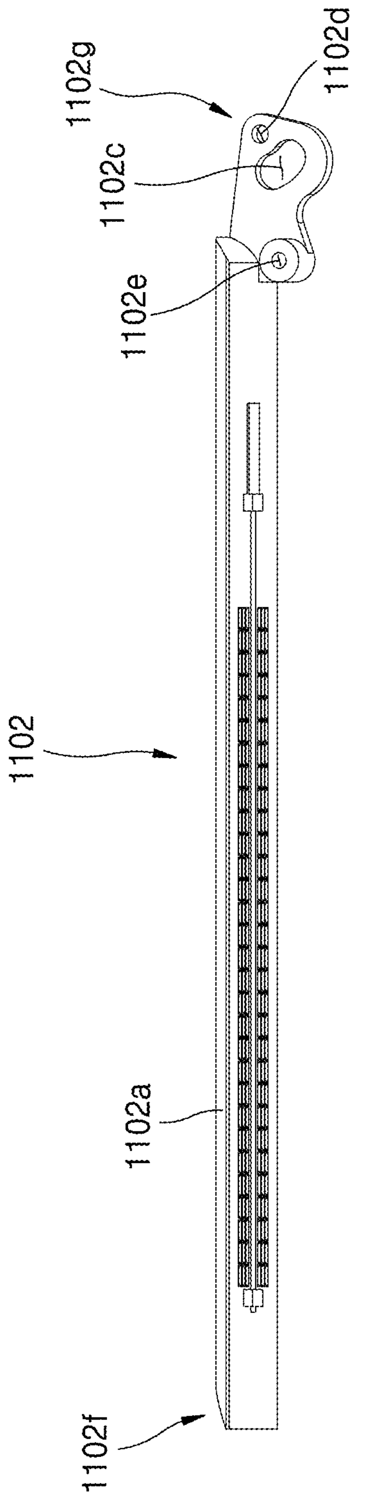
FIG. 8 is a plan view illustrating a second jaw of the end tool of the surgical instrument of FIG. 3.

FIG. 8 is a plan view illustrating a second jaw of the surgical instrument of FIG. 3.

Figure 9:
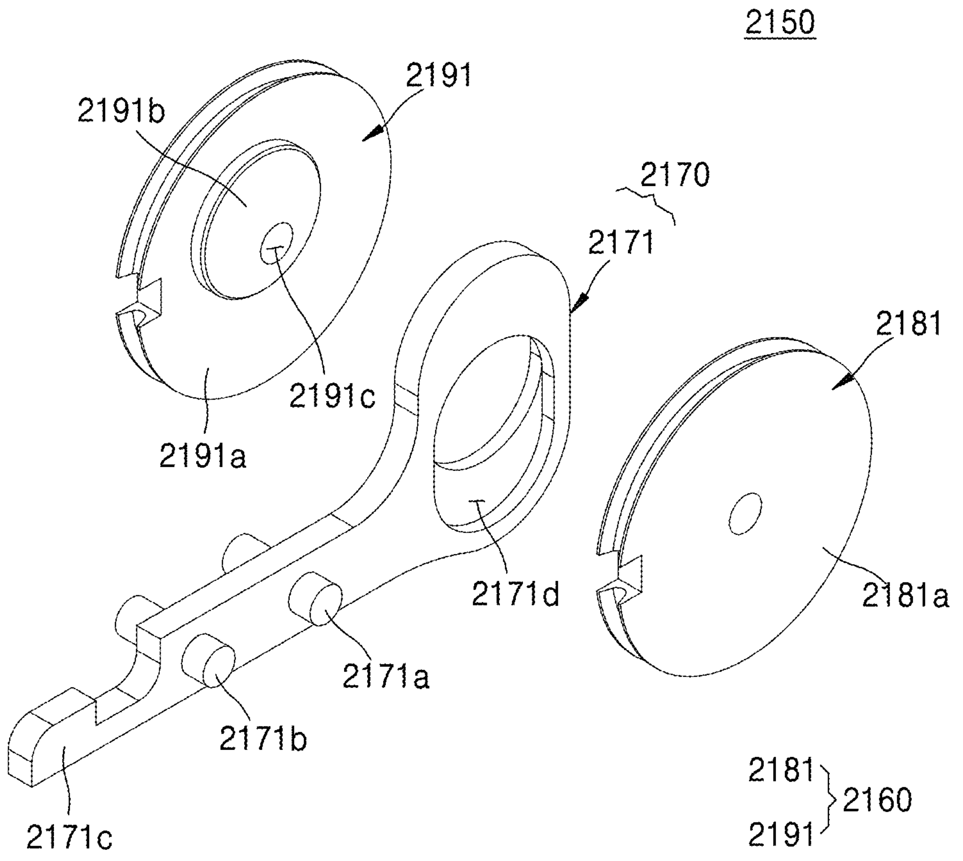
FIGS. 9 and 10 are exploded perspective views illustrating a modification of a staple driving assembly of the surgical instrument of FIG. 1.

Referring to FIGS. 9 and 8 and the like, the first jaw 1101 includes a cartridge accommodation part 1101*a*, the guide groove 1101*b*, a movable-coupling hole 1101*c*, a jaw pulley coupling hole 1101*d*, and a shaft pass-through part 1101*c*.

The first jaw 1101 is formed entirely in the shape of an elongated bar, the cartridge 1500 is accommodated on the side of a distal end 1101*f*, and the pulley 1111 is coupled to a proximal end 1101*g*, such that the first jaw 1101 is formed to be rotatable around the rotation shaft 1141. In other words, the first jaw 1101 may be formed overall in the shape of a hollow box with one surface (upper surface) removed, such that a cartridge accommodation part 1101*a* for accommodating the cartridge 1500 may be formed inside the first jaw 1101. That is, the first jaw 1101 may be formed in an approximately "U" shape in cross section.

The guide groove 1101*b* to guide the movement of the staple link assembly 1170 to be described below may be formed on one side of the cartridge accommodation part 1101*a* of the first jaw 1101, for example, on the side of the proximal end 1101*g*. The guide groove 1101*b* may be formed in the shape of a groove along a moving path of the staple link assembly 1170. In addition, as the first protrusion 1173*a* and the second protrusion 1173*b* move along the guide groove 1101*b* in a state in which the first protrusion 1173*a* and the second protrusion 1173*b* of the second link 1173 formed in a protruding shape are fit into the groove-shaped guide groove 1101*b*, the staple link assembly 1170 moves with respect to the first jaw 1101 (and the cartridge 1500 therein). That is, the staple link assembly 1170 may move along the guide groove 1101*b* of the first jaw 1101.

In addition, the movable-coupling hole 1101*c*, the jaw pulley coupling hole 1101*d*, and the shaft pass-through part 1101*e* may be formed on the side of the proximal end of the first jaw 1101.

Here, the movable-coupling hole 1101*c* may be formed to have a certain curvature, and may be formed in an approximately elliptical shape. A shaft coupling part of the pulley 1111 may be fit into the movable-coupling hole 1101*c*. Here, a short radius of the movable-coupling hole 1101*c* may be formed to be substantially the same as or slightly greater than a radius of the shaft coupling part. In addition, a long radius of the movable-coupling hole 1101*c* may be greater than the radius of the shaft coupling part. Thus, the shaft coupling part is formed to be movable to a certain extent within the movable-coupling hole 1101*c* in a state in which the shaft coupling part of the pulley 1111 is fit into the movable-coupling hole 1101*c* of the first jaw 1101.

In addition, the jaw pulley coupling hole 1101*d* is formed in the form of a cylindrical hole, and a jaw coupling part of the pulley 1111 may be fit into the jaw pulley coupling hole 1101*d*. Here, a radius of the jaw pulley coupling hole 1101*d* may be substantially equal to or slightly greater than a radius of the jaw coupling part. Thus, the jaw coupling part of the pulley 1111 may be formed to be rotatably coupled to the jaw pulley coupling hole 1101*d* of the first jaw 1101.

The shaft pass-through part 1101*e* may be formed to be closer to the distal end 1101*f* of the first jaw 1101 than the movable-coupling hole 1101*c* and the jaw pulley coupling hole 1101*d*. The shaft pass-through part 1101*e* may be formed in the shape of a hole, and the jaw rotation shaft may be inserted through the shaft pass-through part 1101*c*.

The second jaw 1102 includes an anvil 1102*a*, a movable-coupling hole 1102*c*, a jaw pulley coupling hole 1102*d*, and a shaft pass-through part 1102*c*.

The second jaw 1102 is formed overall in the shape of an elongated bar, the anvil 1102*a* is formed on the side of a distal end 1102*f*, and the pulley 1121 is coupled to a proximal end 1102*g*, such that the second jaw 1102 is formed to be rotatable around the rotation shaft 1141.

In detail, the anvil 1102*a* is formed in the form of a flat plane, and shapes corresponding to the shapes of staples 1530 to be described below may be formed on one surface of the anvil 1102*a*. The anvil 1102*a* may serve as a support to support the opposite side of the working member 1540 when the working member 1540 pushes up the staple 1530 during a stapling motion, such that the staple 1530 is bent.

In addition, the movable-coupling hole 1102*c*, the jaw pulley coupling hole 1102*d*, and the shaft pass-through part 1102*e* may be formed on the side of the proximal end of the second jaw 1102.

Here, the movable-coupling hole 1102*c* may be formed to have a certain curvature, and may be formed in an approximately elliptical shape. A shaft coupling part of the pulley 1121 may be fit into the movable-coupling hole 1102*c*. Here, a short radius of the movable-coupling hole 1102*c* may be formed to be substantially the same as or slightly greater than a radius of the shaft coupling part. In addition, a long radius of the movable-coupling hole 1102*c* may be greater than the radius of the shaft coupling part. Thus, the shaft coupling part is formed to be movable to a certain extent within the movable-coupling hole 1102*c* in a state in which the shaft coupling part of the pulley 1121 is fit into the movable-coupling hole 1102*c* of the second jaw 1102.

In addition, the jaw pulley coupling hole 1102*d* is formed in the form of a cylindrical hole, and a jaw coupling part of the pulley 1121 may be fit into the jaw pulley coupling hole 1102*d*. Here, a radius of the jaw pulley coupling hole 1102*d* may be substantially equal to or slightly greater than a radius of the jaw coupling part. Thus, the jaw coupling part of the pulley 1121 may be formed to be rotatably coupled to the jaw pulley coupling hole 1102*d* of the second jaw 1102.

In addition, the shaft pass-through part 1102*e* may be formed to be closer to the proximal end 1102*g* of the second jaw 1102 than the movable-coupling hole 1102*c* and the jaw pulley coupling hole 1102*d*. The shaft pass-through part

1102*e* may be formed in the shape of a hole, and the jaw rotation shaft may be inserted through the shaft pass-through part 1102*c*.

The coupling relationship between the components described above is as follows.

The rotation shaft 1141, which is an end tool jaw pulley rotation shaft, is inserted sequentially through the shaft coupling part of the pulley 1111, the movable-coupling hole 1101*c* of the first jaw 1101, the shaft pass-through part 1161*a* of the staple pulley 1161, the movable-coupling hole 1102*c* of the second jaw 1102, and a shaft coupling part 1121*a* of the pulley 1121.

The jaw rotation shaft is inserted sequentially through the shaft pass-through part 1101*e* of the first jaw 1101 and the shaft pass-through part 1102*e* of the second jaw 1102.

The shaft coupling part of the pulley 1111 is fit into the movable-coupling hole 1101*c* of the first jaw 1101, and the jaw coupling part of the pulley 1111 is fit into the jaw pulley coupling hole 1101*d* of the first jaw 1101.

Here, the jaw pulley coupling hole 1101*d* of the first jaw 1101 and the jaw coupling part of the pulley 1111 are axially coupled to each other to be rotatable, and the movable-coupling hole 1101*c* of the first jaw 1101 and the shaft coupling part of the pulley 1111 are movably coupled to each other.

The shaft coupling part 1121*a* of the pulley 1121 is fit into the movable-coupling hole 1102*c* of the second jaw 1102, and a jaw coupling part 1121*b* of the pulley 1121 is fit into the jaw pulley coupling hole 1102*d* of the second jaw 1102.

Here, the jaw pulley coupling hole 1102*d* of the second jaw 1102 and the jaw coupling part 1121*b* of the pulley 1121 are axially coupled to each other to be rotatable, and the movable-coupling hole 1102*c* of the second jaw 1102 and the shaft coupling part 1121*a* of the pulley 1121 are movably coupled to each other.

Here, the pulley 1111 and the pulley 1121 rotate around the rotation shaft 1141, which is an end tool jaw pulley rotation shaft. The first jaw 1101 and the second jaw 1102 rotate around the jaw rotation shaft. That is, the pulley 1111 and the first jaw 1101 have different rotation shafts. Similarly, the pulley 1121 and the second jaw 1102 have different rotation shafts.

That is, the rotation angle of the first jaw 1101 is limited to a certain extent by the movable-coupling hole 1101*c*, but is basically rotate around a rotation shaft 1145, which is a jaw rotation shaft. Similarly, the rotation angle of the second jaw 1102 is limited to a certain extent by the movable-coupling hole 1102*c*, but is basically rotate around the rotation shaft 1145, which is a jaw rotation shaft.

Through this, a grip force may be amplified. In the surgical instrument 1000 according to an embodiment of the present disclosure, the coupling structure of the first jaw 1101 and the second jaw 1102 forms an X-shaped structure, and thus, when the first jaw 1101 and the second jaw 1102 rotate in directions in which they approach each other (i.e., when the first jaw 1101 and the second jaw 1102 are closed), the grip force becomes stronger in a direction in which the first jaw 1101 and the second jaw 1102 are closed. This will be described in more detail as follows.

As described above, in motions of opening and closing the first jaw 1101 and the second jaw 1102, there are two shafts that serve as the center of rotation of the jaws. That is, the first jaw 1101 and the second jaw 1102 perform opening and closing motions around two shafts, i.e., the rotation shaft 1141 and another rotation shaft.

Meanwhile, although not illustrated, in an alternative embodiment, the first jaw 1101 and the second jaw 1102 may perform a motion around one rotation shaft. For example, the jaw pulley rotation shaft and the jaw rotation shaft may be the same.

(Modification of Staple Driving Assembly)

Hereinafter, a modification of the staple driving assembly (1150 of FIG. 6 and the like) of the surgical instrument 1000 of FIG. 1 will be described.

Figure 10:
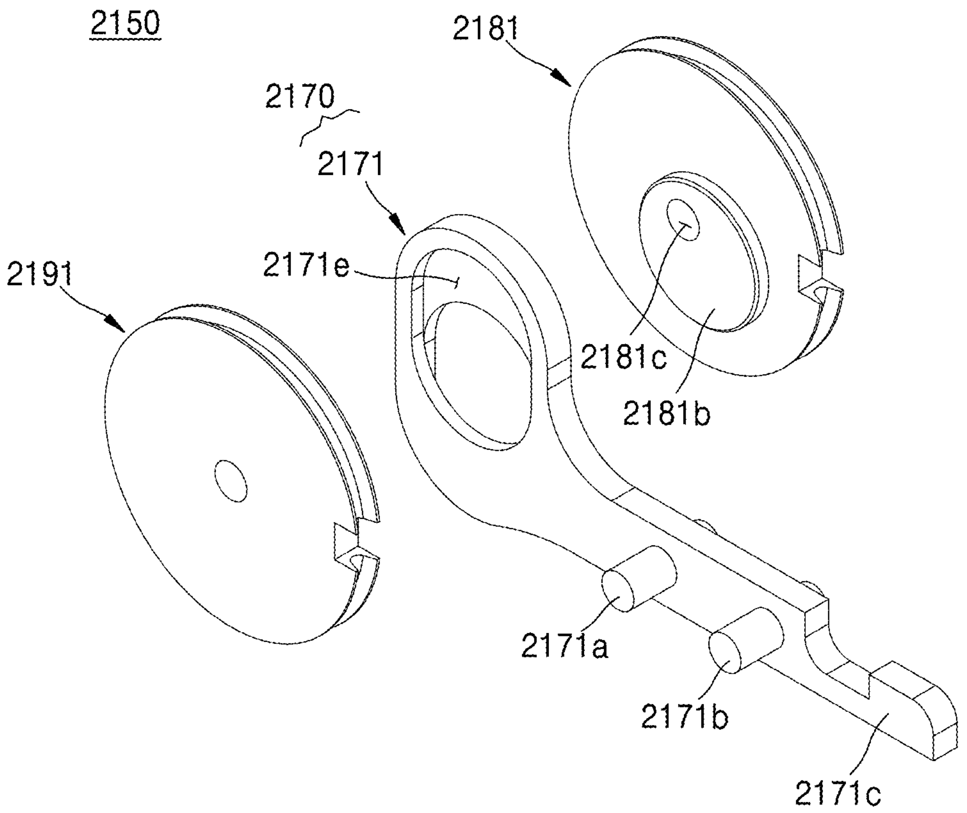

FIGS. 9 and 10 are exploded perspective views illustrating a modification of the staple driving assembly of the surgical instrument of FIG. 1.

Figure 11:
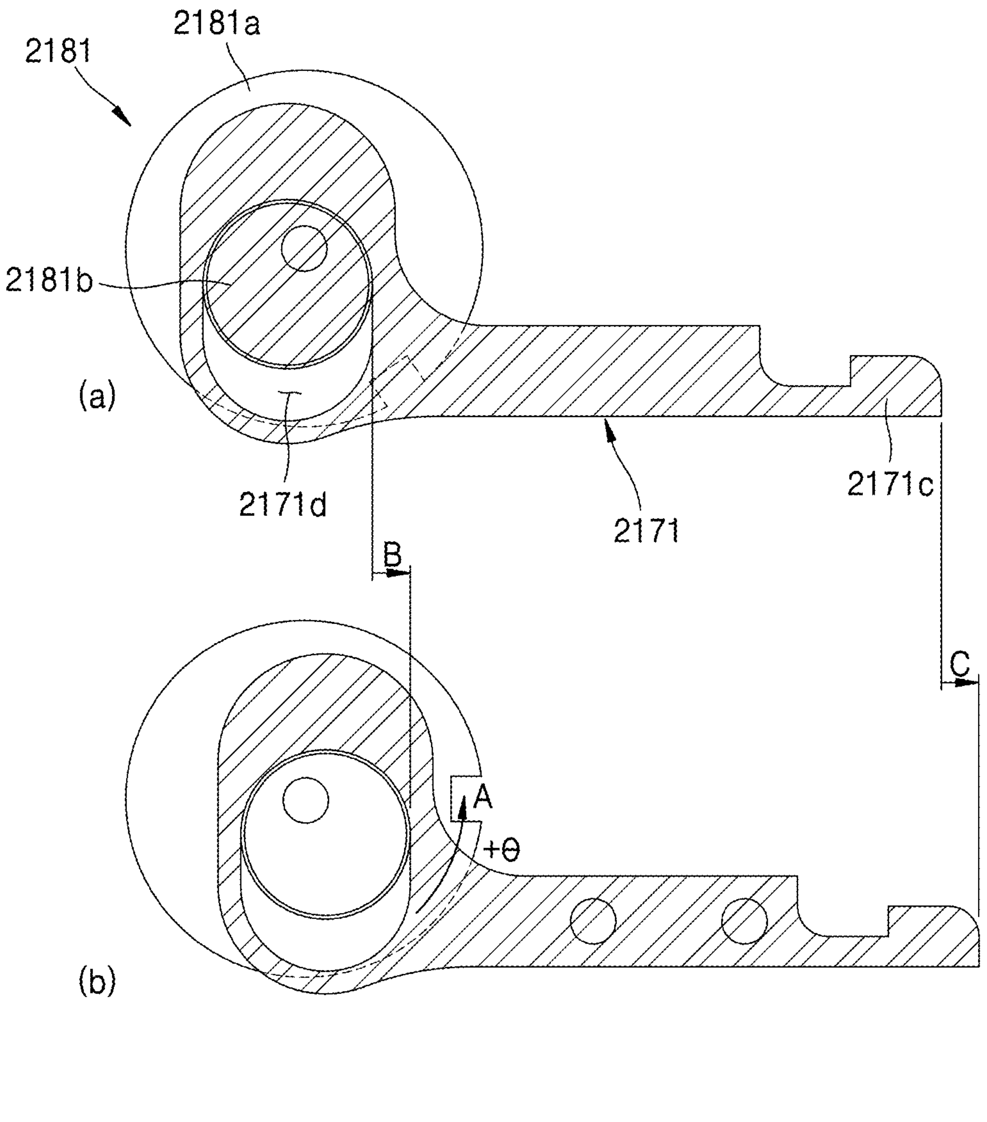
FIGS. 11 and 12 are side views of the staple driving assembly of FIGS. 9 and 10.
Figure 12:
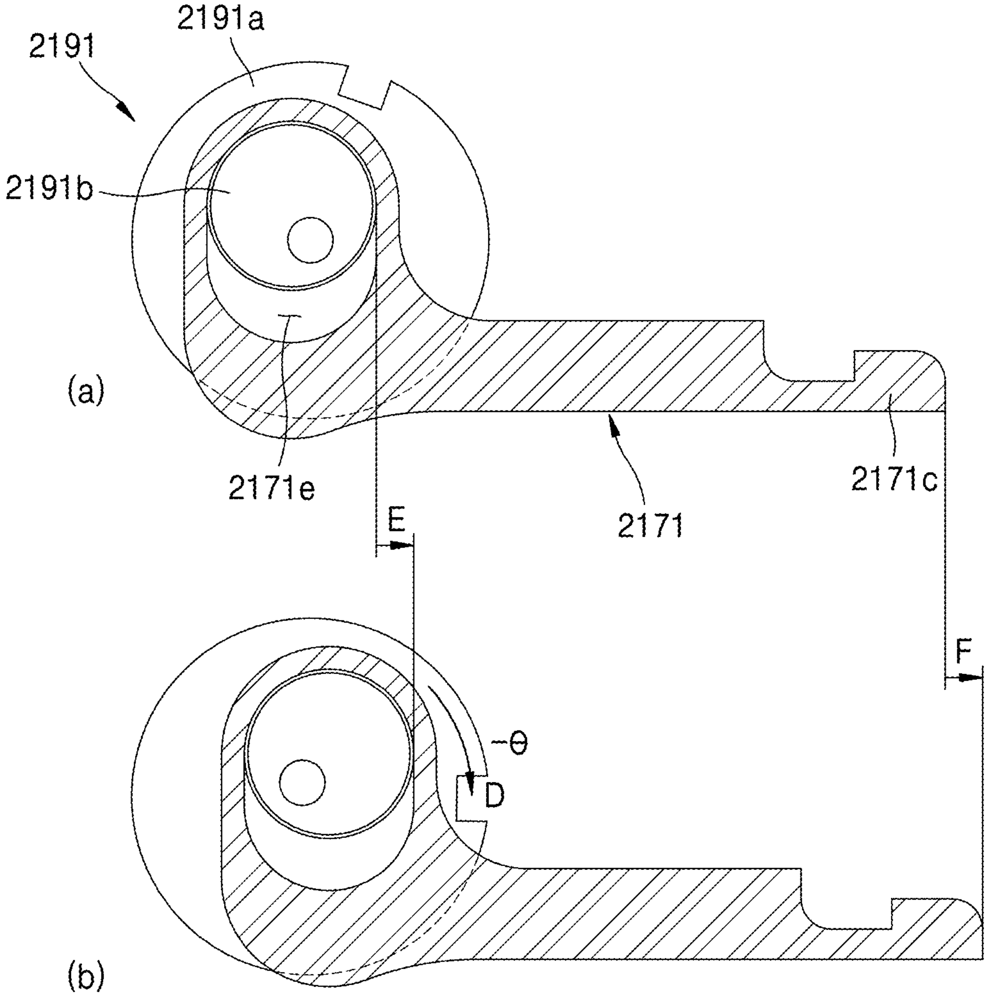

FIGS. 11 and 12 are side views illustrating a modification of the staple driving assembly of the surgical instrument of FIG. 1.

Figure 13:
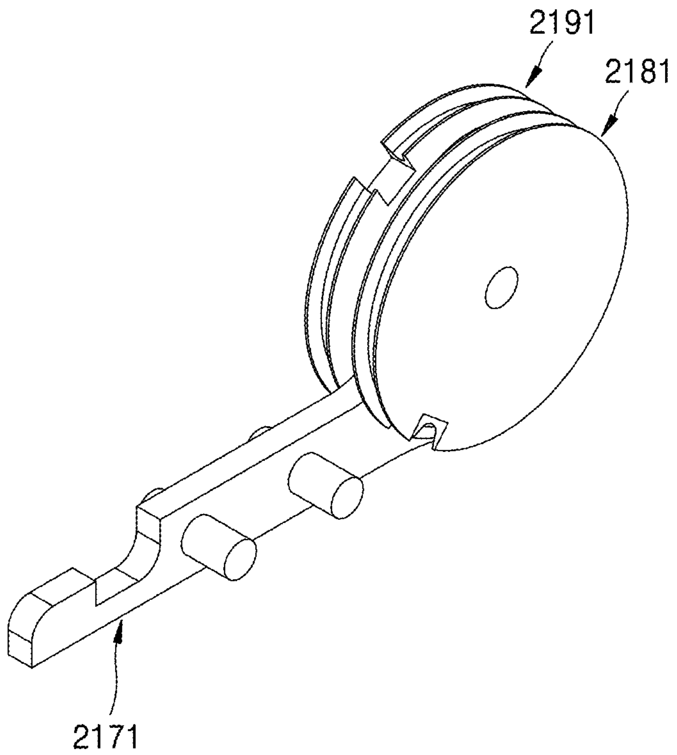
FIGS. 13 and 14 are diagrams for describing a motion of the staple driving assembly of FIGS. 9 to 12.
Figure 14:
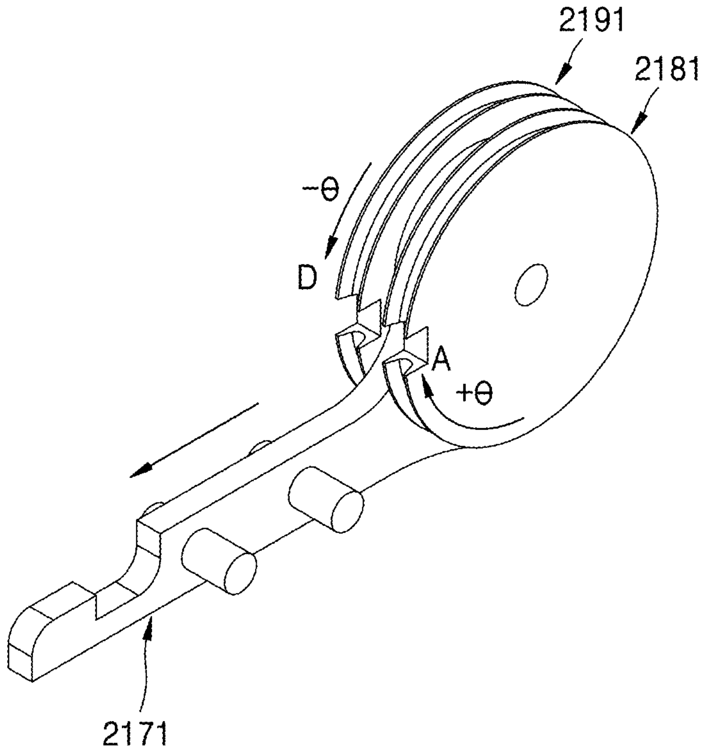

FIGS. 13 and 14 are perspective views illustrating a motion of the staple driving assembly of FIGS. 9 to 12.

Referring to FIGS. 9 to 14, a staple driving assembly 2150 may include a staple pulley assembly 2160 and a staple link assembly 2170. Here, the staple driving assembly 2150 is connected to the moving member 1550 of the cartridge 1500 described above, to convert a rotational motion of the staple pulley assembly 2160 into a linear motion of the moving member 1550.

The staple pulley assembly 2160 may include one or more staple pulleys. The staple pulley assembly 2160 may include a first staple pulley 2181 and a second staple pulley 2191.

The staple link assembly 2170 may include one or more link members 2171. In addition, the link member 2171 may include one or more links. For example, in the present modification, it is assumed that the staple link assembly 2170 includes one link member 2171, and the link member 2171 includes one link.

In the present modification, the staple pulley assembly 2160 and the staple link assembly 2170 form a cam/slot structure. In addition, with such a structure, the effect of amplifying a force for moving the moving member 1550 forward may be obtained.

In detail, the staple pulley assembly 2160 may include the first staple pulley 2181 and the second staple pulley 2191.

The first staple pulley 2181 may include the main body 2181*a*, a protruding member 2181*b*, and a shaft pass-through part 2181*c*.

The main body 2181*a* is formed in a disk shape.

The shaft pass-through part 2181*c* may be formed in a central portion of the main body 2181*a*. The shaft pass-through part 2181*c* may be formed in the form of a hole, and an end tool jaw pulley rotation shaft may be inserted through the shaft pass-through part 2181*c*.

In addition, the protruding member 2181*b* may be formed on the main body 2181*a* of the first staple pulley 2181. The protruding member 2181*b* may be coupled to the link member 2171 of the staple link assembly 2170. Here, the center of the protruding member 2181*b* may not coincide with the center of the first staple pulley 2181, and the protruding member 2181*b* may be formed to be eccentric to a certain extent with respect to the first staple pulley 2181. The protruding member 2181*b* may be fit into a first slot 2171*d* of the link member 2171 to be described below.

The second staple pulley 2191 may include a main body 2191*a*, a protruding member 2191*b*, and a shaft pass-through part 2191*c*.

The main body 2191*a* is formed in a disk shape.

The shaft pass-through part 2191*c* may be formed in a central portion of the main body 2191*a*. The shaft pass-through part 2191*c* may be formed in the form of a hole, and an end tool jaw pulley rotation shaft may be inserted through the shaft pass-through part 2191*c*.

In addition, the protruding member 2191*b* may be formed on the main body 2191*a* of the second staple pulley 2191. The protruding member 2191*b* may be coupled to the link member 2171 of the staple link assembly 2170. Here, the center of the protruding member 2191*b* may not coincide with the center of the second staple pulley 2191, and the protruding member 2191*b* may be formed to be eccentric to a certain extent with respect to the second staple pulley 2191. The protruding member 2191*b* may be fit into a second slot 2171*e* of the link member 2171 to be described below.

In addition, the end tool 1100 of the present disclosure may further include the staple link assembly 2170 connected to the staple pulley assembly 2160, and the staple link assembly 2170 may include the link member 2171. Here, the staple link assembly 2170 may serve to connect the staple pulley assembly 2160 to the moving member 1550 of the cartridge 1500, which will be described below.

In the present embodiment, the staple link assembly 2170 includes one link member 2171, and the link member 2171 includes only one link. That is, by coupling the staple pulley assembly 2160 to the staple link assembly 2170 by a cam/slot structure, it is possible to convert a rotational motion of the staple pulley assembly 2160 into a linear motion of the staple link assembly 2170 even when the staple link assembly 2170 includes only one link.

In detail, the link member 2171 may be formed as a single link.

The link member 2171 is formed in the form of a combination of an elongated bar and an elliptical flat plate, may have a bent portion, and for example, may be formed in an approximately 'L' shape. Here, the link member 2171 may include a first protrusion 2171*a*, a second protrusion 2171*b*, a fastening part 2171*c*, the first slot 2171*d*, and the second slot 2171*c*.

The first protrusion 2171*a* and the second protrusion 2171*b* may be formed in a central area of the link member 2171. The first protrusion 2171*a* and the second protrusion 2171*b* may be fit into a guide groove (1101*b* of FIG. 7) of the first jaw 1101.

As such, as the first protrusion 2171*a* and the second protrusion 2171*b* are moved along the guide groove 1101*b* in a state in which the first protrusion 2171*a* and the second protrusion 2171*b* of the link member 2171 formed in a protruding shape are fit into the groove-shaped guide groove 1101*b*, the link member 2171 moves with respect to the first jaw 1101 (and the cartridge 1500 therein). This will be described in more detail below.

In addition, the fastening part 2171*c* may be formed at one end of the link member 2171. The fastening part 2171*c* may be coupled to the moving member 1550 of the cartridge 1500.

In addition, the first slot 2171*d* and the second slot 2171*e* may be formed at an end opposite to the end of the link member 2171 at which the fastening part 2171*c* is formed.

In detail, the first slot 2171*d* may be formed on a surface of the link member 2171, which faces the first staple pulley 2181. Here, the first slot 2171*d* may be formed in the shape of an elongated hole, and the protruding member 2181*b* of the first staple pulley 2181 may be inserted into the first slot 2171*d*. The first slot 2171*d* may be formed to have a certain curvature, and may be formed in an approximately elliptical shape. Here, the first slot 2171*d* may be formed to be larger than the protruding member 2181*b* by a certain extent. Thus, the protruding member 2181*b* is formed to be movable to a certain extent inside the first slot 2171*d* in a state in which the protruding member 2181*b* of the first staple pulley 2181 is fit into the first slot 2171*d* of the link member 2171.

As described above, the protruding member 2181*b* may be formed to be eccentric with respect to the center of the first staple pulley 2181 by a certain extent. Accordingly, when the first staple pulley 2181 rotates, the protruding member 2181*b* in contact with the first slot 2171*d* may push the first slot 2171*d* to move the link member 2171. That is, when the first staple pulley 2181 rotates, the protruding member 2181*b* may move while being in contact with the first slot 2171*d* inside the first slot 2171*d*, and accordingly, the link member 2171 may linearly move along the guide groove 1101*b* of the first jaw 1101.

Here, the first slot 2171*d* may be formed not to pass through the entire thickness of the link member 2171, but to pass through about half of the entire thickness of the link member 2171. In other words, the first slot 2171*d* may be formed to have substantially the same thickness as the thickness of the protruding member 2181*b* of the first staple pulley 2181.

In addition, the second slot 2171*e* may be formed in the link member 2171. In detail, the second slot 2171*e* may be formed on a surface of the link member 2171, which faces the second staple pulley 2191. Here, the second slot 2171*e* may be formed in the shape of an elongated hole, and the protruding member 2191*b* of the second staple pulley 2191 may be inserted into the second slot 2171*e*. The second slot 2171*e* may be formed to have a certain curvature, and may be formed in an approximately elliptical shape. Here, the second slot 2171*e* may be formed to be larger than the protruding member 2191*b* by a certain extent. Thus, the protruding member 2191*b* is formed to be movable to a certain extent inside the second slot 2171*e* in a state in which the protruding member 2191*b* of the second staple pulley 2191 is fit into the second slot 2171*e* of the link member 2171.

As described above, the protruding member 2191*b* may be formed to be eccentric with respect to the center of the second staple pulley 2191 by a certain extent. Accordingly, when the second staple pulley 2191 rotates, the protruding member 2191*b* in contact with the second slot 2171*e* may push the second slot 2171*e* to move the link member 2171. That is, when the second staple pulley 2191 rotates, the protruding member 2191*b* may move while being in contact with the second slot 2171*e* inside the second slot 2171*e*, and accordingly, the link member 2171 may linearly move along the guide groove 1101*b* of the first jaw 1101 (see FIG. 7).

Here, the second slot 2171*e* may be formed not to pass through the entire thickness of the link member 2171, but to pass through about half of the entire thickness of the link member 2171. In other words, the second slot 2171*e* may be formed to have substantially the same thickness as the thickness of the protruding member 2191*b* of the second staple pulley 2191.

Here, the first slot 2171*d* and the second slot 2171*e* may be formed to at least partially overlap each other. In addition, the sum of the thicknesses of the first slot 2171*d* and the second slot 2171*e* in the Y-axis direction may be substantially equal to the thickness of the link member 2171 in the Y-axis direction.

Here, the first slot 2171*d* and the second slot 2171*e* may be formed to be vertically symmetrical with respect to the rotation shaft. As such, as the first slot 2171*d* and the second slot 2171*e* are vertically symmetrical with respect to the rotation shaft, the protruding member 2181*b* of the first staple pulley 2181 and the protruding member 2191*b* of the second staple pulley 2191, which are coupled to the link member 2171, may be arranged to be symmetrical with each other. This will be described in more detail below.

(Displacement and Motion of Staple Link Assembly According to Rotation of Staple Pulley)

Hereinafter, displacement of the staple link assembly 2170 according to rotation of the first staple pulley 2181 and the second staple pulley 2191 will be described.

Referring to FIG. 11, the first staple pulley 2181 and the staple link assembly 2170 are coupled to each other in a cam/slot form. That is, the cam-shaped protruding member 2181*b* formed on the first staple pulley 2181 is coupled to the first slot 2171*d* formed in the link member 2171. Thus, when the first staple pulley 2181 rotates in the direction of arrow A, the displacement of the protruding member 2181*b* of the first staple pulley 2181 in the X-axis direction is B. In addition, the displacement of the staple link assembly 2170 in the X-axis direction is C.

Similarly, referring to FIG. 12, in the first embodiment of the present disclosure, the second staple pulley 2191 and the staple link assembly 2170 are coupled to each other in a cam/slot form. That is, the cam-shaped protruding member 2191*b* formed on the second staple pulley 2191 is coupled to the second slot 2171*e* formed in the link member 2171. Thus, when the second staple pulley 2191 rotates in the direction of arrow D, the displacement of the protruding member 2191*b* of the second staple pulley 2191 in the X-axis direction is E. In addition, the displacement of the staple link assembly 2170 in the X-axis direction is F.

In comparison with the above case, in a case in which a staple pulley and a staple link assembly are coupled to each other in a link-shaft manner rather than the cam/slot manner, the displacement of the staple link assembly in the X-axis direction is much longer.

In other words, compared to a case in which the staple pulley and the staple link assembly are axially coupled to each other, in a case in which the staple pulley and the staple link assembly are coupled to each other in the cam/slot manner as in the present modification, the displacement of the staple link assembly displacement in the X-axis direction decreases even when the staple pulley rotates by the same amount.

In addition, because work is the product of force and displacement, assuming that the work for rotating the staple pulley is the same, the displacement and the force are inversely proportional to each other. Thus, when the displacement is reduced, the force increases in inverse proportion to the displacement.

As a result, in the present modification, because the first staple pulley 2181 and the second staple pulley 2191 are each coupled to the staple link assembly 2170 in the cam/slot form, and the displacement of the staple link assembly 2170 in the X-axis direction due to the rotation of the first staple pulley 2181 and the second staple pulley 2191 is relatively reduced compared to the above-described embodiments, the force received by the staple link assembly 2170 in the X-axis direction relatively increases compared to a simple link structure.

According to the present modification as described above, a force for moving forward the staple link assembly 2170 and the moving member 1550 connected thereto may be amplified, and thus, a stapling motion may be performed more robustly.

In particular, in the present modification, because two staple pulleys (i.e., the first staple pulley 2181 and the second staple pulley 2191) symmetrical with each other are provided, the force with which the staple pulley assembly 2160 pushes the staple link assembly 2170 may be amplified by approximately two times compared to a case in which only one staple pulley is provided.

In addition, because the first staple pulley 2181 and the second staple pulley 2191 are arranged to be horizontally symmetrical with each other with respect to an XZ plane, the horizontal balance is achieved in performing a stapling motion, such that the end tool may perform the motion stably with respect to a yaw rotation shaft without shaking left and right. In addition, when the winding directions of the wire corresponding to the first staple pulley 2181 and the wire corresponding to the second staple pulley 2191 are changed to be opposite to each other with respect to the rotation shaft 1143 (see FIG. 3), which is a pitch rotation shaft, shaking with respect to the rotation shaft 1143 may be mutually offset.

Hereinafter, rotation directions of the first staple pulley 2181 and the second staple pulley 2191 will be described.

Referring to FIGS. 11 to 14, the first staple pulley 2181 moves forward the staple link assembly 2170 when rotating in the direction of arrow A of FIG. 14 (i.e., clockwise), and the second staple pulley 2191 moves forward the staple link assembly 2170 when rotating in the direction of arrow D of FIG. 14 (i.e., counterclockwise).

On the contrary, the first staple pulley 2181 moves backward the staple link assembly 2170 when rotating counterclockwise, and the second staple pulley 2191 moves backward the staple link assembly 2170 when rotating clockwise.

Accordingly, when the first staple pulley 2181 and the second staple pulley 2191 rotate in opposite directions, the staple link assembly 2170 is moved (forward or backward). On the contrary, when the first staple pulley 2181 and the second staple pulley 2191 rotate in the same direction, the rotation of the two pulleys is offset, and thus, the staple link assembly 2170 is not moved.

As a result, in a state as illustrated in FIG. 13, when the first staple pulley 2181 rotates clockwise and the second staple pulley 2191 rotates counterclockwise at the same time, the link member 2171 connected to the first staple pulley 2181 and the second staple pulley 2191 may move toward the distal end 1101*f* (see FIG. 13) of the first jaw 1101.

On the contrary, when the first staple pulley 2181 rotates counterclockwise and the second staple pulley 2191 rotates clockwise at the same time, the link member 2171 connected to the first staple pulley 2181 and the second staple pulley 2191 may move toward the proximal end 1101*g* (see FIG. 13) of the first jaw 1101.

Thus, a bidirectional rotational motion of the staple pulley assembly 2160 causes a reciprocating linear motion of the moving member 1550 of the cartridge 1500 through the staple link assembly 2170.

The driving part 1208 may simultaneously drive the first staple pulley 2181 and the second staple pulley 2191 of the staple pulley assembly 2160, and for example, may reverse driving of two wires through a rotational motion of a motor member of the driving part 1208 by using an intermediate conversion member such as a slide member, and drive the first staple pulley 2181 and the second staple pulley 2191 accordingly.

(Cartridge)

Hereinafter, the cartridge 1500 of the surgical instrument 1000 of FIG. 3 will be described in more detail.

Figure 15:
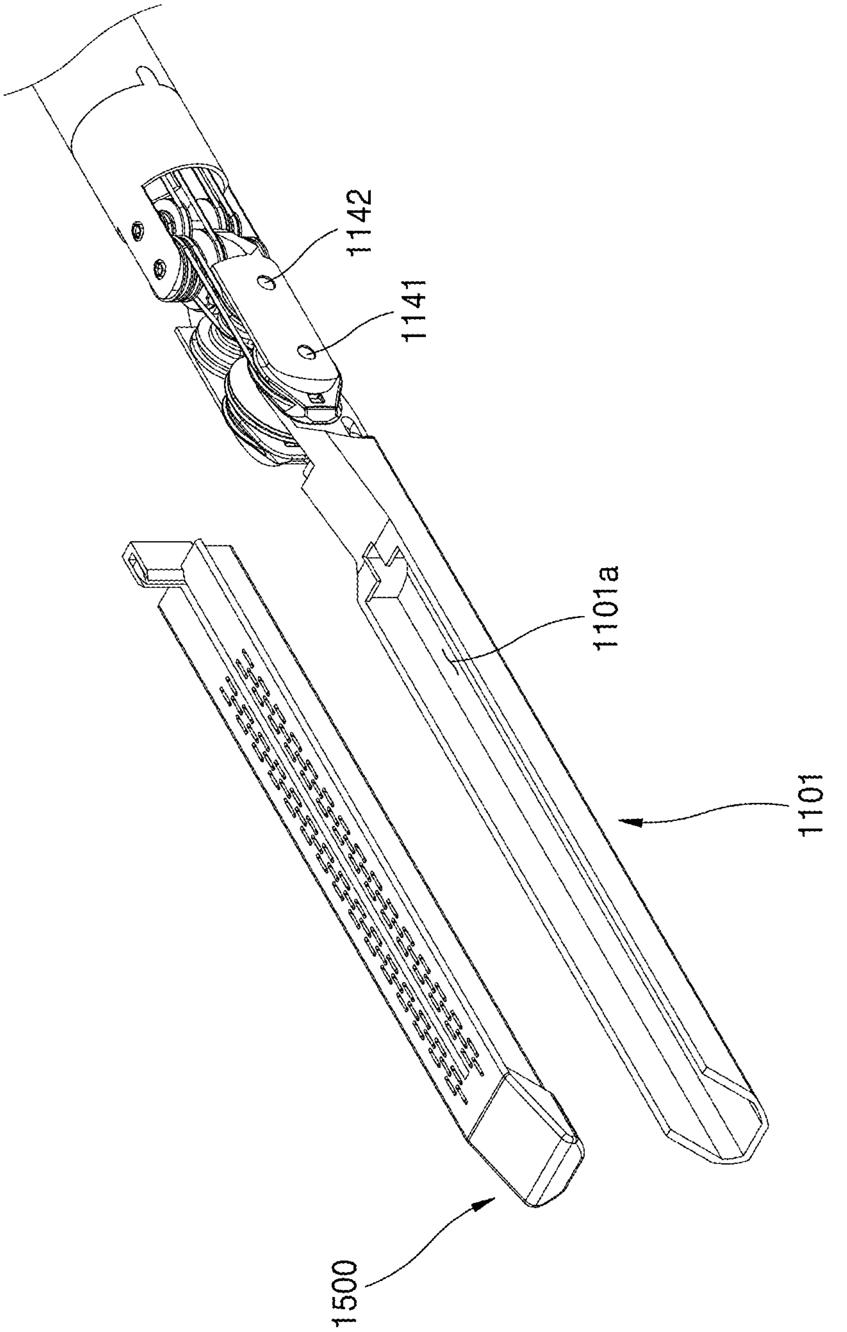
FIG. 15 is a perspective view illustrating a first jaw and a cartridge of the surgical instrument of FIG. 3.
Figure 16:
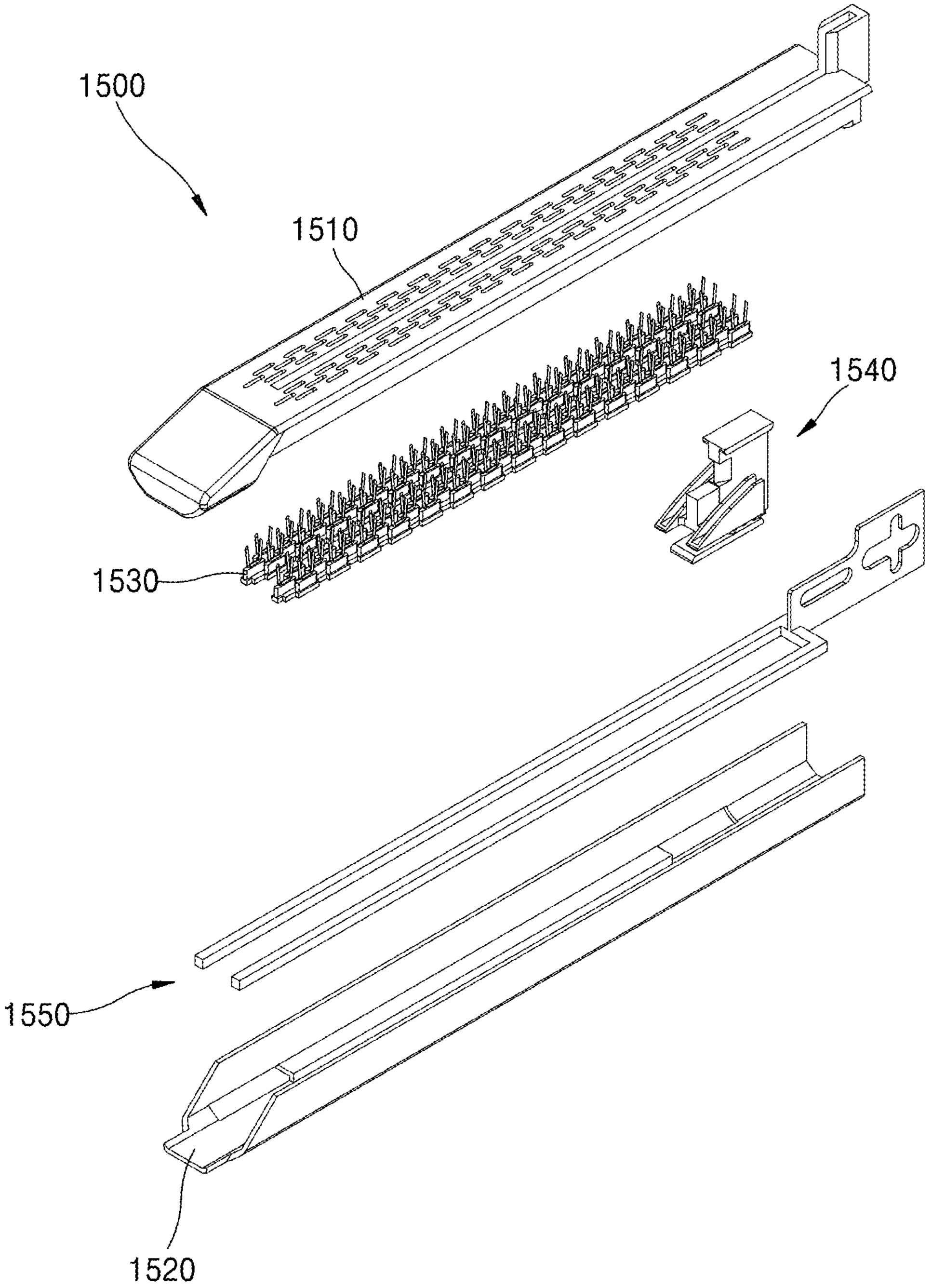
FIG. 16 is an exploded perspective view of the cartridge of FIG. 15.
Figure 17:
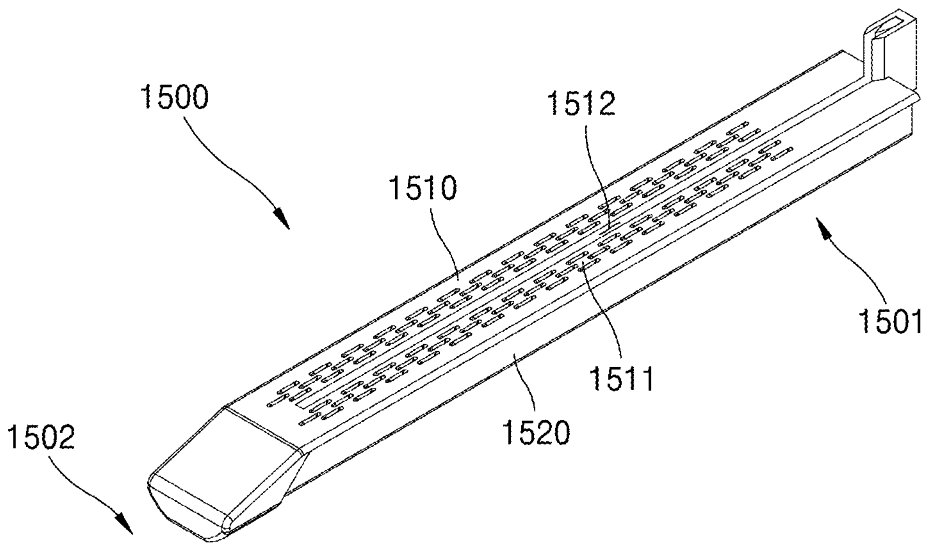
FIG. 17 is a perspective view of the cartridge of FIG. 15.
Figure 18:
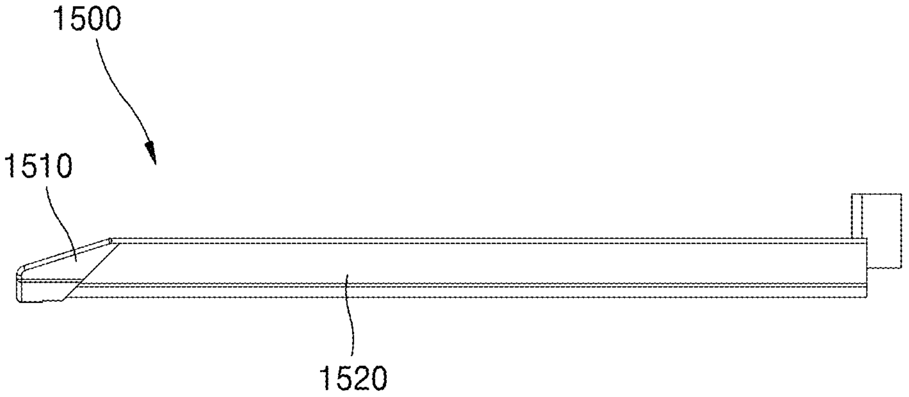
FIG. 18 is a side view of the cartridge of FIG. 15.

FIG. 15 is a perspective view illustrating a first jaw and a cartridge of the surgical instrument of FIG. 3. FIG. 16 is an exploded perspective view of the cartridge of FIG. 15. FIG. 17 is a combined perspective view of the cartridge of FIG. 15. FIG. 18 is a side view of the cartridge of FIG. 15.

Figure 19:
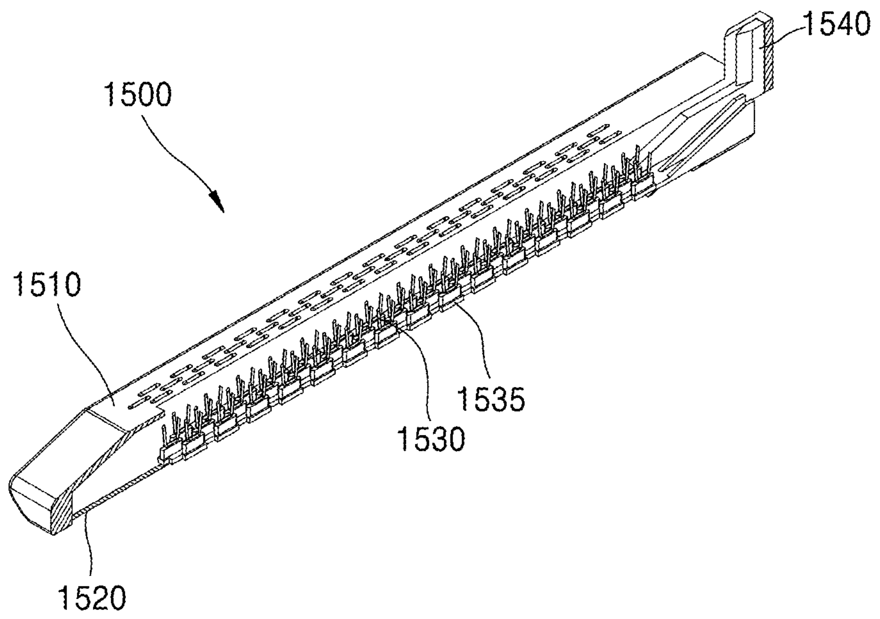
FIG. 19 is a perspective cross-sectional view for describing an internal structure of the cartridge of FIG. 15.
Figure 20:
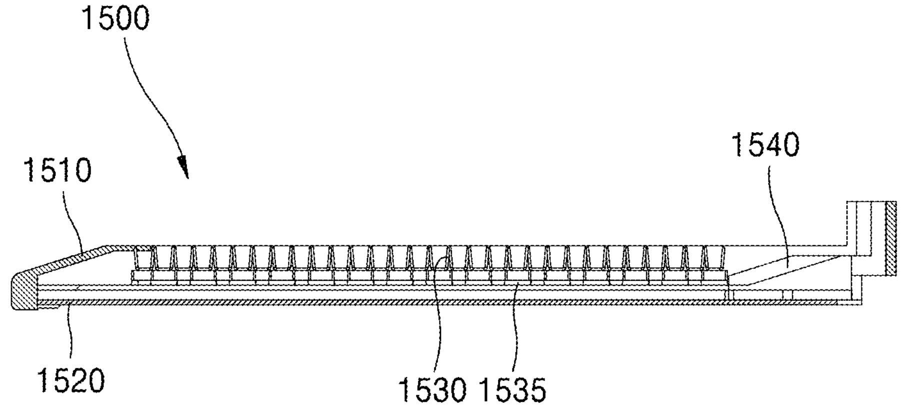
FIG. 20 is a side cross-sectional view for describing an internal structure of the cartridge of FIG. 15.
Figure 21:
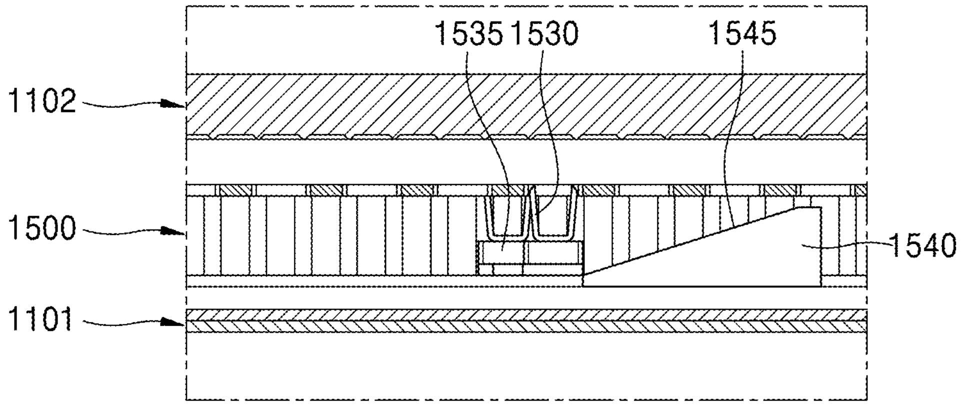
FIG. 21 is a diagram for describing a stapling motion of the end tool of FIG. 3.
Figure 21:
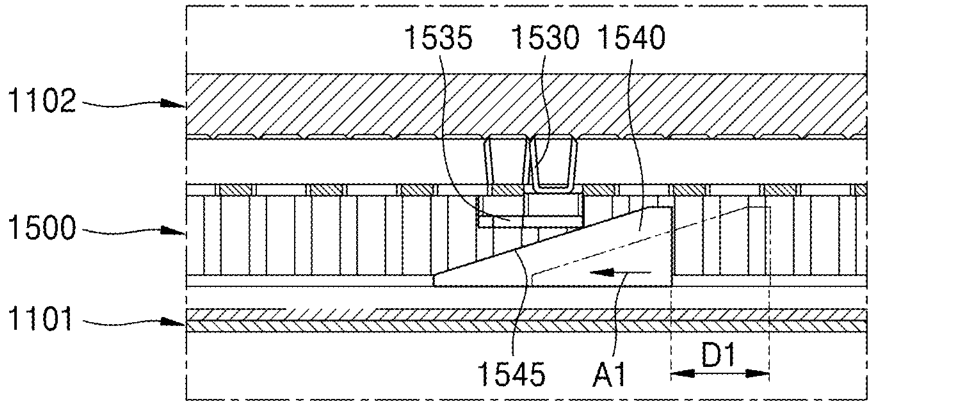
Figure 21:
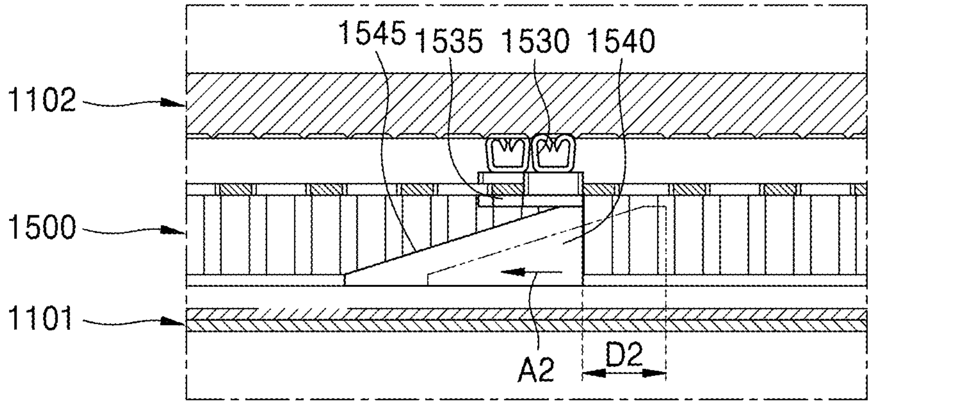

FIG. 19 is a perspective cross-sectional view for describing an internal structure of the cartridge of FIG. 15. FIG. 20 is a side cross-sectional view for describing an internal structure of the cartridge of FIG. 15. FIG. 21 is a diagram for describing a stapling motion of the end tool of FIG. 3.

Referring to FIGS. 15 to 21 and the like, the cartridge 1500 is formed to be mountable to and dismountable from the first jaw 1101, and includes therein a plurality of staples 1530 and a blade 1544 (see FIG. 27) so as to perform suturing and cutting of tissue. Here, the cartridge 1500 may include a cover 1510, a housing 1520, the staples 1530, a release member 1535, the working member 1540, and the moving member 1550.

The housing 1520 forms the exterior of the cartridge 1500, and may be formed overall in the shape of a hollow box with one surface (upper surface) removed, to accommodate therein the moving member 1550, the working member 1540, and the staples 1530. Here, the housing 1520 may be formed in an approximately 'U' shape in cross section.

The cover 1510 is formed to cover an upper portion of the housing 1520. Staple holes 1511 through which a plurality of staples 1530 may be ejected to the outside may be formed in the cover 1510. As the staples 1530, which are accommodated in the housing 1520 before a stapling operation, are pushed up by the working member 1540 during a stapling motion, and then pass through the staple holes 1511 of the cover 1510 to be released to the outside of the cartridge 1500, stapling is performed.

In addition, a first slit 1512 may be formed in the cover 1510 along the lengthwise direction of the cover 1510. The blade 1544 (see FIG. 27) of the working member 1540 may protrude out of the cartridge 1500 through the first slit 1512. As the blade 1544 (see FIG. 27) of the working member 1540 passes along the first slit 1512, stapled tissue may be cut.

The plurality of staples 1530 may be arranged inside the housing 1520. As the working member 1540, which will be described below, linearly moves in one direction, the plurality of staples 1530 may be sequentially pushed up from the inside of the housing 1520 to the outside, thereby performing suturing, that is, stapling. Here, the material of the staples 1530 may include titanium, stainless steel, etc.

In addition, the release member 1535 may be further arranged between the housing 1520 and the staple 1530. In other words, it may also be described that the staple 1530 is arranged on the release member 1535. In this case, the working member 1540 may linearly move in one direction to push up the release member 1535, and the release member 1535 may push up the staples 1530.

This may include a case in which the working member 1540 directly pushes up the staples 1530, and a case in which the working member 1540 pushes up the release member 1535 such that the release member 1535 pushes up the staples 1530 (i.e., a case in which the working member 1540 indirectly pushes up the staples 1530), and thus, it may be described that the working member 1540 pushes up the staples 1530.

The moving member 1550 may be arranged at an inner lower side of the housing 1520.

Here, the moving member 1550 is not fixedly coupled to the other components of the cartridge 1500, and may be formed to be movable with respect to the other components of the cartridge 1500. That is, the moving member 1550 may perform a reciprocating linear motion with respect to the housing 1520 and the cover 1510 coupled to the housing 1520.

The working member 1540 may be arranged inside the housing 1520. The working member 1540 may be formed to be in contact with the moving member 1550, so as to linearly move in one direction according to a linear reciprocating motion of the moving member 1550. In other words, the working member 1540 interacts with the moving member 1550 to perform stapling and cutting while moving in the extension direction of the connection part 1400.

The configuration of the working member 1540 and the moving member 1550 will be described in detail below.

The cartridge 1500 is accommodated in the cartridge accommodation part 1101*a* of the first jaw 1101, and at this time, the moving member 1550 of the cartridge 1500 is coupled to the staple link assembly 1170 of the end tool 1100. Thus, a rotational motion of the staple pulley 1161 of the end tool 1100 is converted into a linear motion of the moving member 1550 through the staple link assembly 1170.

Here, when the moving member 1550 is connected to the staple pulley 1161 through the staple link assembly 1170, and the staple pulley 1161 rotates alternately in the clockwise/counterclockwise directions, the moving member 1550 may repeatedly move forward and backward. In addition, when the moving member 1550 moves forward, the working member 1540 may move forward together with the moving member 1550, and when the moving member 1550 moves backward, only the moving member 1550 may move backward and the working member 1540 may remain stationary in place. As the working member 1540 moves forward while repeating this process, the staple 1530 may be stapled by a wedge 1545 while the blade 1544 (see FIG. 27) cuts stapled tissue.

This will be described in more detail as follows.

(Stapling and Cutting Motions)

When a driving force is transmitted to the staple pulley 1161 by the driving part 1208 through a driving transmission part such as a wire, the staple pulley 1161 rotates in any one of the clockwise and counterclockwise directions, and the staple link assembly 1170 connected to the staple pulley 1161 and the moving member 1550 of the cartridge 1500 connected to the staple link assembly 1170 move toward a distal end 1502 of the cartridge 1500.

In addition, when the moving member 1550 moves toward the distal end 1502 of the cartridge 1500, the working member 1540 in contact with the moving member 1550 moves together with the moving member 1550 toward the distal end 1502 of the cartridge 1500.

In addition, as the working member 1540 moves toward the distal end 1502 of the cartridge 1500, the blade 1544 (see FIG. 27) of the working member 1540 moves toward the distal end 1502 of the cartridge 1500 while the working member 1540 ejects the staples 1530 out of the cartridge 1500.

In addition, when the staple pulley 1161 rotates in the other one of the clockwise and counterclockwise directions, the staple link assembly 1170 connected to the staple pulley 1161 and the moving member 1550 of the cartridge 1500 connected to the staple link assembly 1170 move toward a proximal end 1501 of the cartridge 1500, and at this time, the working member 1540 is stationary.

In addition, as the above operations are repeatedly performed, a stapling motion by the wedge 1545 and a cutting motion by the blade 1544 (see FIG. 27) are simultaneously performed. FIG. 21 is a diagram for describing a stapling motion of the end tool of FIG. 3.

Referring to FIG. 21, in the state as illustrated in (a) of FIG. 21, as the working member 1540 moves in the direction of arrow A1 of (b) of FIG. 21, the wedge 1545 of the working member 1540 pushes up the release member 1535, and the release member 1535 pushes up the lower side of the staple 1530. This causes the staple 1530 to be ejected from the first jaw 1101 and the cartridge 1500.

In this state, when the working member 1540 moves further in the direction of arrow A2 of (c) of FIG. 21, the ejected staple 1530 is continuously pushed up by the working member 1540 while being in contact with the anvil 1102*a* of the second jaw 1102, both ends of the staple 1530 are bent, and thus, stapling is performed.

As the above motions are continuously performed, stapling is sequentially performed from the staple 1530 on the side of the proximal end 1501 to the staple 1530 on the side of the distal end 1502 among the plurality of staples 1530.

(Correlation Between Stapling and Cutting Motions and Other Motions)

Hereinafter, a correlation between stapling and cutting motions and other motions (pitch, yaw, and actuation motions) will be described.

First, when the end tool 1100 performs a pitch motion, the staple pulley 1161 also performs a pitch motion. That is, when the pulley 1111 and the pulley 1121 perform pitch motions of rotating in the same direction around the rotation shaft 1143, the staple pulley 1161 also needs to rotate in the same direction as the pulley 1111 and the pulley 1121. When the staple pulley 1161 does not rotate together with the pulley 1111 and the pulley 1121 when the pulley 1111 and the pulley 1121 rotate around the rotation shaft 1143, there is a risk that the cartridge 1500 connected to the staple pulley 1161 moves with respect to the first jaw 1101 and thus is separated from the first jaw 1101. Further, rotation of the staple pulley 1161 that is not synchronized with that of the pulley 1111 may cause the moving member 1550 to unintentionally move forward, which in turn may cause an unintended stapling motion.

Next, when the end tool 1100 performs a yaw motion, the staple pulley 1161 also performs a yaw motion. That is, when the pulley 1111 and the pulley 1121 perform yaw motions of rotating in the same direction around the rotation shaft 1141, the staple pulley 1161 also needs to rotate in the same direction as the pulley 1111 and the pulley 1121. When the staple pulley 1161 does not rotate together with the pulley 1111 and the pulley 1121 when the pulley 1111 and the pulley 1121 rotate around the rotation shaft 1141, there is a risk that the cartridge 1500 connected to the staple pulley 1161 moves with respect to the first jaw 1101 and thus is separated from the first jaw 1101. Further, rotation of the staple pulley 1161 that is not synchronized with that of the pulley 1111 may cause the moving member 1550 to unintentionally move forward, which in turn may cause an unintended stapling motion.

Next, when the end tool 1100 performs an actuation motion, the staple pulley 1161 rotates together with the pulley 1111. That is, when the pulley 1111 and the pulley 1121 perform actuation motions of rotating in the opposite directions around the rotation shaft 1141, the staple pulley 1161 needs to rotate in the same direction as the pulley 1111. When the staple pulley 1161 does rotate together with the pulley 1111 when the pulley 1111 rotates around the rotation shaft 1143, there is a risk that the cartridge 1500 connected to the staple pulley 1161 moves with respect to the first jaw 1101 and thus is separated from the first jaw 1101. Further, rotation of the staple pulley 1161 that is not synchronized with that of the pulley 1111 may cause the moving member 1550 to unintentionally move forward, which in turn may cause an unintended stapling motion.

In addition, when the end tool 1100 performs stapling and cutting motions, the pulley 1111 and the pulley 1121 do not rotate. That is, when the staple pulley 1161 rotates around the rotation shaft 1141 and the moving member 1550 of the link member 1171, and the cartridge 1500 connected thereto performs a linear reciprocating motion, the pulley 1111 and the pulley 1121 need not to rotate. Otherwise, the first jaw 1101 or the second jaw 1102 rotates during the stapling and cutting motions, and thus, the stapling and cutting motions will not be performed normally.

As a result, when the pulley 1111, which is a first jaw pulley, rotates, the staple pulley 1161 accommodated in the first jaw 1101 also needs to rotate together with the pulley 1111. On the contrary, when the staple pulley 1161 rotates for stapling and cutting, the pulley 1111 and the pulley 1121 needs to maintain their positions without rotating. The above-described correlation between the stapling and cutting motions and other motions (the yaw and actuation motions) are described above.

In other words, it may also be described that the pulley 1111 and the pulley 1121 are independent of rotation of the staple pulley 1161. That is, even when the staple pulley 1161 is rotated by the staple wire, the pulley 1111 and the pulley 1121 may not rotate. On the contrary, it may also be described that the staple pulley 1161 is dependent of rotation of the pulley 1111. That is, when the pulley 1111 is rotated by the jaw wire, the staple pulley 1161 may rotate together with the pulley 1111.

Hereinafter, a movement of the working member and a clutch mechanism of the working member and the moving member will be described.

Figure 37:
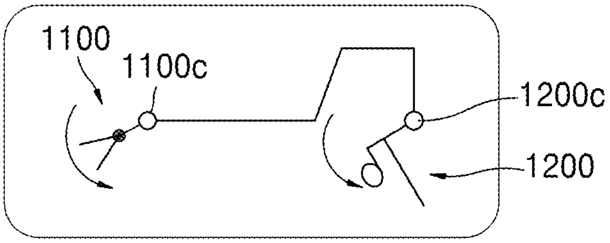
FIG. 37 is a conceptual diagram for describing a motion of the surgical instrument of FIG. 1.
Figure 37:
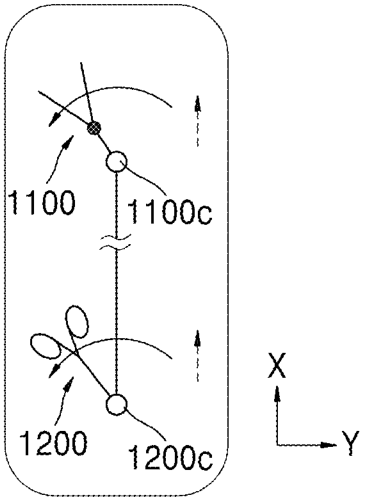

FIG. 37 is a conceptual diagram for describing a motion of the surgical instrument of FIG. 1.

In detail, referring to (a) and (b) of FIG. 37, in the surgical instrument of the present embodiment, the end tool 1100 is formed in front of a center of rotation 1100*c* of the end tool, and the manipulation part 1200 is also formed in front of a center of rotation 1200*c* of the manipulation part 1200, such that the motions of the manipulation part 1200 and the end tool 1100 intuitively match each other. In other words, the surgical instrument according to an embodiment of the present disclosure is formed such that at least a portion of the manipulation part may be closer to the end tool (than its own joint) with respect to its own joint at more than one point in a manipulation process.

FIGS. 38 to 41 are perspective views illustrating a pitch motion of the surgical instrument of FIG. 1.

Figure 38:
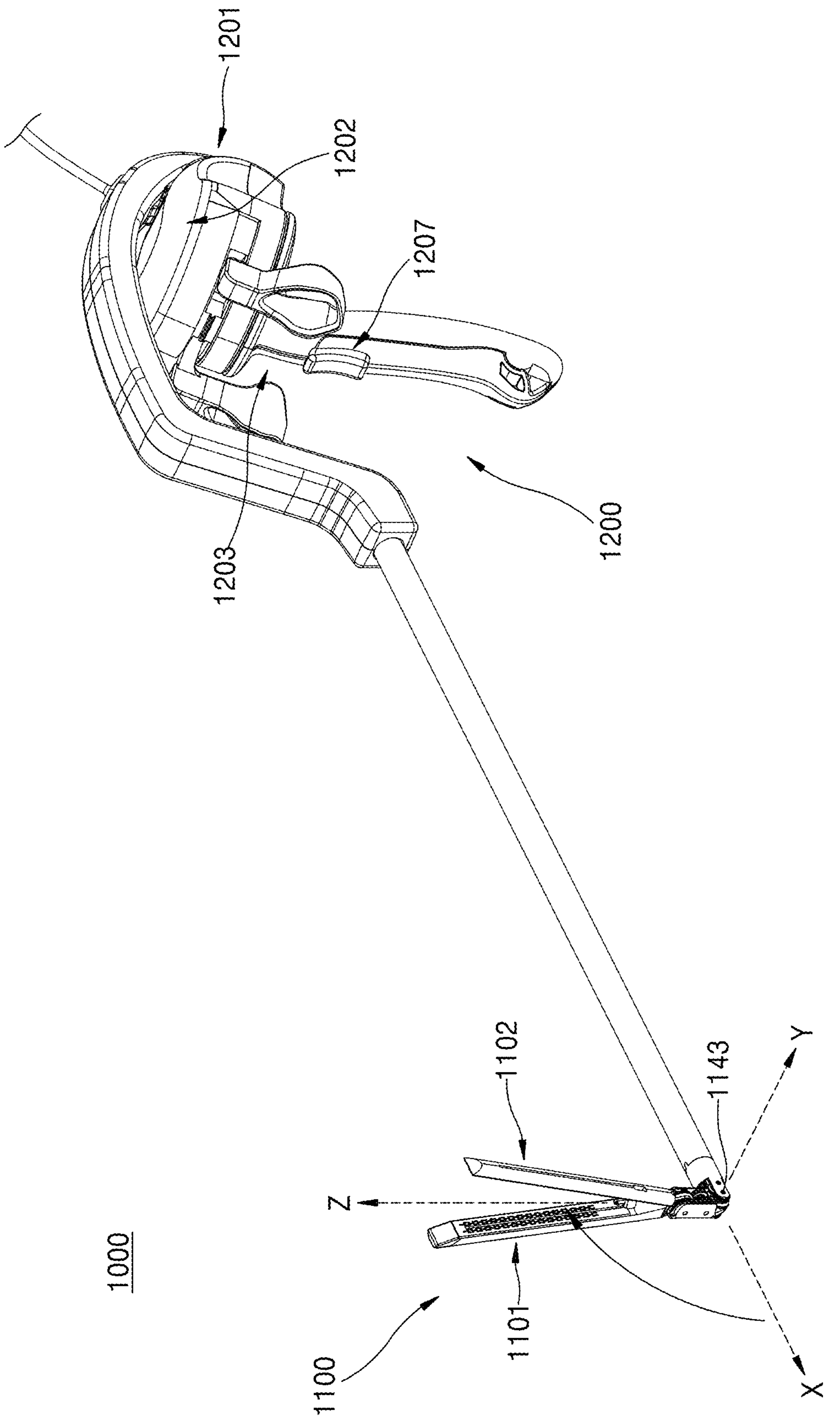
FIGS. 38 to 41 are perspective views illustrating a pitch motion of the surgical instrument of FIG. 1.
Figure 39:
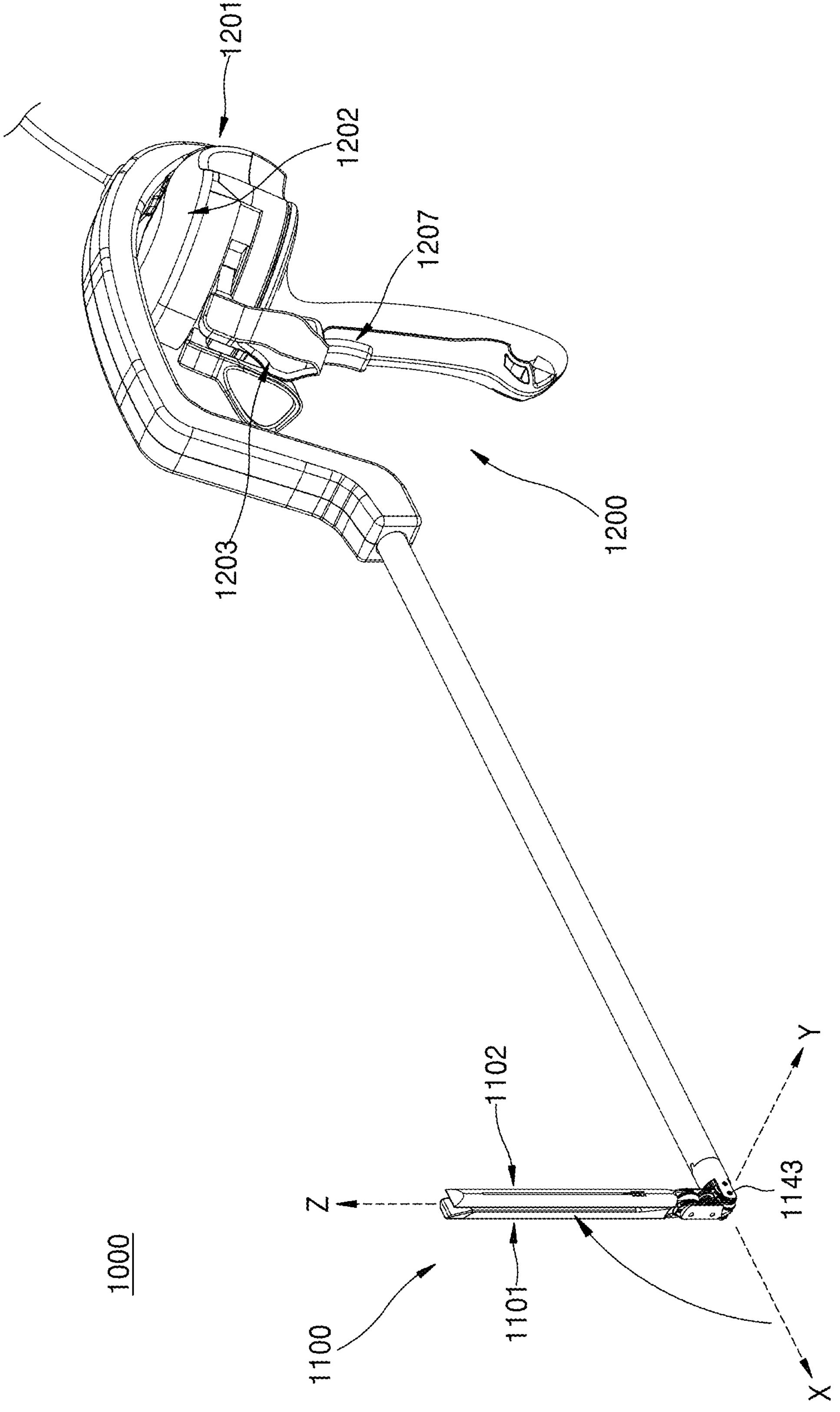
Figure 40:
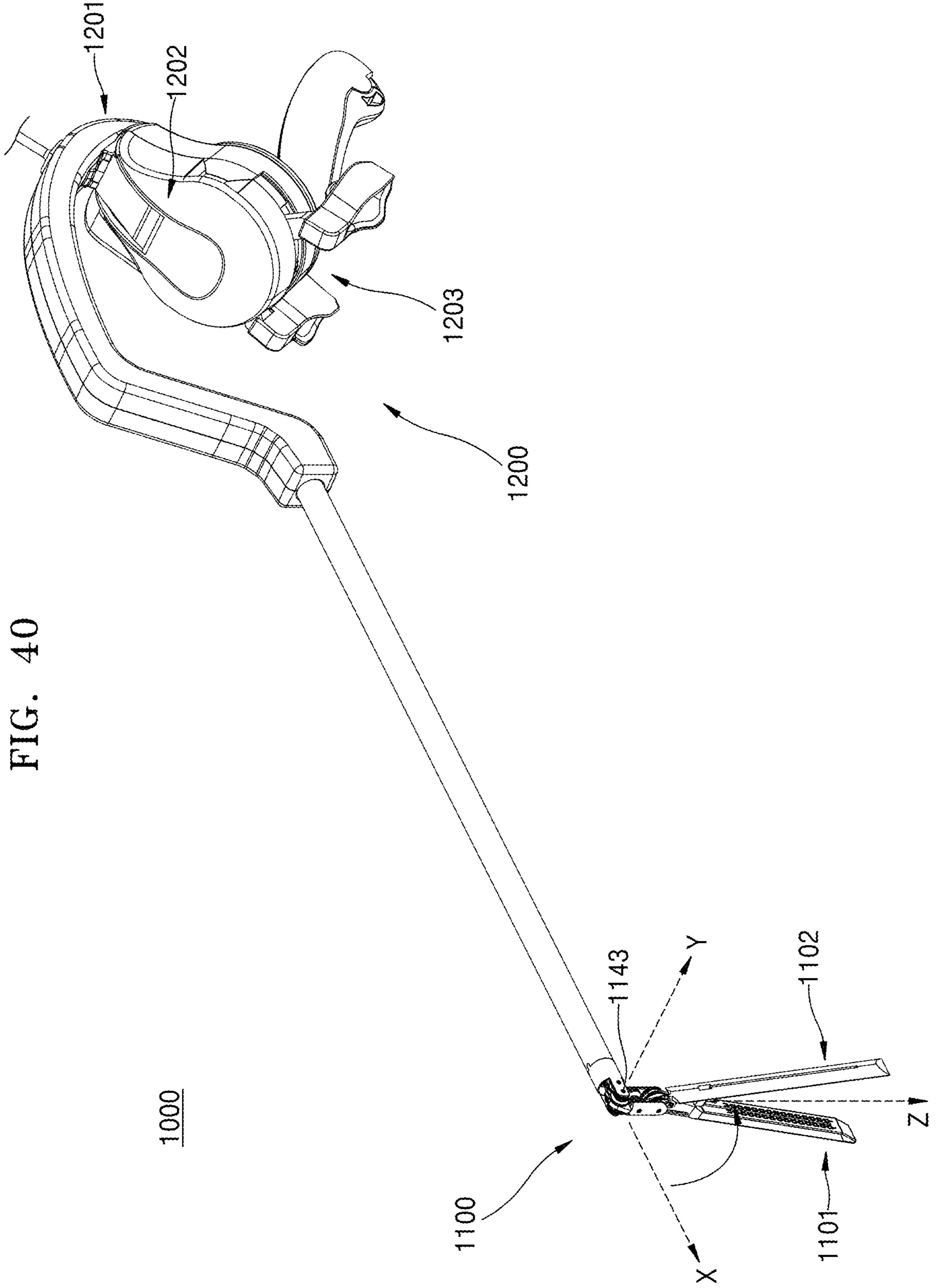
Figure 41:
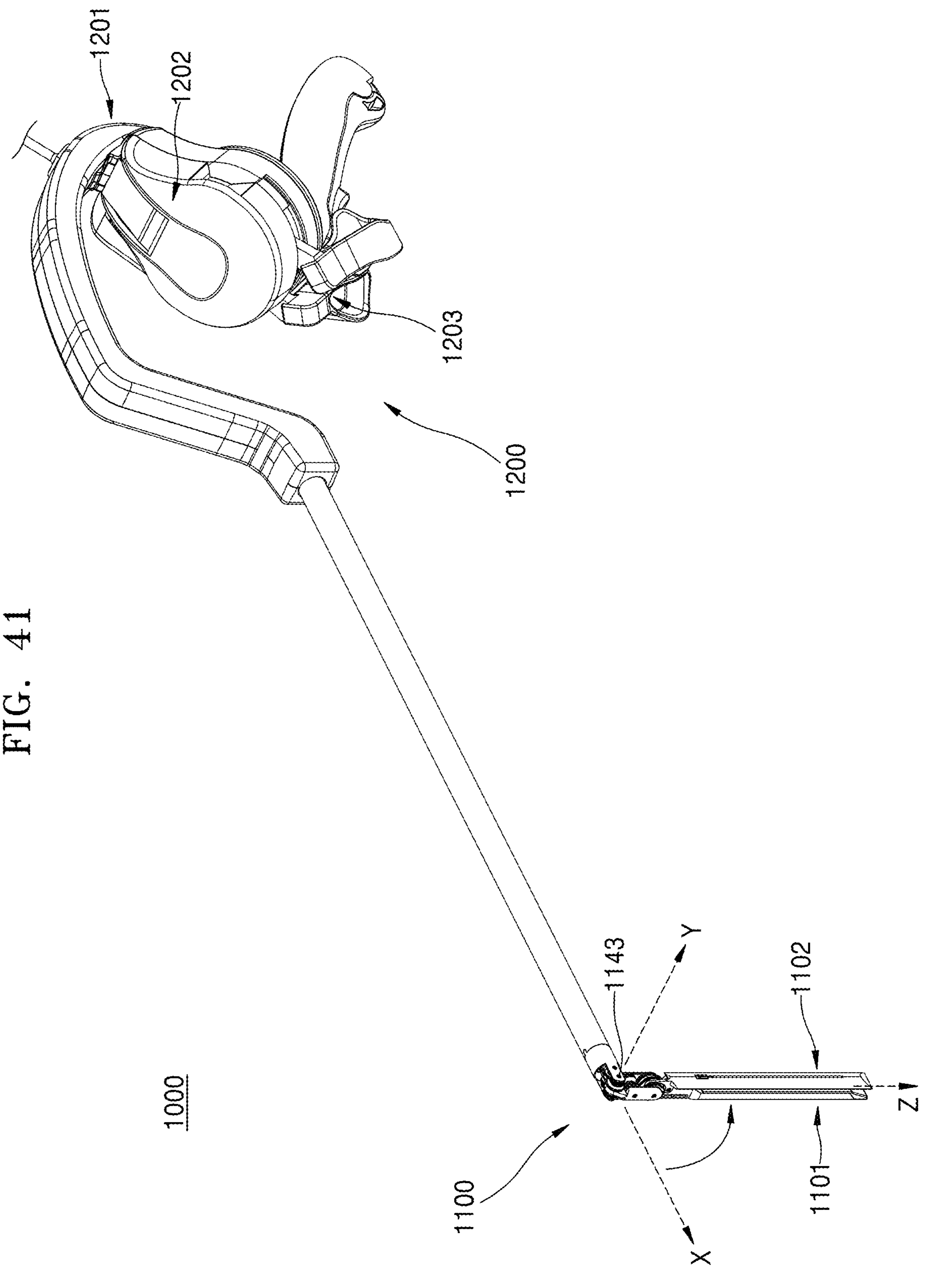

In detail, FIG. 38 is a diagram illustrating a state in which the jaws are pitch-rotated by −90°, and FIG. 39 is a diagram illustrating a process of performing an actuation motion in a state in which the jaws are pitch-rotated by −90°. FIG. 40 is a diagram illustrating a state in which the jaws are pitch-rotated by +90°, and FIG. 41 is a diagram illustrating a process of performing an actuation motion in a state in which the jaws are pitch-rotated by +90°.

Referring to FIGS. 38 to 41, it may be seen that, in performing a pitch motion, the motions of the manipulation part 1200 and the end tool 1100 intuitively match each other. That is, when the manipulation part 1200 rotates in a positive (+) direction with respect to the pitch rotation shaft (Y-axis), the end tool 1100 also rotates in the positive (+) direction with respect to the pitch rotation shaft (Y-axis). In addition, when the manipulation part 1200 rotates in a negative (−) direction with respect to the pitch rotation shaft (Y-axis), the end tool 1100 also rotates in the negative (−) direction with respect to the pitch rotation shaft (Y-axis). Here, the rotation angle of the manipulation part 1200 and the rotation angle of the end tool 1100 may be variously set according to the proportions of the pulleys.

FIGS. 42 to 45 are perspective views illustrating a yaw motion of the surgical instrument of FIG. 1.

Figure 42:
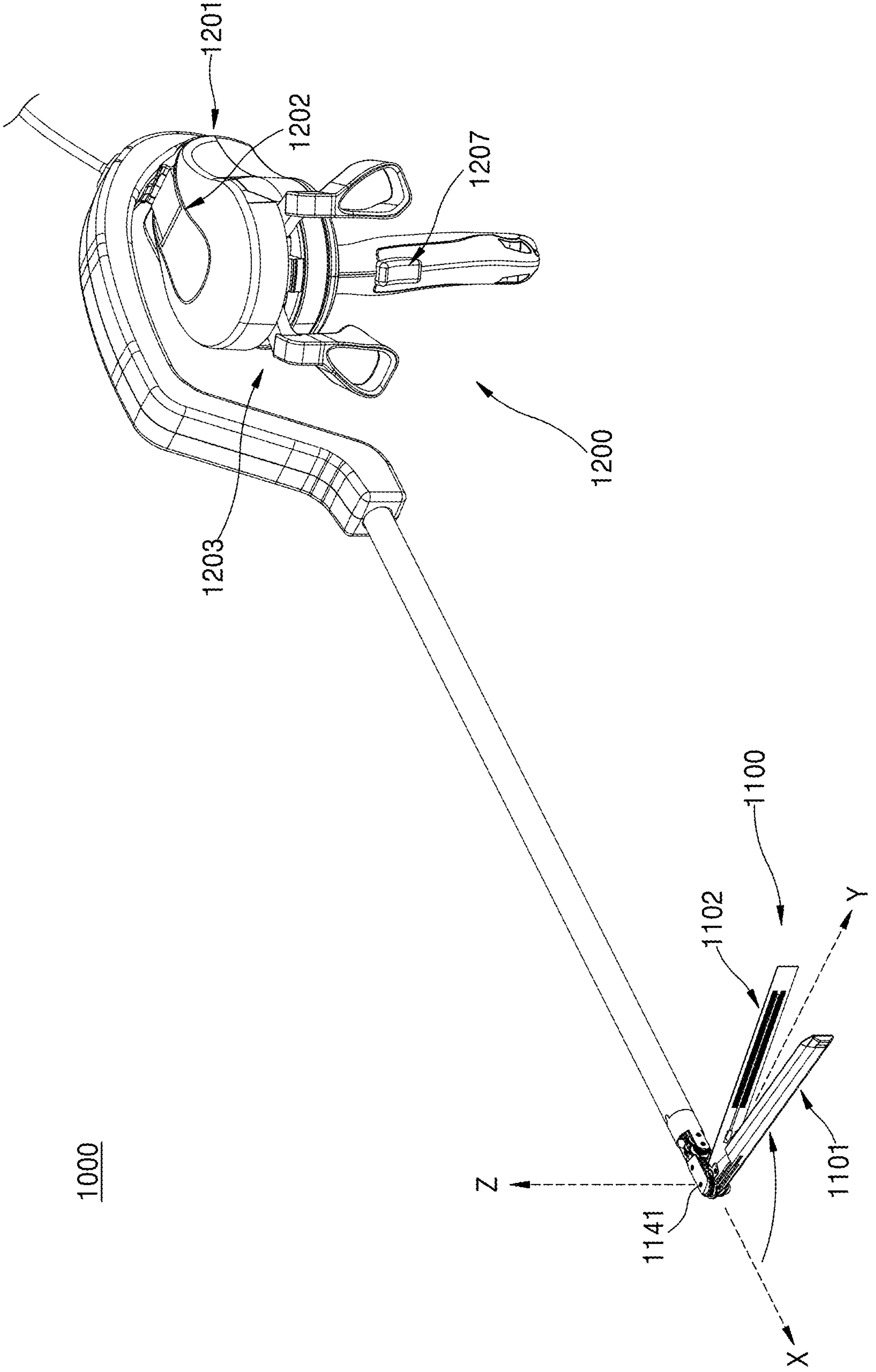
FIGS. 42 to 45 are perspective views illustrating a yaw motion of the surgical instrument of FIG. 1.
Figure 43:
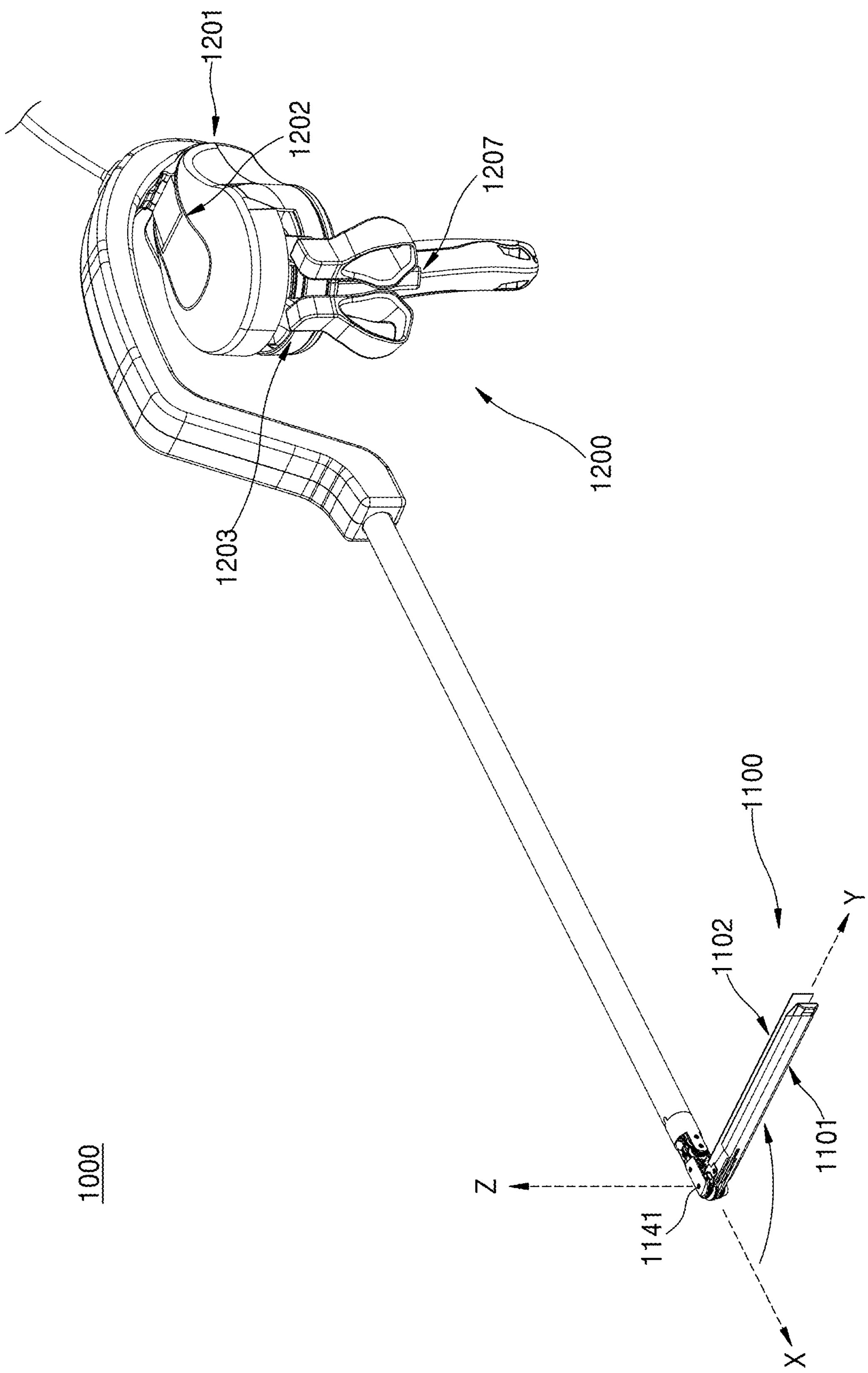
Figure 44:
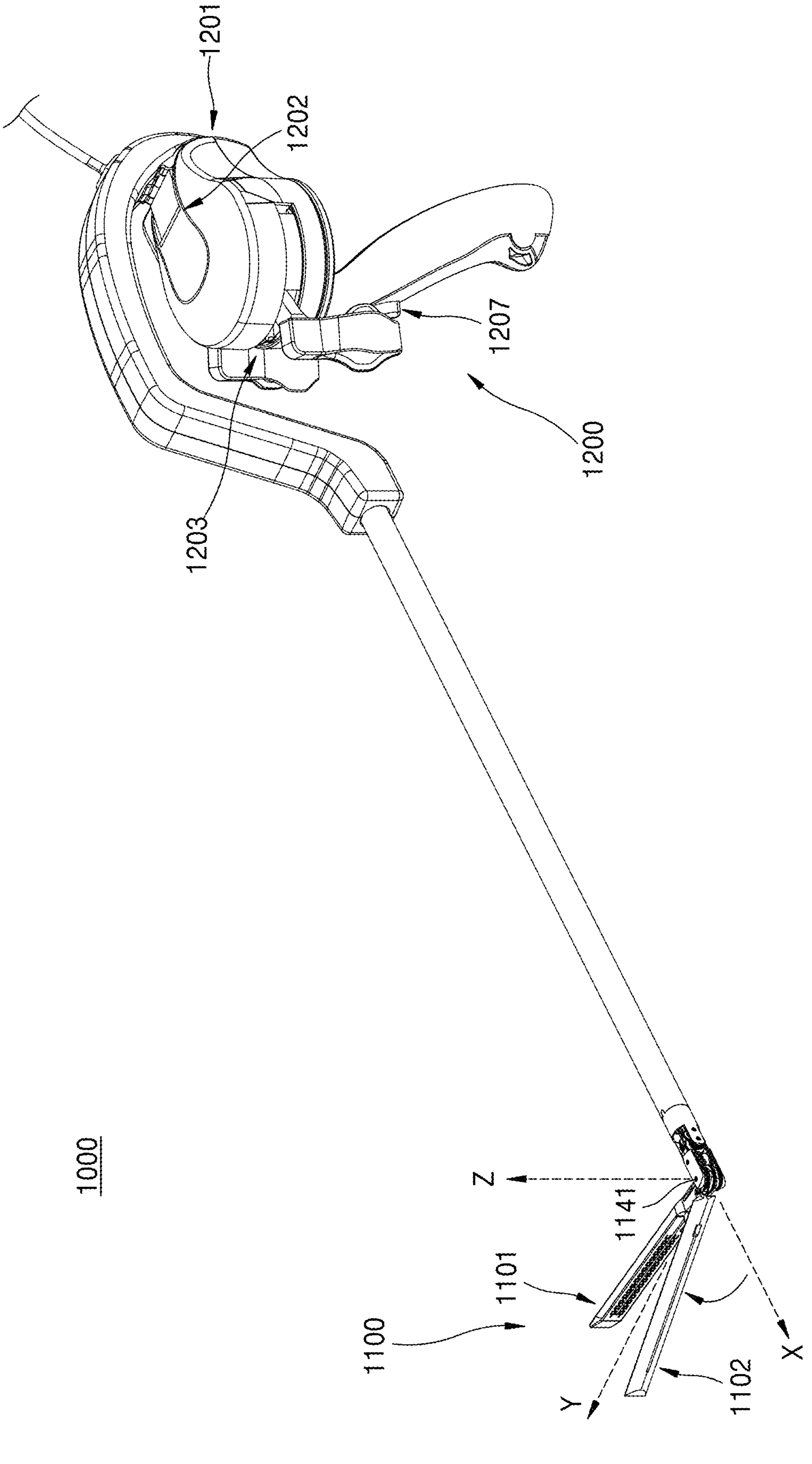
Figure 45:
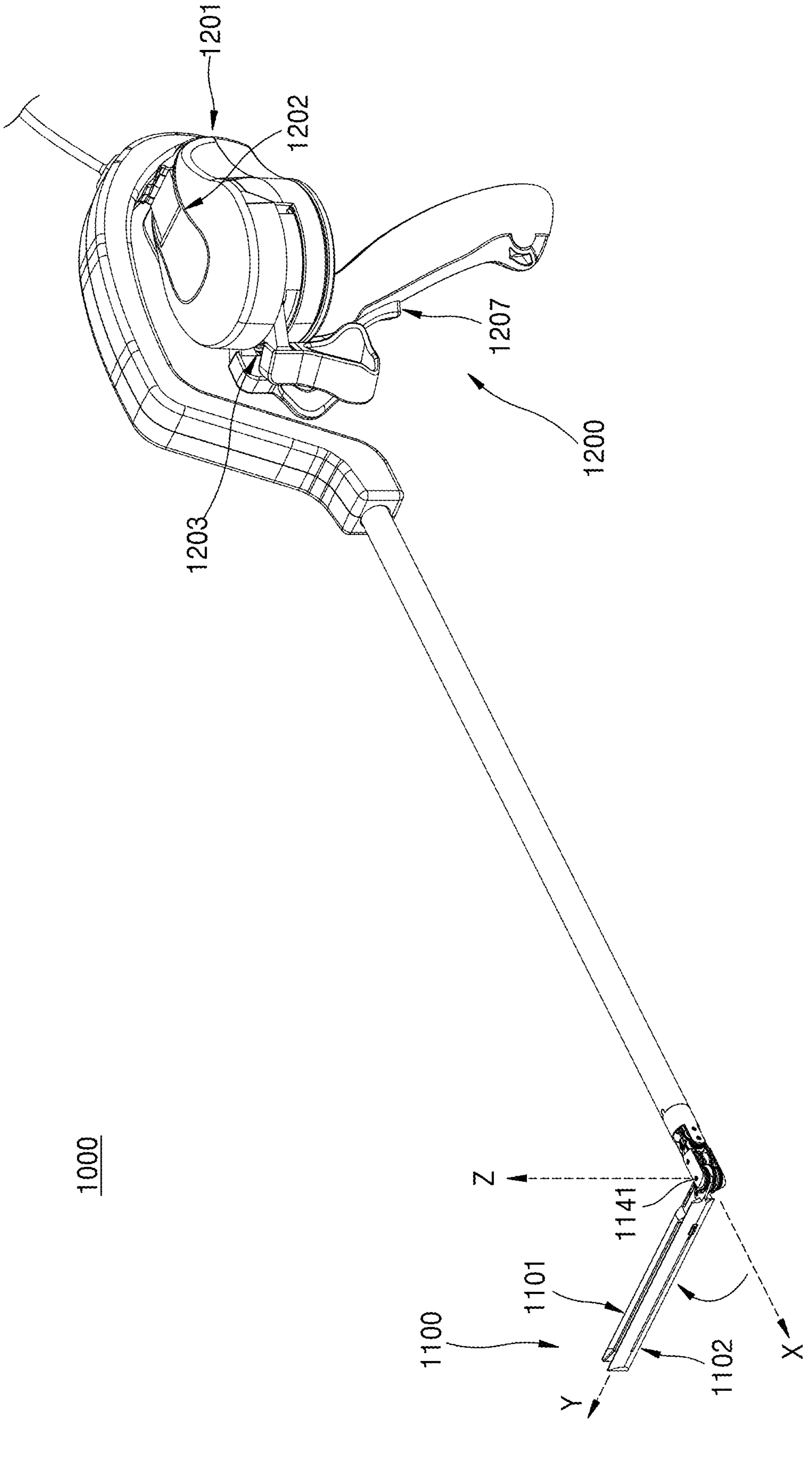

FIG. 42 is a diagram illustrating a state in which the jaws are yaw-rotated by +90°, and FIG. 43 is a diagram illustrating a process of performing an actuation motion in a state in which the jaws are yaw-rotated by +90°. FIG. 44 is a diagram illustrating a state in which the jaws are yaw-rotated by −90°, and FIG. 44 is a diagram illustrating a process of performing an actuation motion in a state in which the jaws are yaw-rotated by −90°.

Referring to FIGS. 42 to 45, it may be seen that, in performing a yaw motion, the motions of the manipulation part 1200 and the end tool 1100 intuitively match each other. That is, when the manipulation part 1200 rotates in a positive (+) direction with respect to the yaw rotation shaft (Z-axis), the end tool 1100 also rotates in the positive (+) direction with respect to the yaw rotation shaft (Z-axis). In addition, when the manipulation part 1200 rotates in a negative (−) direction with respect to the yaw rotation shaft (Z-axis), the end tool 1100 also rotates in the negative (−) direction with respect to the yaw rotation shaft (Z-axis). Here, the rotation angle of the manipulation part 1200 and the rotation angle of the end tool 1100 may be variously set according to the proportions of the pulleys.

FIGS. 46 to 49 are plan views illustrating a state in which the end tool for a surgical instrument of FIG. 1 is pitch-rotated and yaw-rotated.

Figure 46:
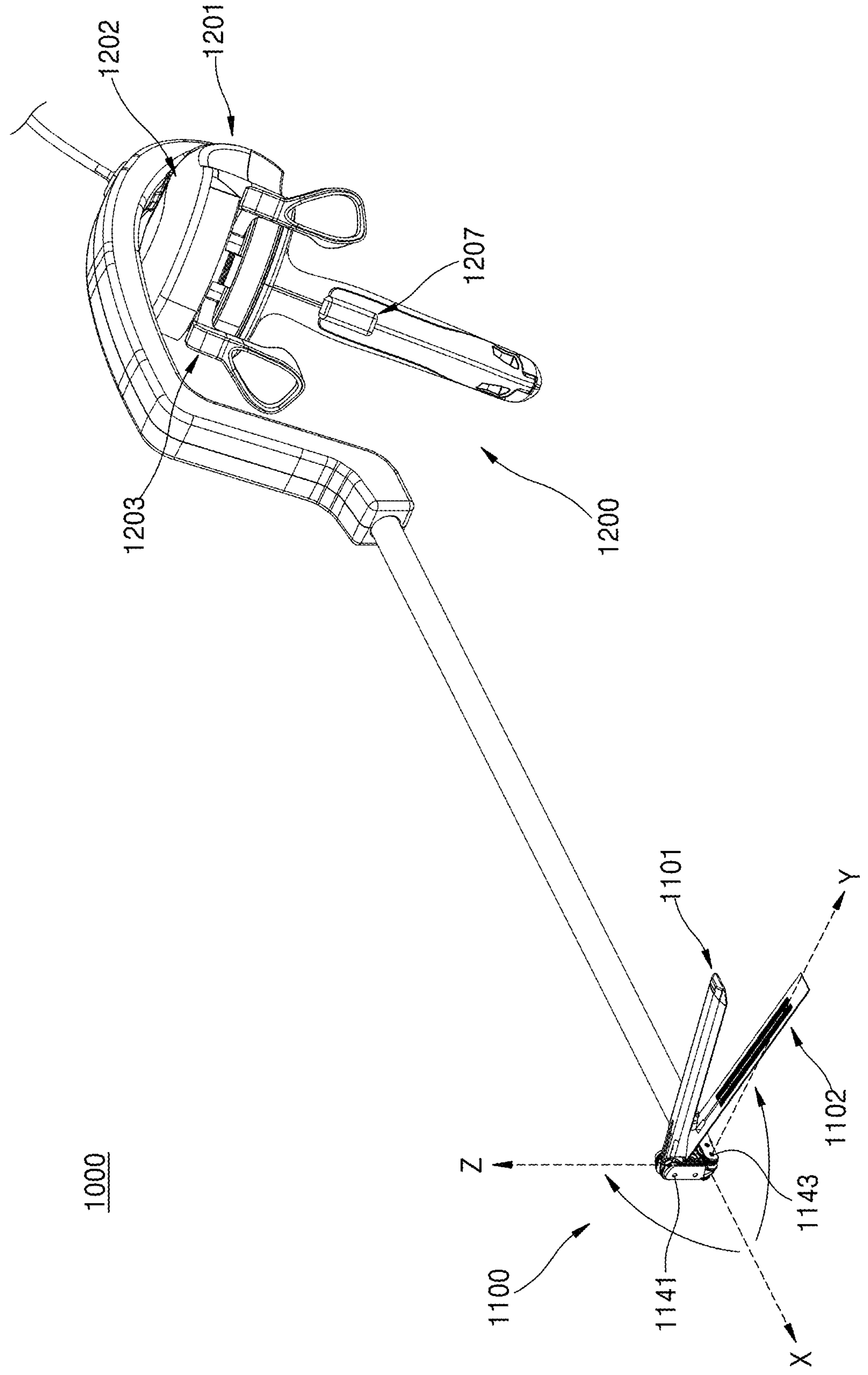
FIGS. 46 to 49 are plan views illustrating a state in which the end tool of the surgical instrument of FIG. 1 is pitch-rotated and yaw-rotated.
Figure 47:
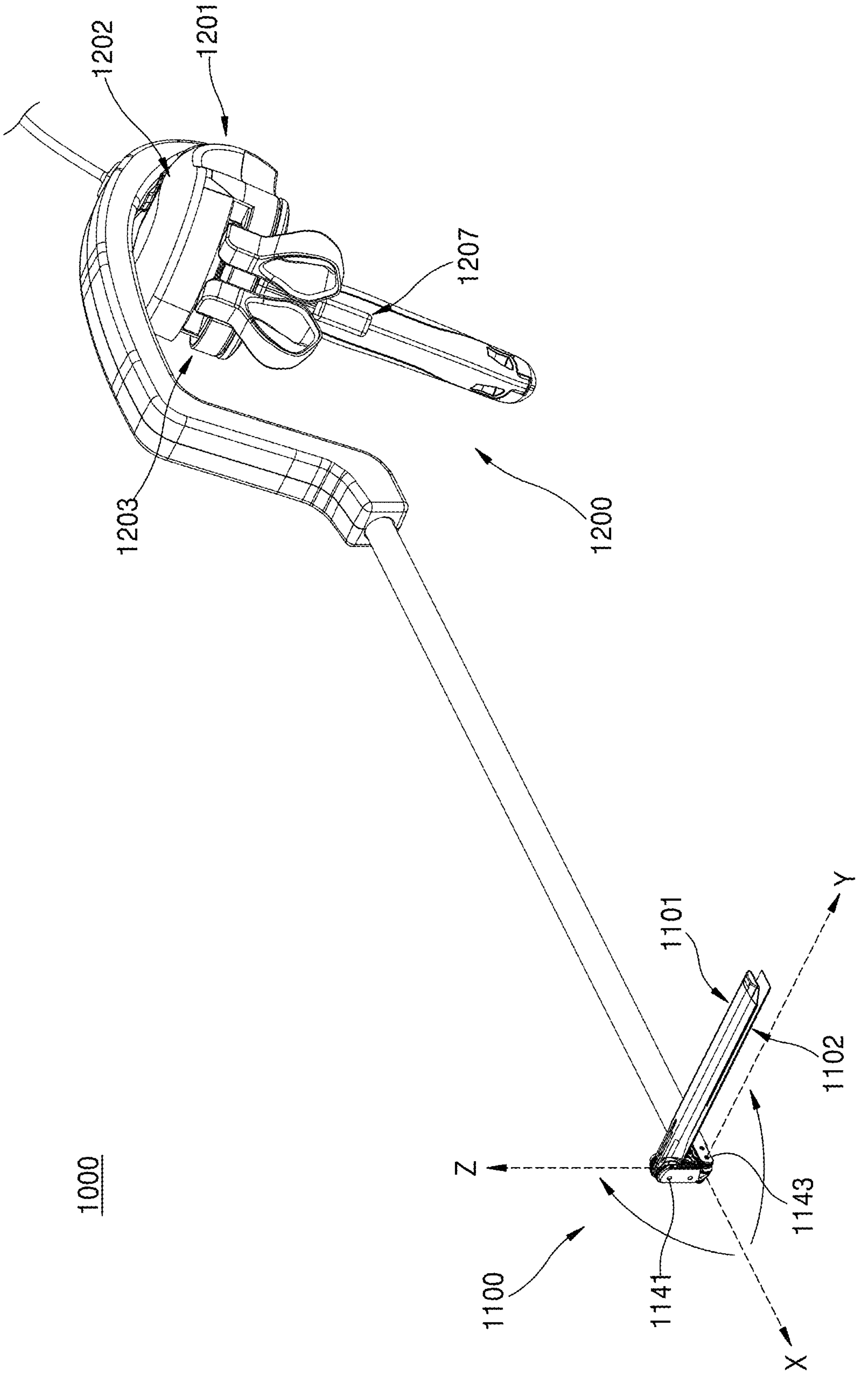
Figure 48:
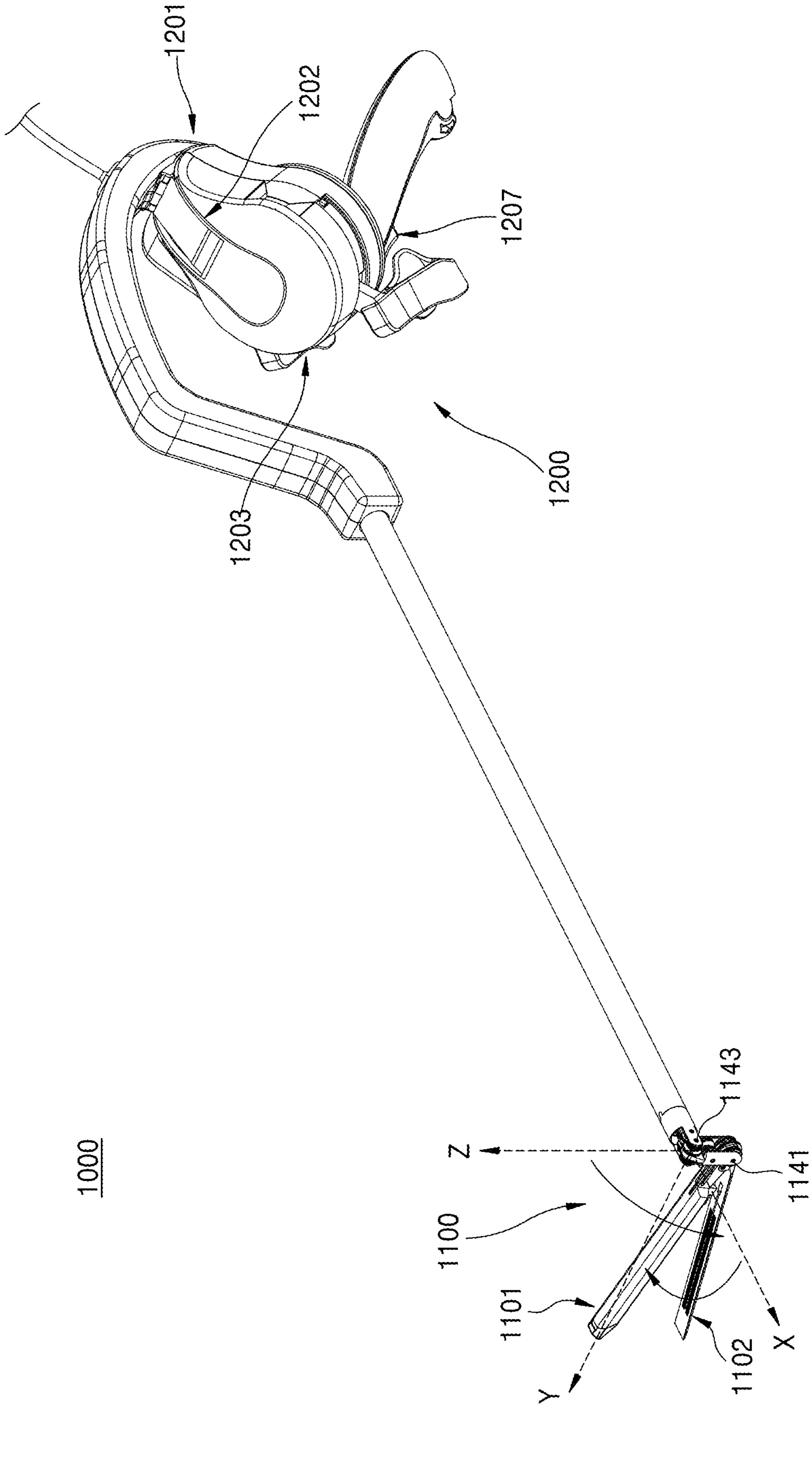
Figure 49:
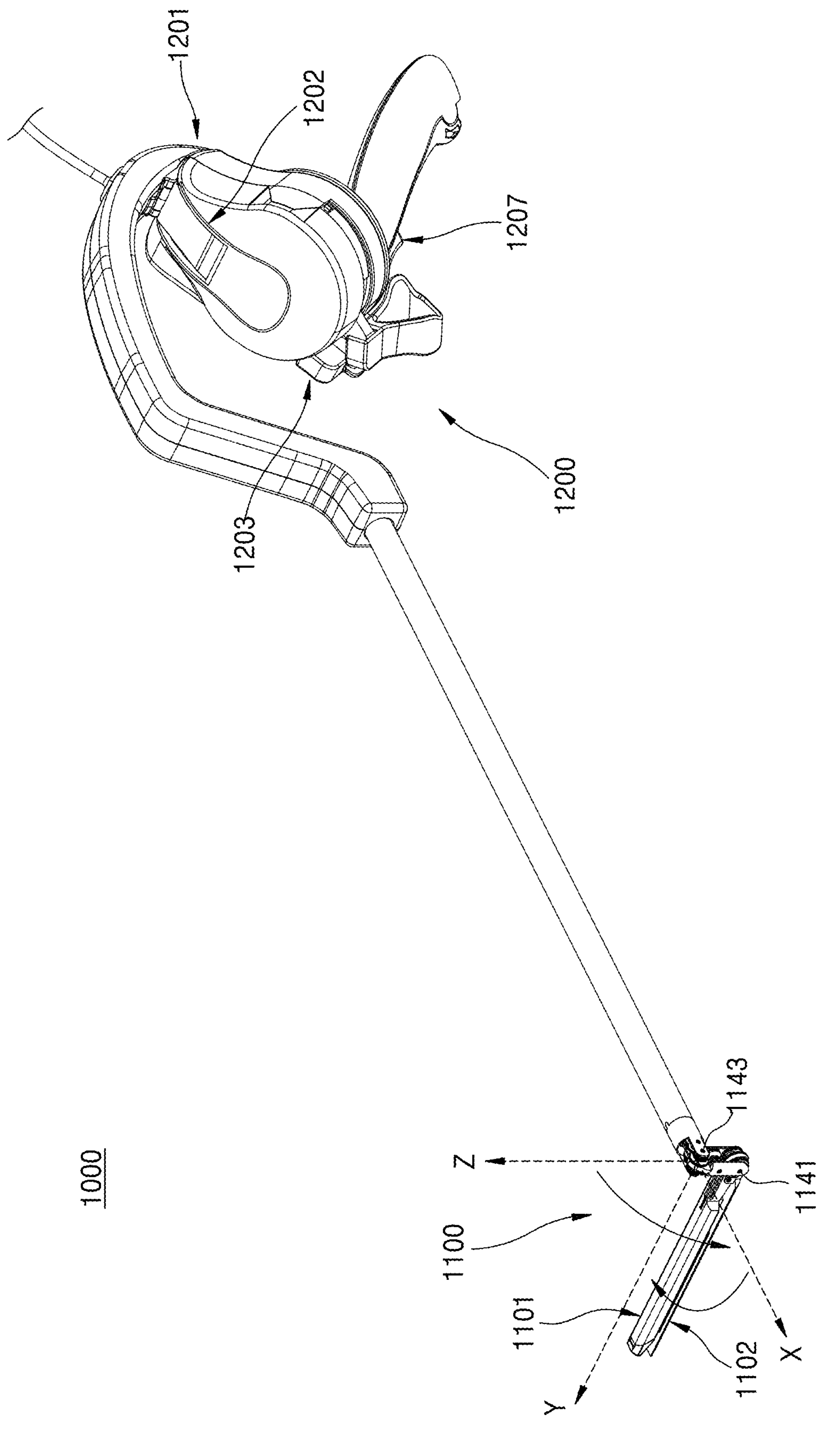

FIG. 46 is a diagram illustrating a state in which the jaws are pitch-rotated by −90° and simultaneously yaw-rotated by +90°, and FIG. 47 is a diagram illustrating a process of performing an actuation motion in a state in which the jaws are pitch-rotated by −90° and simultaneously yaw-rotated by +90°. FIG. 48 is a diagram illustrating a state in which the jaws are pitch-rotated by +90° and simultaneously yaw-rotated by −90°, and FIG. 49 is a diagram illustrating a process of performing an actuation motion in a state in which the jaws are pitch-rotated by +90° and simultaneously yaw-rotated by −90°.

Referring to FIGS. 46 to 49, it may be seen that the motions of the manipulation part 1200 and the end tool 1100 intuitively match each other even when simultaneously performing a pitch motion and a yaw motion.

Figure 22:
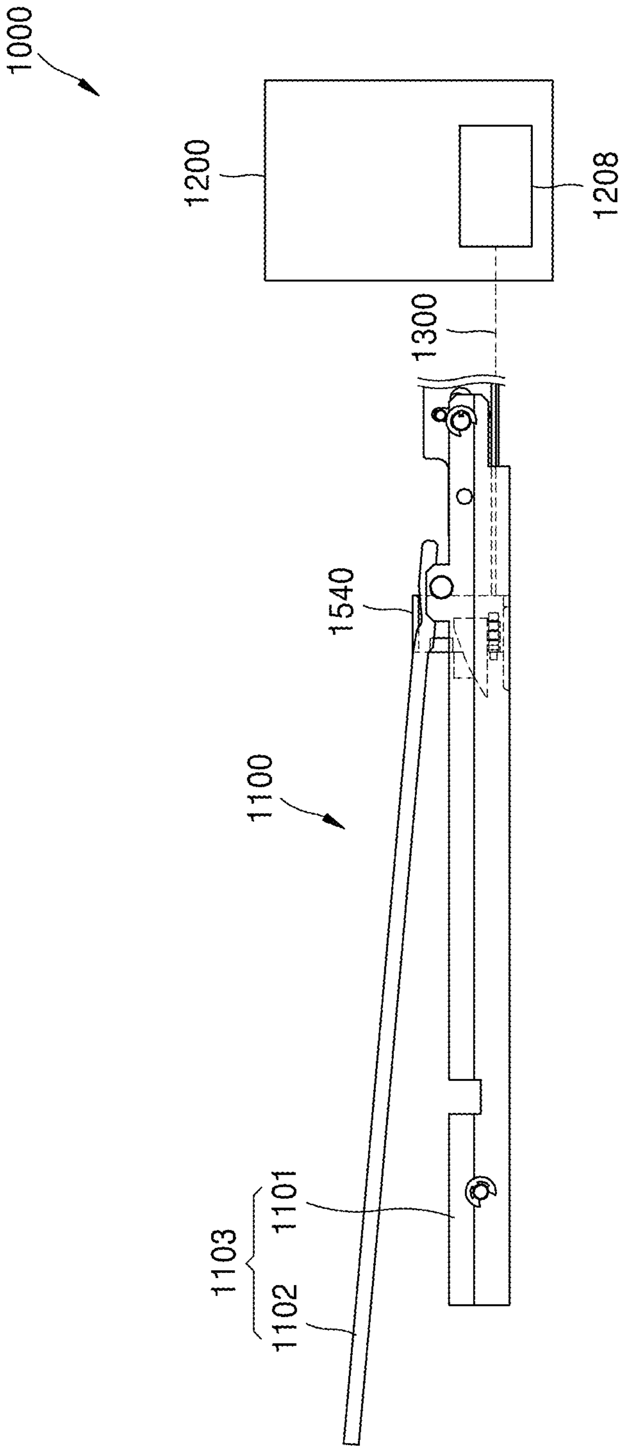
FIG. 22 is a diagram schematically illustrating a surgical instrument according to an embodiment of the present disclosure.
Figure 23:
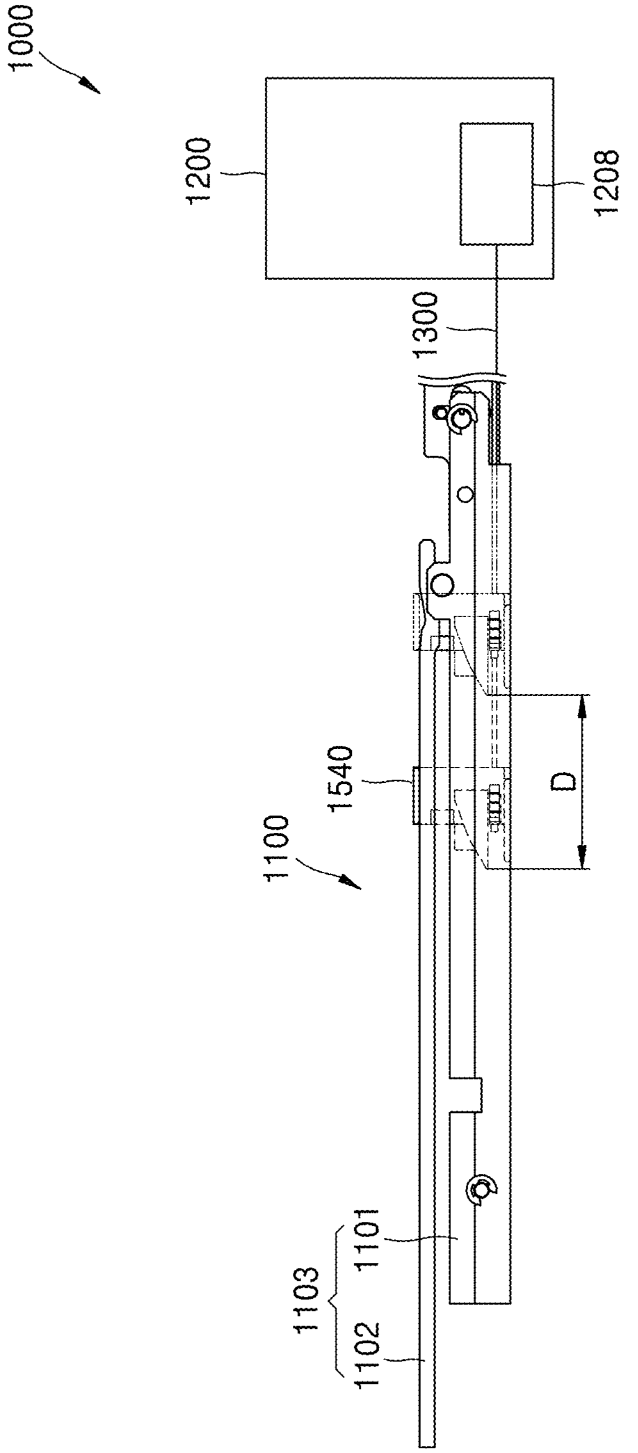
FIG. 23 is a diagram for describing a motion of a working member of the surgical instrument of FIG. 22.
Figure 24:
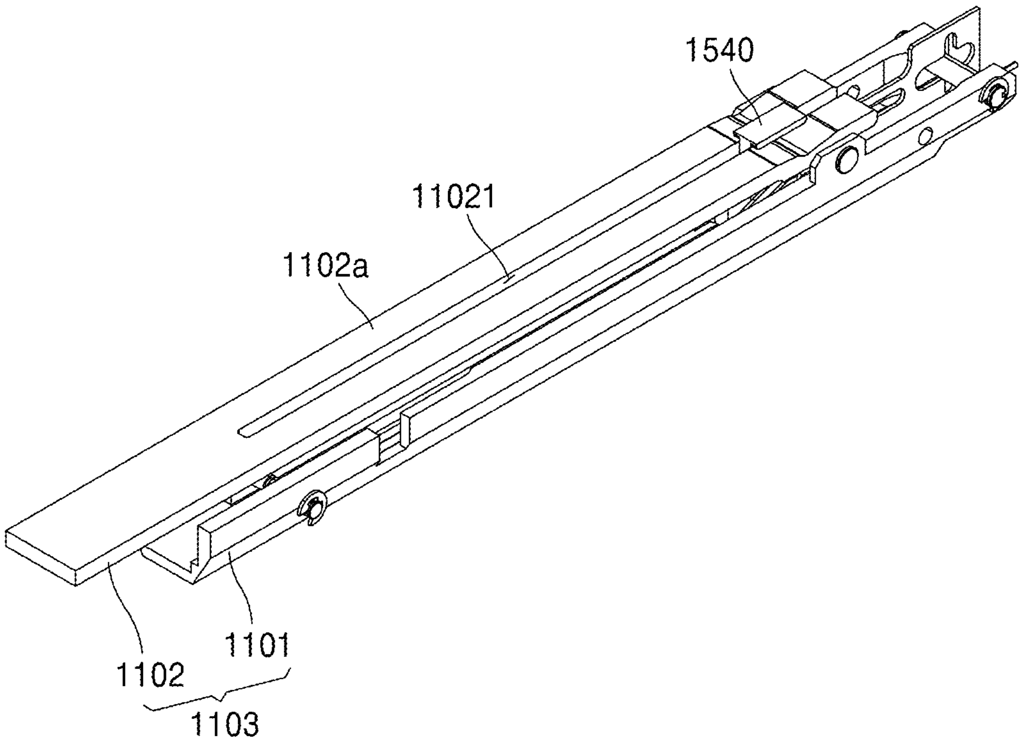
FIG. 24 is a perspective view illustrating a jaw of FIG. 22.
Figure 25:
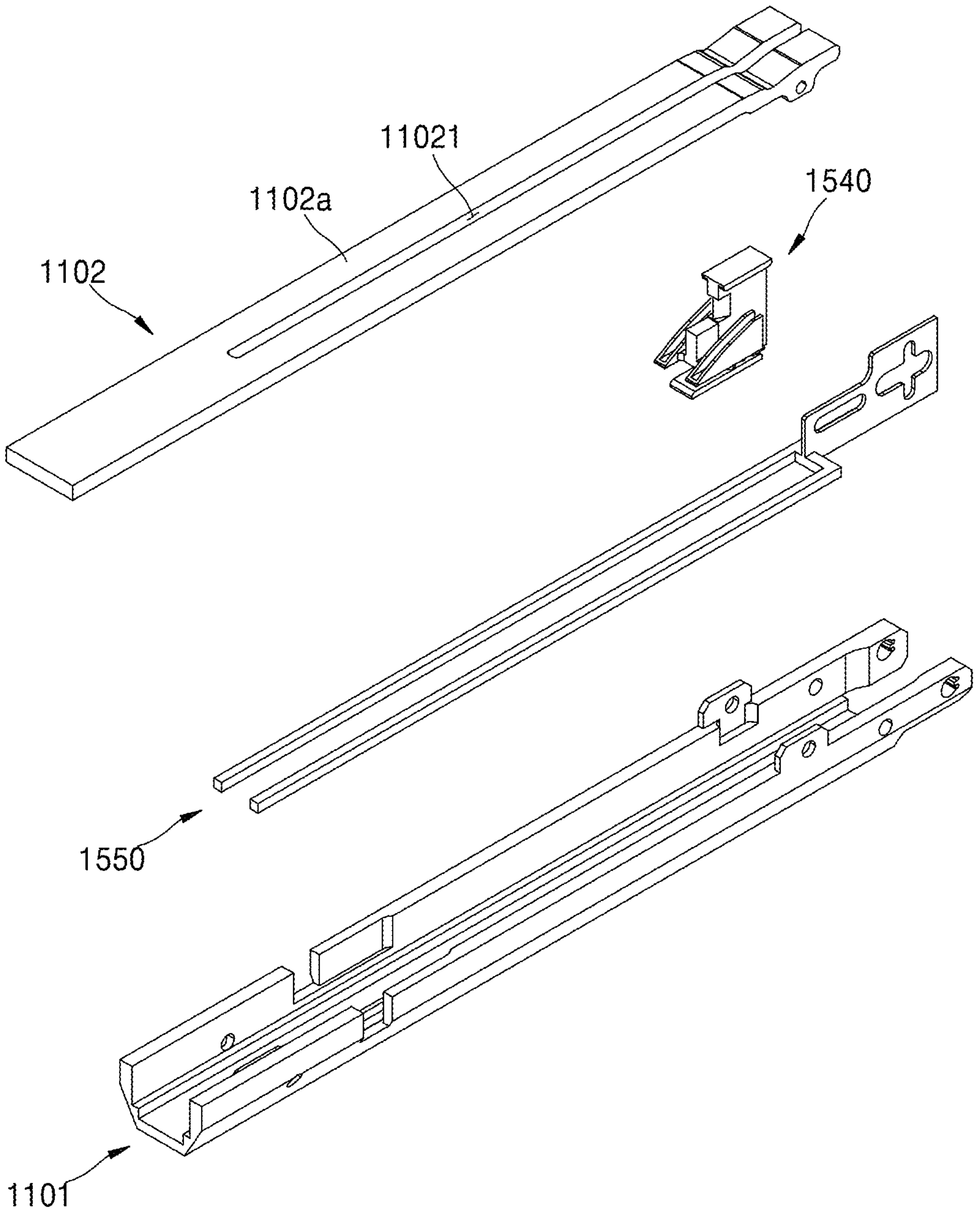
FIG. 25 is an exploded perspective view illustrating components of the jaw of FIG. 22.
Figure 26:
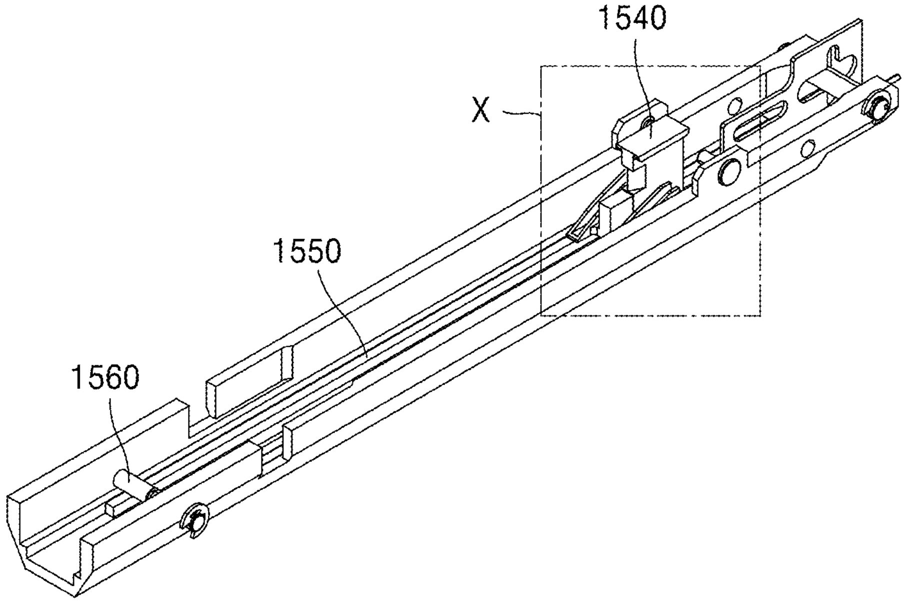
FIG. 26 is a diagram with a second jaw omitted from FIG. 24.
Figure 27:
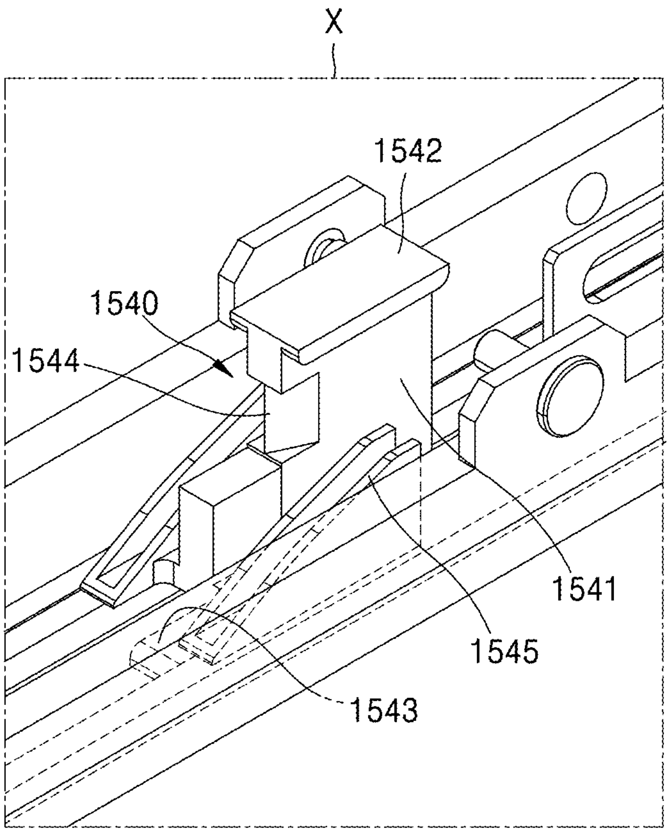
FIG. 27 is an enlarged view of portion X of FIG. 26.
Figure 28:
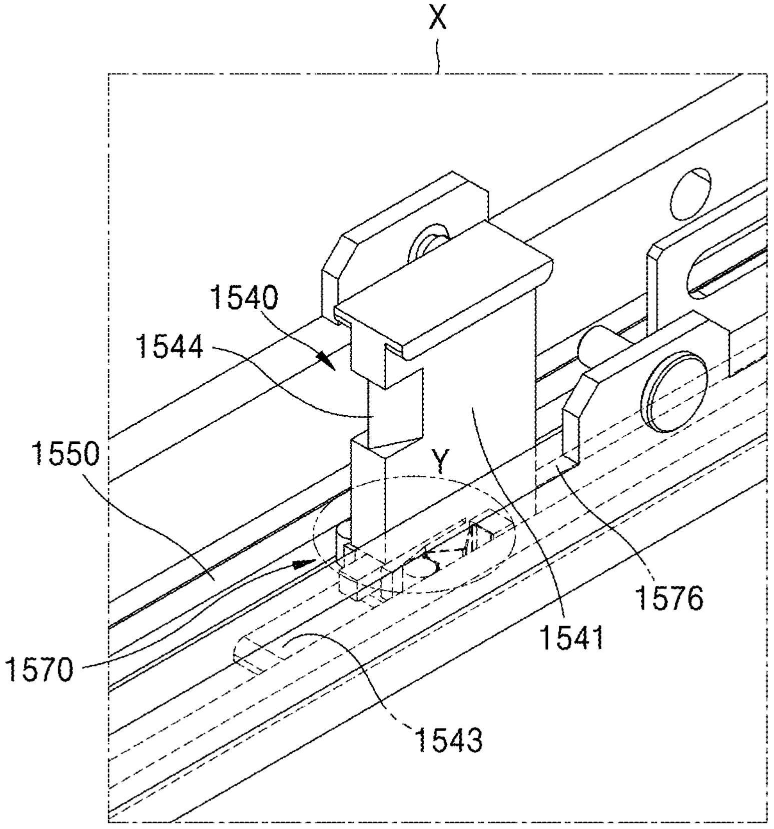
FIG. 28 is a diagram with a wedge omitted from FIG. 27.
Figure 29:
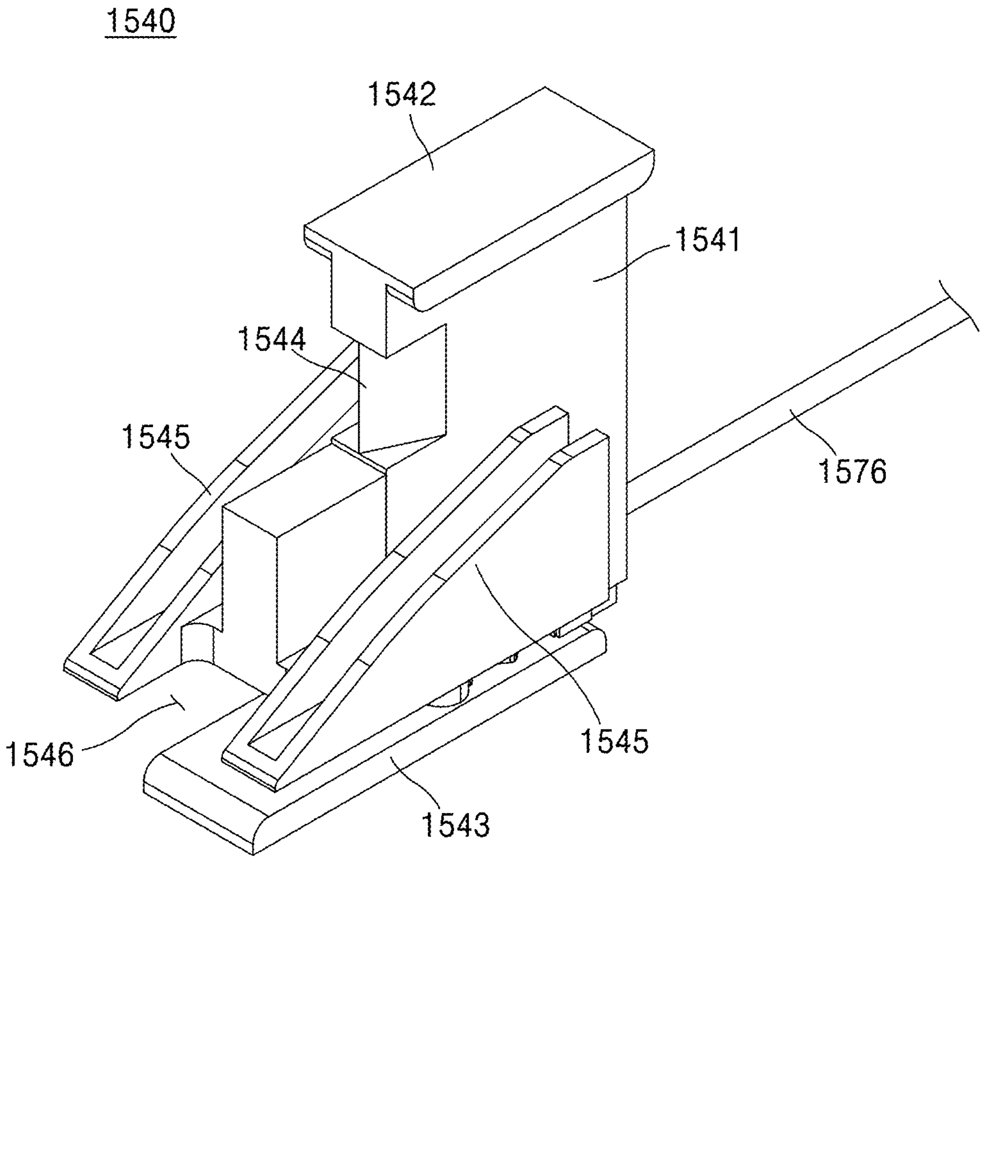
FIG. 29 is a perspective view illustrating a working member of FIG. 25.
Figure 30:
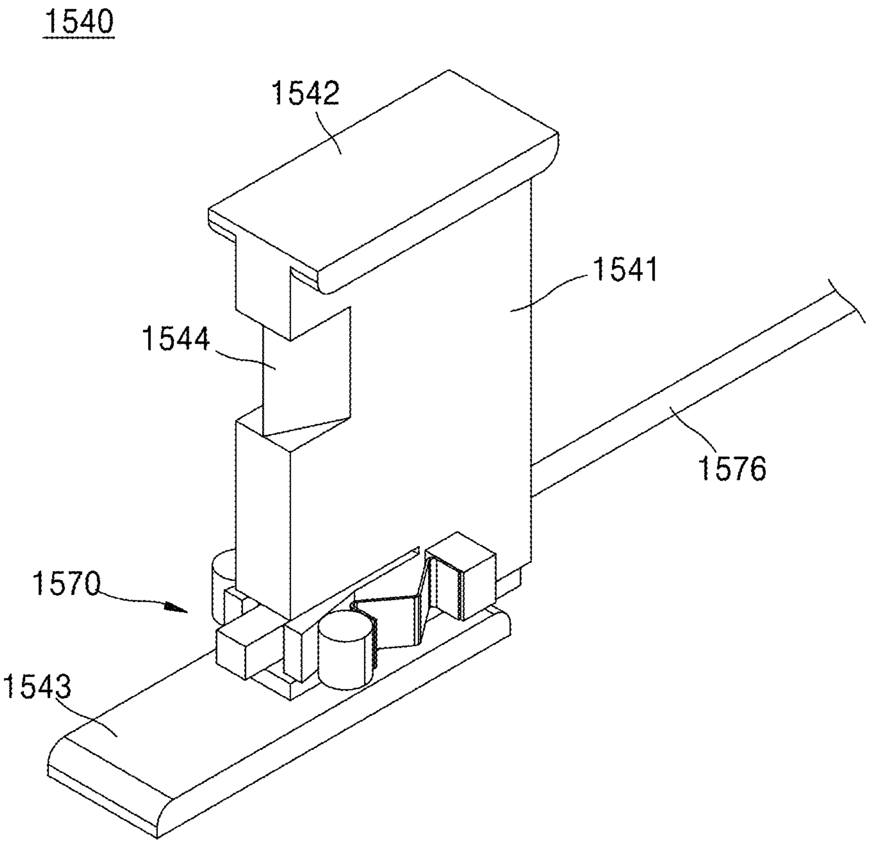
FIG. 30 is a diagram with a wedge omitted from FIG. 29.

FIG. 22 is a diagram schematically illustrating the surgical instrument 1000 according to an embodiment of the present disclosure, and FIG. 23 is a diagram illustrating a motion of the working member 1540 of the surgical instrument 1000 of FIG. 22. FIG. 24 is a perspective view illustrating the jaws 1103 of FIG. 22, FIG. 25 is an exploded perspective view illustrating components of the jaws 1103 of FIG. 22, and FIG. 26 is a diagram with the second jaw 1102 omitted from FIG. 24. FIG. 27 is an enlarged view of portion X of FIG. 26, and FIG. 28 is a diagram with the wedge 1545 omitted from FIG. 27. FIG. 29 is a perspective view illustrating the working member 1540 of FIG. 25, and FIG. 30 is a diagram with the wedge 1545 omitted from FIG. 29.

First, referring to FIGS. 22 and 23, the surgical instrument 1000 according to an embodiment of the present disclosure may include the end tool 1100. The end tool 1100 may be manipulated through a manipulation part.

The end tool 1100 may be arranged on one side of the surgical instrument 1000 and inserted into a surgical site to perform a motion necessary for surgery. For example, the end tool 1100 may be configured to rotate in at least one direction.

The end tool 1100 may perform functions such as a surgical clamp, a grasper, a vessel sealer, or a stapler, but the present disclosure is not limited thereto, and any tool may be used as an end tool 1100 as long as it may be inserted into a patient's surgical site and perform a motion necessary for surgery.

Hereinafter, for convenience of description, an embodiment in which the end tool 1100 is used as a stapler will be mainly described.

The end tool 1100 may be connected to the manipulation part through the connection part 1400. As described above, one or more wires and electric wires may be accommodated in the connection part 1400. Accordingly, when the user manipulates the manipulation part, the end tool 1100 may be moved by the manipulation by the user.

The end tool 1100 may include the jaws 1103.

The jaws 1103 may have various shapes. For example, at least one jaw 1103 may be configured to form a set. As a preferred example, the jaws 1103 may be configured as a pair of jaws 1103 including the first jaw 1101 and the second jaw 1102.

Depending on the function of the end tool 1100, the first jaw 1101 and the second jaw 1102 may be formed in the same shape or may be formed in different shapes.

The first jaw 1101 and the second jaw 1102 may be arranged to face each other. For example, the first jaw 1101 and the second jaw 1102 may be connected to each other in one area so as to be rotatable.

At least one of the first jaw 1101 and the second jaw 1102 may be rotatable. In detail, referring to FIGS. 22 and 23, the second jaw 1102 may be rotatable with respect to the first jaw 1101. In other words, the first jaw 1101 and the second jaw 1102 may be connected to each other in one area by a rotation shaft, and the second jaw 1102 may rotate around the rotation shaft with respect to the first jaw 1101 in a direction in which the jaws are opened or closed. Through such a rotational motion, the first jaw 1101 and the second jaw 1102 may perform a grip motion or a clamping motion.

The first jaw 1101 may be formed to extend to have a length. For example, the first jaw 1101 may be formed in the shape of an elongated bar such that its length is greater than its width.

The cartridge accommodation part 1101*a* (see FIG. 15) may be provided inside the first jaw 1101. The cartridge 1500 may be accommodated in the cartridge accommodation part 1101*a* (see FIG. 15). The cartridge accommodation part 1101*a* (see FIG. 15) may have one surface open, for example, the surface thereof facing the second jaw 1102 may be open. In addition, the working member 1540 may be arranged in the cartridge accommodation part 1101*a* (see FIG. 15).

The working member 1540 may move while accommodated in the cartridge accommodation part 1101*a* (see FIG. 15). For example, the working member 1540 may move in the lengthwise direction of the jaws 1103 while accommodated in the cartridge accommodation part 1101*a* (see FIG. 15).

The second jaw 1102 may be formed to extend to have a length. For example, the second jaw 1102 may be formed in the shape of an elongated bar such that its length is greater than its width.

The working member 1540 may move in the lengthwise direction of the jaws 1103 in a state in which the first jaw 1101 and the second jaw 1102 are closed (the first jaw 1101 and the second jaw 1102 face each other). In other words, the working member 1540 may be accommodated in the first jaw 1101 such that one side thereof is connected to the first jaw 1101 and the other side is connected to the second jaw 1102. Thus, the working member 1540 may apply a force so that the first jaw 1101 and the second jaw 1102 are closed, while moving from the proximal ends of the jaws 1103 toward the distal ends of the jaws 1103. Thereafter, after the first jaw 1101 and the second jaw 1102 are closed, the working member 1540 may move in the lengthwise direction of the first jaw 1101 and the second jaw 1102, specifically, toward the distal ends of the first jaw 1101 and the second jaw 1102. In other words, the working member 1540 may apply a force such that the first jaw 1101 and the second jaw 1102 perform a clamping motion, while moving from the proximal ends of the jaws 1103 toward the distal ends of the jaws 1103.

In an embodiment, the anvil 1102*a* may be formed on one surface of the second jaw 1102. For example, the second jaw 1102 may have an anvil 1002*a* formed on a portion of the second jaw 1102 that faces the first jaw 1101 (a portion that faces the staples accommodated in the first jaw 1101).

As the working member 1540 moves, the end tool 1100 for a surgical instrument may perform one or more motions. For example, as the working member 1540 moves, staples (not shown) accommodated in the first jaw 1101 may be released toward the second jaw 1102 to perform stapling.

Referring again to FIGS. 22 and 23, the working member 1540 may begin to move in the state illustrated in FIG. 22, so as to apply a force to the jaws 1103 in the direction in which the first jaw 1101 and the second jaw 1102 are closed. Thereafter, a linear motion may be performed for a certain distance D in the state illustrated in FIG. 23. For example, the working member 1540 may move forward and/or backward in the lengthwise direction of the jaws 1103.

As such, as the working member 1540 moves, the wedge 1545 formed on the working member 1540 may push up the staple or the release member 1535, thereby implementing a stapling motion of the end tool 1100, as will be described below.

The working member 1540 may receive a driving force for a movement through the moving member 1550 (see FIG. 25). For example, the moving member 1550 may be formed to move linearly in one or two directions.

The moving member 1550 may be arranged in one area of the end tool 1100 and, for example, may be arranged to be at least partially accommodated in the first jaw 1101.

The moving member 1550 may be moved by various power sources, for example, by the driving part 1208. The driving part 1208 is a power source and may be implemented in various manners, such as a motor or an actuator.

The driving part 1208 may be arranged in one area of the manipulation part. In addition, in another alternative embodiment, the driving part 1208 may be arranged in another area of the surgical instrument 1000, for example, an area of the end tool 1100 or an area of the connection part 1400 connecting the end tool 1100 to the manipulation part, or may be arranged in an area outside the surgical instrument 1000.

The driving part 1208 and the moving member 1550 may be connected to one or more power transmission parts 1300, and a driving force of the driving part 1208, for example, a rotational force, may be transmitted to the moving member 1550 through the power transmission part 1300. As a specific example, the power transmission part 1300 may include one or more wires.

The rotational force of the driving part 1208 may be transmitted to the moving member 1550 through the power transmission part 1300 including one or more wires. In an alternative embodiment, the driving part 1208 may be connected to the power transmission part 1300 through one or more pulleys.

Referring to FIGS. 24 to 30, the working member 1540 may move in the lengthwise direction of the pair of jaws 1103. In addition, the end tool 1100 may further include the moving member 1550 for moving the working member 1540.

The moving member 1550 may be formed to extend to have a length corresponding to the movement direction of the working member 1540. In other words, the moving member 1550 may be formed to extend in the lengthwise direction of the pair of jaws 1103.

In addition, the moving member 1550 may move linearly in the lengthwise direction. The moving member 1550 may transmit power for moving the working member 1540 to the working member 1540, while moving linearly. In detail, as described above, the moving member 1550 may receive power generated by the driving part 1208 through the power transmission part 1300, and be linearly moved by the received power. Here, the moving member 1550 may selectively move the working member 1540 while moving linearly. Here, that the moving member 1550 selectively moves the working member 1540 may mean that the working member 1540 and the moving member 1550 may or may not be connected to each other to be moved together by a clutch assembly 1570 as will be described below.

In an alternative embodiment, the moving member 1550 may be formed to surround at least two surfaces of the working member 1540. As a specific example, the moving member 1550 may have two parts formed to extend to have lengths parallel to each other, and the working member 1540 may be arranged therebetween. In other words, the moving member 1550 may be in simultaneous contact with both sides of the working member 1540, as will be described below.

A backward wire 1576 may be connected to one side of the working member 1540. For example, the backward wire 1576 may be connected to the rear surface (proximal end) of the working member 1540.

The backward wire 1576 may transmit, to the working member 1540, power for moving the working member 1540 backward. That is, a backward motion of the working member 1540 may be performed through the backward wire 1576. In other words, a backward motion of the working member 1540 through the backward wire 1576 may be performed by pulling the working member 1540 through the backward wire 1576.

Although not illustrated, the driving part 1208 or a driving transmission part (e.g., a wire or a pulley) for pulling the backward wire 1576 may be connected to the backward wire 1576, and the backward wire 1576 may be moved through manual or automatic manipulation.

The working member 1540 may include a body part 1541 and at least one flange.

The body part 1541 is a member that forms the entire exterior of the working member 1540. The body part 1541 may be formed in the shape of an approximately long rectangular shape.

The flanges may be formed at both ends of the body part 1541 to prevent the working member 1540 from separating from the jaws 1103.

The working member 1540 may include a first flange 1542.

The first flange 1542 may be arranged on one side of the body part 1541, and may be formed to have a width greater than that of the body part 1541. In other words, when the working member 1540 is viewed from the distal ends of the jaws 1103 toward the proximal ends, the first flange 1542 may be formed to be wider than the body part 1541 in the horizontal direction.

The first flange 1542 may serve to prevent the working member 1540 from being separated from the jaws 1103 when the working member 1540 moves along the jaws 1103.

In detail, the second jaw 1102 may include a second slit 11021 formed to extend in the lengthwise direction of the second jaw 1102. Here, the working member 1540 may move in a state in which at least a portion of the body part 1541 is accommodated in the second slit 11021. In this case, the first flange 1542 may be arranged above the second jaw 1102, and the body part 1541 may be arranged to pass through the second slit 11021 from the second jaw 1102. In other words, the first flange 1542 may be hung on the upper surface of the second jaw 1102, and the body part 1541 may extend from the first flange 1542 in a direction passing through the second slit 11021.

The working member 1540 may include a second flange 1543.

The second flange 1543 may be arranged on the other side of the body part 1541. That is, the second flange 1543 may be arranged opposite to the first flange 1542 with respect to the body part 1541. The second flange 1543 may be formed to have a width greater than that of the body part 1541. In other words, when the working member 1540 is viewed from the distal ends of the jaws 1103 toward the proximal ends, the second flange 1543 may be formed to be wider than the body part 1541 in the horizontal direction.

The second flange 1543 may serve to prevent the working member 1540 from being separated from the jaws 1103 when the working member 1540 moves along the jaws 1103.

In detail, the first jaw 1101 may include the first slit 1512 formed to extend in the lengthwise direction of the first jaw 1101. Here, the working member 1540 may move in a state in which at least a portion of the body part 1541 is accommodated in the first slit 1512. In this case, the second flange 1543 may be arranged below the first jaw 1101, and the body part 1541 may be arranged to pass through the first slit 1512 from the first jaw 1101. In other words, the second flange 1543 may be hung on the lower surface of the first jaw 1101, and the body part 1541 may extend from the second flange 1543 in a direction passing through the first slit 1512.

When the working member 1540 moves in the lengthwise direction of the jaws 1103, at least a portion of the first flange 1542 may be in contact with the second jaw 1102, and the other portions may be in contact with the second jaw 1102. For example, this means that, when the working member 1540 moves in the lengthwise direction of the jaws 1103, the entire area of the first flange 1542 is not in contact with the second jaw 1102.

In addition, when the working member 1540 moves in the lengthwise direction of the jaws 1103, at least a portion of the second flange 1543 may be in contact with the first jaw 1101, and the other portions may be in contact with the first jaw 1101. For example, this means that, when the working member 1540 moves in the lengthwise direction of the jaws 1103, the entire area of the second flange 1543 is not in contact with the first jaw 1101.

In other words, the working member may be rotatable in at least one direction while moving along the jaw. That is, this does not mean that the first flange and the second flange does not move while in close contact with the jaw, but means that portions of the first flange and the second flange may be in contact with the first jaw and the second jaw and the other portions may not be in contact with the first jaw and the second jaw. In other words, this mean that the distance between the first flange and the second flange has a value greater than the vertical distance between the lowermost end surface of the first jaw and the uppermost end surface of the second jaw in a state in which the first jaw and the second jaw are closed.

That is, this means that, when the working member 1540 is connected to the first jaw 1101 and the second jaw 1102, the first jaw 1101 and the second flange 1543, and/or the second jaw 1102 and the first flange 1542 are spaced apart from each other by a certain distance, such that the working member 1540 is rotatable.

Thus, when the working member 1540 linearly moves in the lengthwise direction of the jaws 1103, the working member 1540 may receive little resistance from the first jaw 1101 and the second jaw 1102, and thus easily move.

The working member 1540 may further include the wedge 1545.

The wedge 1545 may be formed integrally with at least one side of the body part 1541, or may be coupled to the body part 1541 as a separate member.

The wedge 1545 may be formed to have a certain inclined surface. That is, the wedge 1545 may be formed to be inclined to a certain extent in the extension direction of the connection part 1400. In other words, the height of the proximal end of the cartridge may be greater than that of the distal end. The wedge 1545 may be formed in various numbers and shapes depending on the shape of the staple or the release member 1535 in contact therewith.

As such, the wedge 1545 may be formed to be in sequential contact with the release member 1535 or a plurality of staples, to serve to sequentially push up the staples. As illustrated in FIG. 21 and the like to be described below, the working member 1540 may serve to, while moving toward the distal end, sequentially push up the staples to be released from the cartridge.

The working member 1540 may further include the blade 1544 formed on one side of the body part 1541. For example, the blade 1544 may be formed at the distal end of the body part 1541. The blade 1544 may be formed to be sharp to cut tissue.

That is, at least a portion of the blade 1544 may be released from the first jaw 1101 and the cartridge, to cut tissue arranged between the first jaw 1101 and the second jaw 1102.

As another example, the blade 1544 may always be released from the first jaw 1101. As another example, the blade 1544 may be normally accommodated in the first jaw 1101 or the cartridge, and only when the working member 1540 moves in the lengthwise direction, may be released from the first jaw 1101.

The end tool 1100 may include the clutch assembly 1570.

The clutch assembly 1570 may be provided on the working member 1540.

The clutch assembly 1570 may be formed with the working member 1540 as one body or may be provided as a separate member, and some components constituting the clutch assembly 1570 may be formed with the working member 1540 as one body and the other components may be configured as separate members.

The clutch assembly 1570 may allow or block transmission of power for moving the working member 1540, from the moving member 1550 to the working member 1540. For example, when the moving member 1550 moves toward the distal ends of the jaws 1103, the clutch assembly 1570 may be connected to the moving member 1550 to enable movement of the working member 1540. In addition, when the moving member 1550 moves toward the proximal ends of the jaws 1103, the clutch assembly 1570 may be disconnected from the moving member 1550 such that the working member 1540 and the moving member 1550 may move independently of each other. In other words, when the working member 1540 is engaged with the moving member 1550, the working member 1540 may move together by the movement of the moving member 1550. On the contrary, when the working member 1540 is disengaged from the moving member 1550, the working member 1540 may remain stationary or move independently regardless of the movement of the moving member 1550.

The working member 1540 may include a clutch room 1546 formed inward from one surface of the body part 1541. For example, the clutch room 1546 may refer to a space formed inward from the body part 1541. As a specific example, the clutch room 1546 may be formed on the lower side of the body part 1541. That is, the clutch room 1546 may refer to a space provided between the lower side of the body part 1541 and the upper surface of the second flange 1543. However, the present disclosure is not limited thereto, and the clutch room 1546 may be formed at a different location depending on where the moving member 1550 is arranged, as will be described below.

The clutch assembly 1570 may be arranged in the clutch room 1546. This is for preventing a movement by the moving member 1550 from interfering with a stapling motion or a cutting motion of the working member 1540, because the moving member 1550 is arranged on both side surfaces of the clutch assembly 1570, as will be described below. In addition, this is for ensuring that fastening of the working member 1540 and the moving member 1550 is performed inside the first jaw 1101, such that the fastening of the working member 1540 and the moving member 1550 is not disturbed by external factors.

The clutch assembly 1570 will be described in detail below.

In an embodiment, the end tool 1100 may further include a stopper 1560. The stopper 1560 may set a movement limit of the working member 1540. In other words, the working member 1540 may be arranged on a path toward the distal ends of the jaws 1103, and when the working member 1540 moves by a certain distance or more, the working member 1540 is blocked by the stopper 1560 and thus no longer move forward.

According to an embodiment of the present disclosure, when the moving member 1550 moves (forward) toward the distal ends of the jaws 1103, the working member 1540 moves together with the moving member 1550. In addition, when the moving member 1550 moves (backward) toward the proximal ends of the jaws 1103, the working member 1540 remains stationary. In addition, when the working member 1540 moves (backward) toward the proximal ends of the jaws 1103, the moving member 1550 remains stationary.

This correlation between motions is implemented by the clutch assembly 1570 according to the present disclosure.

FIGS. 31 to 36 are diagrams for describing a motion of the clutch assembly 1570 of FIG. 28. Hereinafter, a motion of the clutch assembly 1570 will be described with reference to FIGS. 31 to 36.

Figure 31:
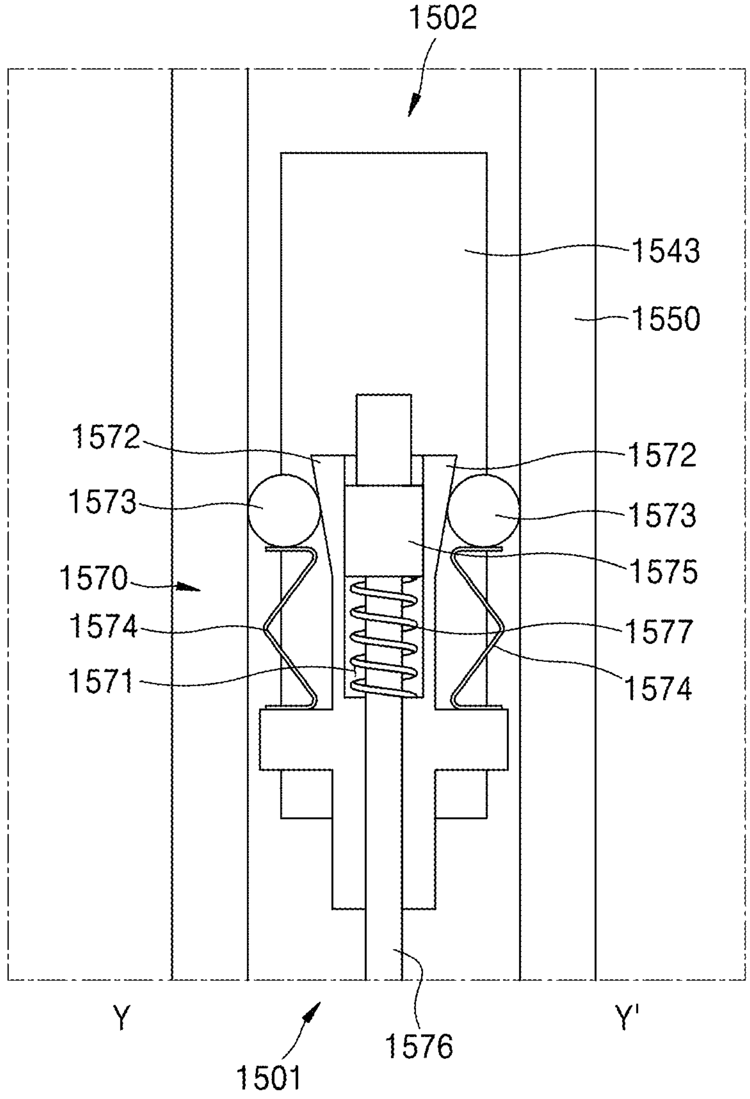
FIGS. 31 to 36 are diagrams for describing a motion of a clutch assembly of FIG. 28.

FIG. 31 is a diagram illustrating a neutral state in which no force is applied to the working member 1540 and the moving member 1550.

Referring to FIG. 31, the clutch assembly 1570 may include an inclined portion 1572 that is at least partially inclined so as to have a shape that is spaced apart from the center of the clutch assembly 1570 toward the distal ends of the jaws 1103. In other words, in FIG. 31, at least a portion of the inclined portion 1572 may be formed in a shape that widens left and right from bottom to top with respect to the vertical axis. In other words, in FIG. 31, at least a portion of the inclined portion 1572 may be formed to be inclined such that the space between the moving member 1550 and the clutch assembly 1570 narrows upward.

The clutch assembly 1570 may include a clutch member 1573 formed to be in contact with the moving member 1550. The clutch member 1573 may be arranged between the moving member 1550 and the inclined portion 1572. The clutch member 1573 is a member provided not to be fixed to a particular position, and may move between the inclined portion 1572 and the moving member 1550 as the moving member 1550 moves.

In an alternative embodiment, the clutch member 1573 may be formed into a shape having a circular cross-section. For example, the clutch member 1573 may be formed in a cylindrical shape.

In an embodiment, the clutch assembly 1570 may further include a first elastic member 1574. The first elastic member 1574 may be arranged adjacent to the clutch member 1573 so as to be in contact with the clutch member 1573.

In detail, the clutch assembly 1570 may include a portion that protrudes toward the moving member. The first elastic member 1574 may be arranged such that one side thereof is fixed to the protruding portion and the other side faces the clutch member 1573. Thus, the first elastic member 1574 may apply a force to the clutch member 1573 in a direction corresponding to the movement direction of the working member 1540.

Accordingly, the clutch member 1573 may be in contact with the moving member 1550 and the inclined surface even in a neutral state.

The clutch assembly 1570 may further include an internal space 1571 between the inclined portions 1572. The internal space 1571 may be formed in a direction corresponding to the movement direction of the working member 1540. In other words, the clutch assembly 1570 may be provided with the internal space 1571 that is penetrated in a direction corresponding to the movement direction of the working member 1540, and the internal space 1571 may be defined by the inclined portion 1572.

The clutch assembly 1570 may further include a backward block 1575 arranged in the internal space 1571.

The backward wire 1576 that transmits power for moving the working member 1540 toward the proximal ends of the jaws 1103 may be connected to the backward block 1575. That is, the user may pull the backward block 1575 backward by manipulating the manipulation part to pull the backward wire 1576, and accordingly, the working member 1540 may move backward.

The clutch assembly 1570 may further include a second elastic member 1577 connected to the backward block 1575. For example, the second elastic member 1577 may be arranged on the side of the proximal end of the backward block 1575.

The second elastic member 1577 may apply a force to the backward block 1575 in a direction corresponding to the movement direction of the working member 1540.

As described above, the clutch assembly 1570 may determine whether to engage the moving member 1550 with the working member 1540. Hereinafter, three types of driving of the clutch assembly 1570 will be described.

(When Moving Member 1550 Moves Forward)

Figure 32:
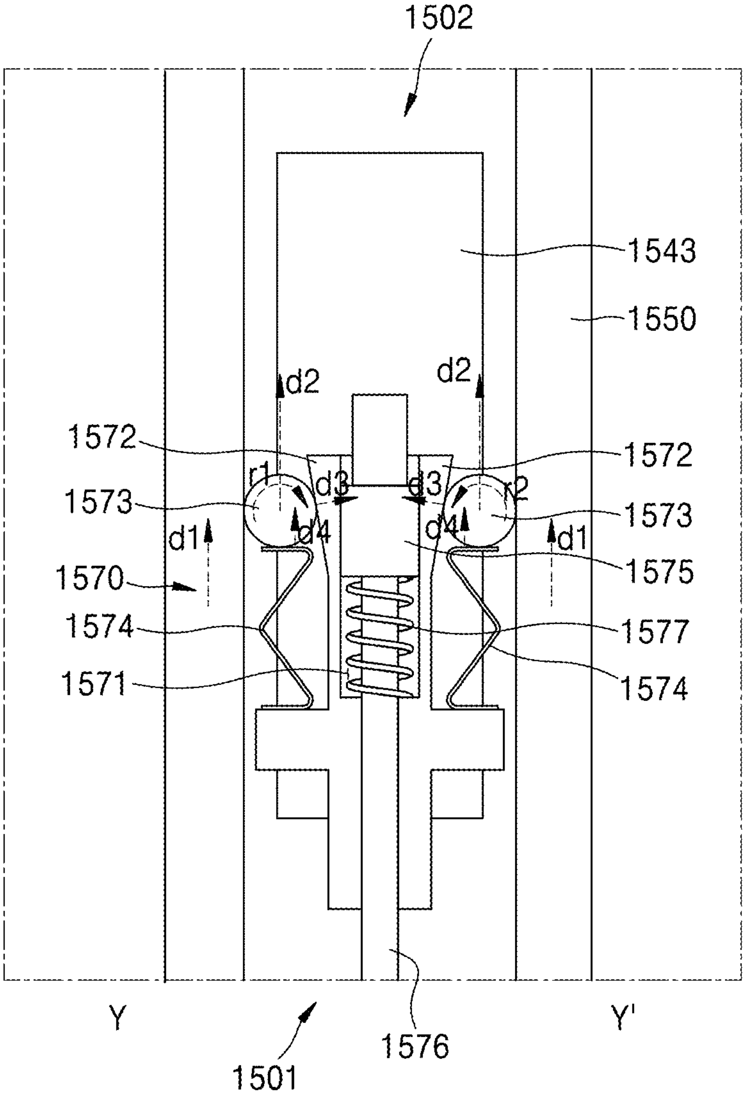

FIG. 32 is a diagram for describing driving of the clutch assembly 1570 when the moving member 1550 moves forward.

Referring to FIG. 32, when the moving member 1550 moves in a direction d1 toward the distal ends of the jaws 1103, the clutch member 1573 moves in the same direction d2 together with the moving member 1550. For example, in FIG. 32, when the moving member 1550 moves in the direction d1 toward the distal end, the clutch member 1573 arranged on the left may rotate in a clockwise direction r1 and simultaneously move in the same direction d2 as the moving member 1550, and the clutch member 1573 arranged on the right may rotate in a counterclockwise direction r2 and simultaneously move in the same direction d2 as the moving member 1550. Alternatively, the clutch member 1573 may move together with the moving member 1550 in the same direction d2 as the moving member 1550, without rotating. That is, when the moving member 1550 moves in the direction d1 toward the distal ends of the jaws 1103, the clutch member 1573 moves in the same direction d2 as the moving member 1550, while rotating or not rotating. At this time, when the clutch member 1573 moves in the direction d2 toward the distal end, the gap between the moving member 1550 and the inclined portion 1572 gradually decreases, and thus, the clutch member 1573 applies a force to the inclined portion 1572 in a certain direction d3, and the inclined portion 1572 applies a reaction force to the clutch member 1573, such that the clutch member 1573 comes into contact with the moving member 1550 and the inclined portion 1572. In other words, as the clutch member 1573 moves in the direction d2 toward the distal end, the clutch member 1573 may come into contact with the moving member 1550 and the inclined portion 1572 and apply friction or stress to the contact portion to an extent in which the movement of the working member 1540 may be restricted. Here, this contact state may be regarded as a state in which the moving member 1550 and the working member 1540 are engaged with each other.

Thus, when the moving member 1550 moves in the direction d1 toward the distal end, the moving member 1550 and the working member 1540 may be engaged with each other and move together.

In addition, even in this case, the first elastic member 1574 may continuously apply a force to the clutch member 1573 in a direction d4 toward the distal end.

(When Moving Member 1550 Moves Backward)

Figure 33:
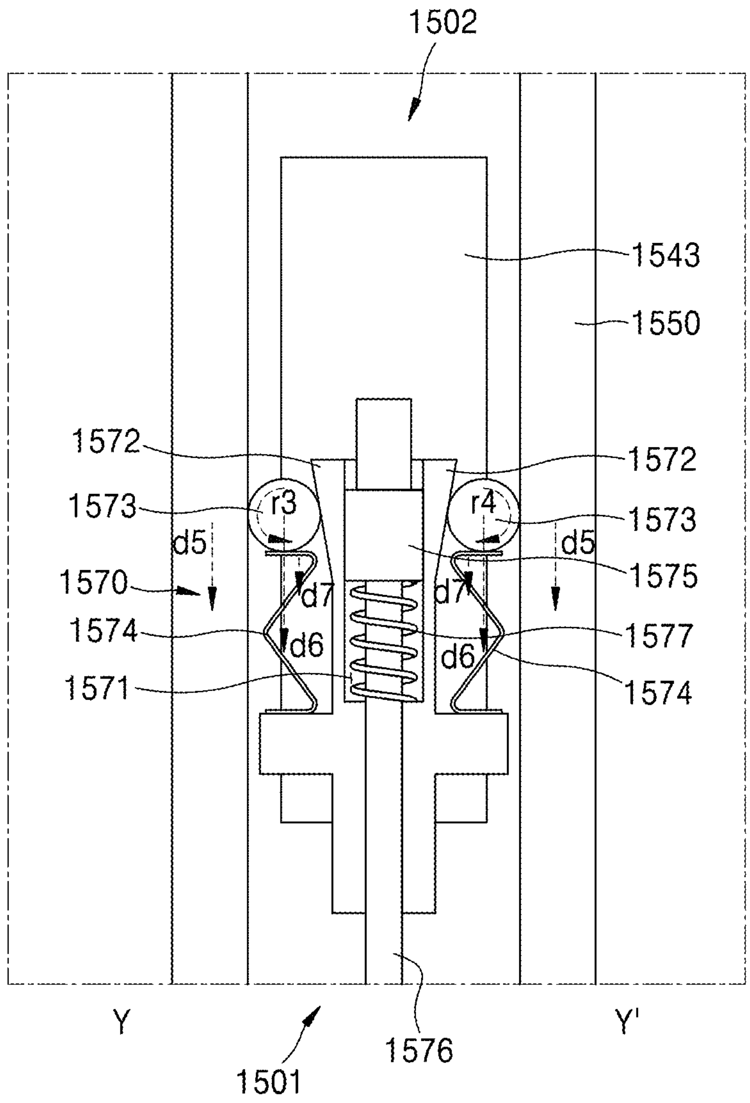
Figure 34:
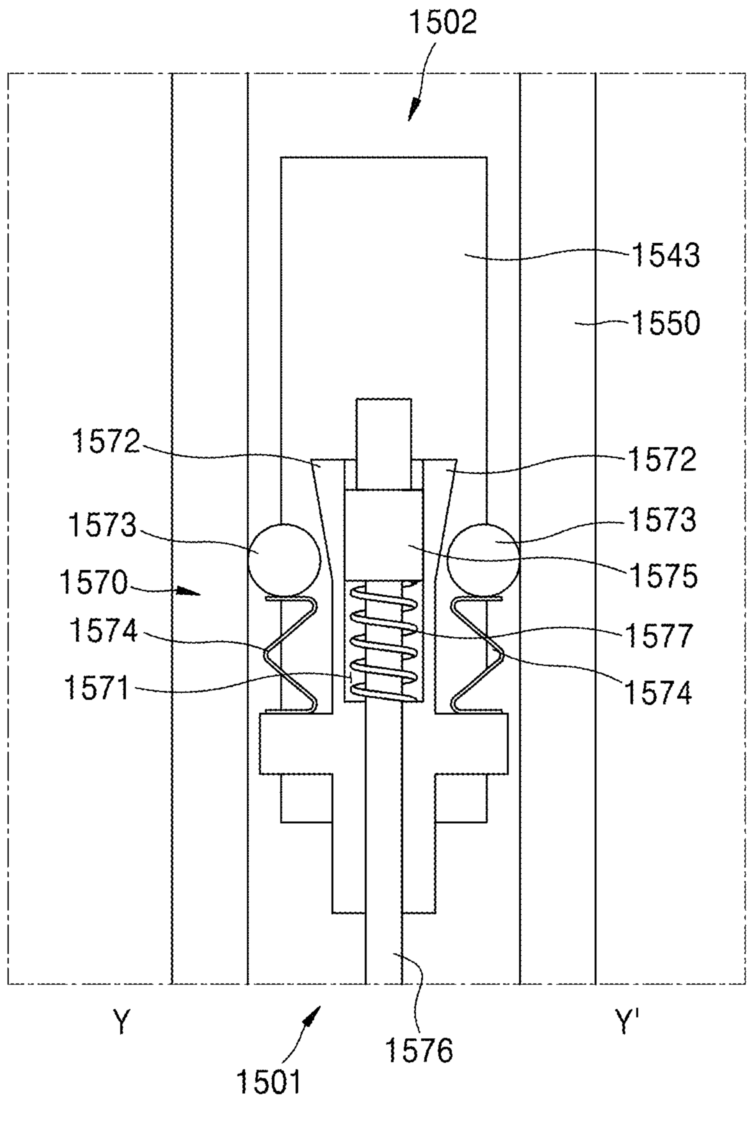

FIG. 33 is a diagram for describing driving of the clutch assembly 1570 when the moving member 1550 moves backward, and FIG. 34 is a diagram schematically illustrating a change in the configuration of the clutch assembly 1570 when the moving member 1550 moves backward.

Referring to FIGS. 33 and 34, when the moving member 1550 moves in a direction d5 toward the proximal ends of the jaws 1103, the clutch member 1573 moves in the same direction d6 together with the moving member 1550. For example, in FIG. 33, when the moving member 1550 moves in the direction d5 toward the proximal end, the clutch member 1573 arranged on the left may rotate in a counterclockwise direction r3 and simultaneously move in the same direction d6 as the moving member 1550, and the clutch member 1573 arranged on the right may rotate in a clockwise direction r4 and simultaneously move in the same direction d6 as the moving member 1550. Alternatively, the clutch member 1573 may move together with the moving member 1550 in the same direction d6 as the moving member 1550, without rotating. That is, when the moving member 1550 moves in the direction d5 toward the proximal ends of the jaws 1103, the clutch member 1573 moves in the same direction d6 as the moving member 1550, while rotating or not rotating. At this time, when the clutch member 1573 moves in the direction d6 toward the proximal end, the gap between the moving member 1550 and the inclined portion 1572 gradually increases, thus, the force applied by the clutch member 1573 to the inclined portion 1572 is reduced or removed, and the clutch member 1573 is free from the moving member 1550 and the inclined portion 1572. That is, when the clutch member 1573 moves in the direction d6 toward the proximal end, the gap between the moving member 1550 and the inclined portion 1572 increases such that no friction or only little friction is applied to the moving member 1550, the clutch member 1573, and the inclined portion 1572, and the clutch member 1573 is free from the moving member 1550 and the inclined portion 1572. Here, this free state may be regarded as a state in which the moving member 1550 and the working member 1540 are disengaged from each other.

Thus, when the moving member 1550 moves in the direction d5 toward the proximal end, the moving member 1550 and the working member 1540 are not engaged with each other, thus, the moving member 1550 may move with respect to the working member 1540, and the working member 1540 may remain stationary.

In addition, in this case, the clutch member 1573 applies a force to the first elastic member 1574 in a direction d7 toward the proximal end, and because the first clastic member 1574 supports the force, the clutch member 1573 does not go down any further and stays in a particular position. At this time, the clutch member 1573 may be spaced apart from the inclined portion 1572 instantaneously or for a certain period of time by the movement of the moving member 1550, and may kept in contact with the inclined portion 1572 in a state where almost no force is applied between the clutch member 1573 and the inclined portion 1572. That is, when the moving member 1550 moves toward the proximal ends of the jaws 1103, the clutch member 1573 may also move in the same direction such that the strong contact state between the clutch member 1573 and the inclined portion 1572 is released. Here, that the strong contact state is released means that the magnitude of the friction or stress acting between the clutch member 1573 and the moving member 1550, and between the clutch member 1573 and the inclined portion 1572 does not reach a level that may restrict the movement of the working member 1540.

(When Working Member 1540 Moves Backward Through Backward Wire 1576)

Figure 35:
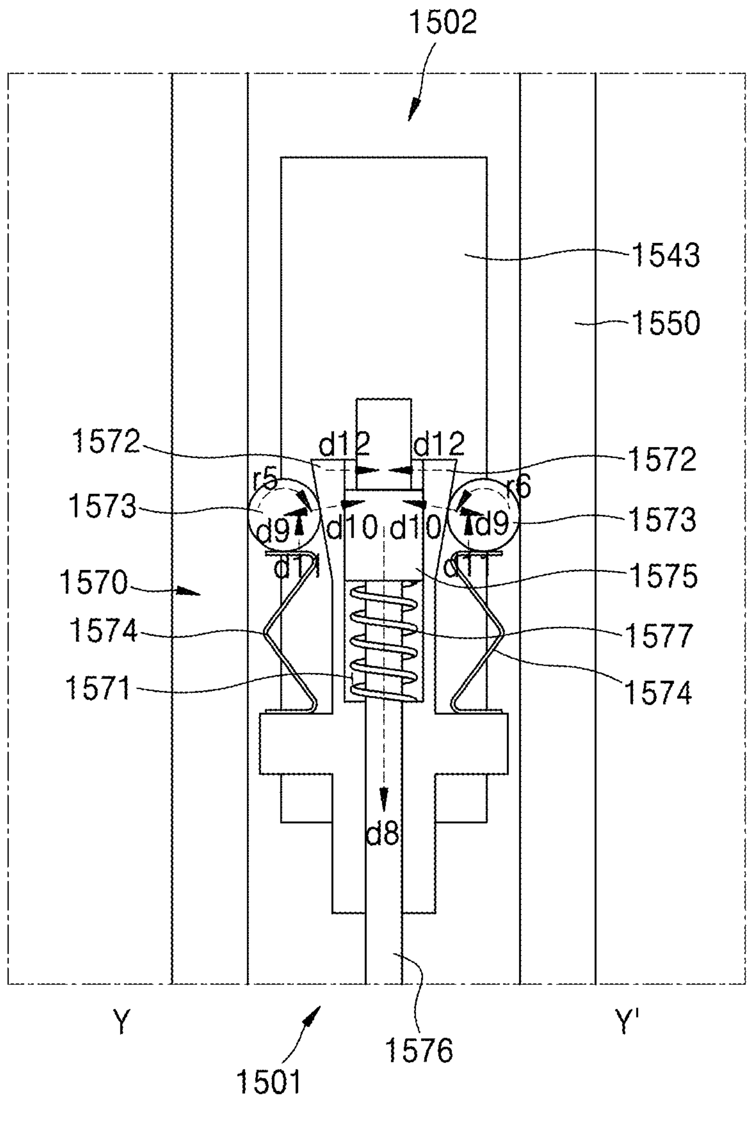
Figure 36:
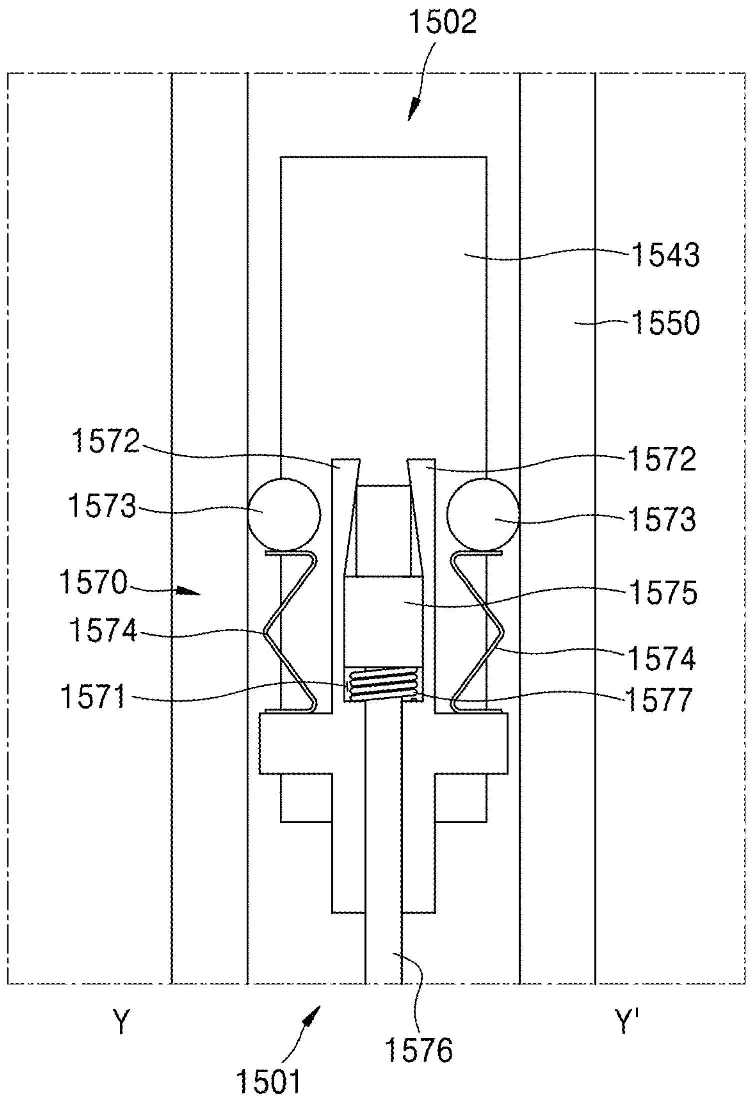

FIG. 35 is a diagram for describing driving of the clutch assembly 1570 when the backward block 1575 moves backward, and FIG. 36 is a diagram schematically illustrating a change in the configuration of the clutch assembly 1570 when the backward block 1575 moves backward.

Referring to FIGS. 35 and 36, the backward block 1575 may be arranged between the inclined portions 1572 formed on both sides of the clutch assembly 1570.

The inclined portion 1572 may be formed to change its shape or position depending on the presence or absence of an external force. For example, the inclined portion 1572 may be formed to change its shape or position such that the inclined portions 1572 on both sides approach each other, according to whether an external force is applied and/or the size of the externally applied force.

In an embodiment, the inclined portion 1572 may be formed of an elastic material. Thus, when an external force is applied to the inclined portion 1572, the shape of the inclined portion 1572 may be changed. Alternatively, when an externally applied force is removed, the shape of the inclined portion 1572 may be changed.

In other words, when the clutch member 1573 moves together with the movement of the moving member 1550 and applies a force to the inclined portion 1572, or when the clutch member 1573 continuously applies a force to the inclined portion 1572 and then the force is removed, the shape of the inclined portion 1572 may be changed. However, when the backward block 1575 is arranged between the inclined portions 1572, the backward block 1575 may prevent the shape of the inclined portion 1572 from being changed, by supporting a force that changes the shape of the inclined portion 1572.

In another embodiment, the inclined portions 1572 may be formed such that the inclined portions 1572 on both sides may move toward or away from each other. For example, when an external force is applied to the inclined portions 1572 on both sides in a direction in which they approach each other, the inclined portions 1572 on both sides may move toward each other. Alternatively, when the externally applied force is removed, the inclined portions 1572 may return to their original positions.

In other words, when no external force is applied, the inclined portion 1572 may be arranged in a neutral position. Here, the neutral position refers to an initial position where the inclined portion 1572 may be located when no external force is applied. To this end, the inclined portion 1572 may be connected to a separately provided elastic body (e.g., a spring or an elastic wire). In addition, at least a portion of the inclined portion 1572 may be hinged or may include a sliding structure, so as to be movable according to the presence or absence of an external force. However, the present disclosure is not limited thereto, and any inclined portion 1572 may be included in a modified embodiment of the present disclosure as long as it has a structure in which its position may be changed according to the presence or absence of an external force.

In this case, when the clutch member 1573 moves together with the movement of the moving member 1550 and applies a force to the inclined portion 1572, or when the clutch member 1573 continuously applies a force to the inclined portion 1572 and then the force is removed, the position of the inclined portion 1572 may be changed. For example, the inclined portion 1572 may rotate around the hinge, or slide. However, when the backward block 1575 is arranged between the inclined portions 1572, the backward block 1575 may prevent the position of the inclined portion 1572 from being changed, by supporting the force that changes the position of the inclined portion 1572 (the force that causes the inclined portions 1572 to move toward each other).

Ultimately, to express the motion of the inclined portion 1572 from another perspective, the inclined portion 1572 may be expressed as bending, rotating, moving, or pivoting inward when an external force is applied inward. Thus, hereinafter, that the inclined portions 1572 approach each other should be interpreted as meaning that the inclined portions 1572 on both sides bend, rotate, move, or pivot inward.

When the wire connected to the backward block 1575 pulls the backward block 1575, the backward block 1575 may move in a direction d8 toward the proximal ends of the jaws 1103. For example, the backward block 1575 may move along the internal space 1571 of the clutch assembly 1570 in the direction d8 toward the proximal end.

When the backward block 1575 moves in the direction d8 toward the proximal end, the backward block 1575 is no longer located between the inclined portions 1572, and thus, a force is applied to the inclined portions 1572 in a direction d12 in which the inclined portions 1572 converge inward. This force may be a force with which the clutch member 1573 pushes the inclined portion 1572, or may be an elastic force that causes the inclined portion 1572 to return to its original position.

In detail, the first elastic member 1574 continuously applies a force to the clutch member 1573 in a direction d9 toward the distal end, accordingly, the clutch member 1573 applies a force in a direction d10 in which the inclined portions 1572 come together, and the inclined portions 1572 apply a reaction force to the clutch member 1573 in the opposite direction d9. Ultimately, the clutch member 1573 arranged on the left in FIG. 35 may apply a force to the inclined portions 1572 in the rightward direction, and the clutch member 1573 arranged on the right may apply a force to the inclined portions 1572 in the leftward direction, such that the inclined portions 1572 on both sides to approach each other. At this time, the clutch member 1573 arranged on the left may apply a force to the inclined portion 1572 while rotating in a clockwise direction r5 or without rotating. Similarly, the clutch member 1573 arranged on the right may also apply a force to the inclined portion 1572 while rotating in a counterclockwise direction r6 or without rotating.

Accordingly, the inclined portions 1572 are deformed or displaced in the direction d12 in which they come together, and the close contact between the clutch member 1573 and the inclined portion 1572 is released. That is, the moving member 1550 and the working member 1540 are disengaged from each other.

Thereafter, as the backward block 1575 is continuously pulled, the backward block 1575 moves along the internal space 1571, and when the backward block 1575 reaches its limit, it moves backward together with the working member 1540. That is, in a case in which the backward block 1575 is in the internal space 1571, when the backward block 1575 reaches a backward limit point while moving along the internal space 1571, for example, when the path is blocked, the working member 1540 is moved backward together with the backward block 1575 by the force that pulls the backward block 1575.

The second elastic member 1577 may be arranged at the proximal end of the backward block 1575 to continuously apply a force to the backward block 1575. Because the second elastic member 1577 applies a force to the backward block 1575 toward the distal end, the backward wire 1576 may maintain a certain level of tension or more, thereby preventing the wire from being twisted or deviating from its path. For example, the backward wire 1576 may maintain a certain level of tension or more, thereby maintaining the path of a wire wound around a pulley involved in a pitch motion or a yaw motion of the end tool 1100.

In addition, when the working member 1540 moves to the distal ends of the jaws 1103, the backward wire 1576 also needs to move at a 1:1 ratio to correspond to the movement of the working member 1540. However, a problem may occur in which the length of the backward wire 1576 is not precisely controlled to correspond to the movement of the working member 1540. For example, a problem may occur in which the backward wire 1576 becomes instantaneously loose during the movement of the working member 1540. Thus, the second elastic member 1577 may continuously maintain a certain level of tension or more on the backward wire 1576 by continuously applying a force to the backward block 1575 toward the distal end, thereby compensating for an error in controlling the length of the backward wire 1576.

Ultimately, when the backward block 1575 moves backward, the moving member 1550 and the working member 1540 are disengaged from each other such that the working member 1540 moves with respect to the moving member 1550, and the moving member 1550 may remain stationary.

Although the present disclosure has been described with reference to the embodiment shown in the drawings, which is merely exemplary, it will be understood by those skilled in the art that various modifications and equivalent other embodiments are possible therefrom. Accordingly, the true technical protection scope of the present disclosure should be defined by the technical spirit of the appended claims.

The particular implementations shown and described herein are illustrative examples of the embodiments and are not intended to otherwise limit the scope of the embodiments in any way. For the sake of brevity, related-art electronics, control systems, software and other functional aspects of the systems may not be described in detail. Furthermore, line connections or connection members between elements depicted in the drawings represent functional connections and/or physical or circuit connections by way of example, and in actual applications, they may be replaced or embodied with various suitable additional functional connections, physical connections, or circuit connections. In addition, no item or component is essential to the practice of the disclosure unless the item or component is specifically described as being "essential" or "critical".

The use of the terms "a" and "an" and "the" and similar referents in the context of describing the present disclosure (especially in the context of the following claims) are to be construed to cover both the singular and the plural. Further, recitation of ranges of values herein are merely intended to serve as a shorthand method of referring individually to each separate value falling within the range, unless otherwise indicated herein, and each separate value is incorporated into the specification as if it were individually recited herein. Finally, operations of all methods described herein can be performed in any suitable order unless otherwise indicated herein or otherwise clearly contradicted by context. The embodiments are not limited to the described order of the operations. The use of any and all examples, or exemplary terms (e.g., "such as") provided herein, is intended merely to better illuminate the present disclosure and does not pose a limitation on the scope of the present disclosure unless otherwise claimed. Also, numerous modifications and adaptations will be readily apparent to those skilled in the art without departing from the spirit and scope of the present disclosure.

The present disclosure may provide a surgical instrument capable of controlling a movement of a working member provided in the surgical instrument, in a one-way clutch manner.

In addition, the present disclosure may provide a surgical instrument capable of simultaneously moving or relatively moving a working member and a moving member both provided in the surgical instrument.

However, the above effects are only examples, and the effects of the present disclosure are not limited thereto.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A surgical instrument comprising:

an end tool configured to rotate in at least one direction; and a manipulation part configured to control a motion of the end tool, wherein the end tool comprises:

a pair of jaws comprising a first jaw and a second jaw;

a working member configured to move in a lengthwise direction of the pair of jaws;

a moving member formed to extend to have a length corresponding to a movement direction of the working member, and configured to transmit, to the working member, power for moving the working member, while linearly moving in a lengthwise direction; and a clutch assembly arranged in the working member and configured to allow or block transmission of power from the moving member to the working member.

2. The surgical instrument of claim 1, wherein the second jaw is rotatable with respect to the first jaw.

3. The surgical instrument of claim 2, wherein the working member is further configured to apply a force while moving in a direction from proximal ends of the pair of jaws toward distal ends of the pair of jaws, such that the first jaw and the second jaw perform a clamping motion.

4. The surgical instrument of claim 1, wherein the working member comprises:

a body part;

a first flange arranged on one side of the body part and formed to have a width greater than a width of the body part; and a second flange arranged on another side of the body part and formed to have a width greater than the width of the body part.

5. The surgical instrument of claim 4, wherein the first jaw comprises a first slit extending in the lengthwise direction of the first jaw, and the working member is further configured to move while at least a portion of the body part is accommodated in the first slit.

6. The surgical instrument of claim 5, wherein, in the working member, the second flange is arranged at a lower portion of the first jaw, the body part is arranged to pass through the first slit from the first jaw, and at least a portion of the second flange comes into contact with the first jaw when the working member moves in the lengthwise direction of the pair of jaws.

7. The surgical instrument of claim 4, wherein the second jaw comprises a second slit extending in the lengthwise direction of the second jaw, and the working member is further configured to move while at least a portion of the body part is accommodated in the second slit.

8. The surgical instrument of claim 7, wherein, in the working member, the first flange is arranged at an upper portion of the second jaw, the body part is arranged to pass through the second slit from the second jaw, and at least a portion of the first flange comes into contact with the second jaw when the working member moves in the lengthwise direction of the pair of jaws.

9. The surgical instrument of claim 4, wherein the working member further comprises a clutch room formed from one surface of the body part toward an inside of the body part, and the clutch assembly is arranged in the clutch room.

10. The surgical instrument of claim 1, wherein the clutch assembly comprises a clutch member formed to come into contact with the moving member, and when the moving member moves toward distal ends of the pair of jaws, the clutch member and the moving member come into close contact with each other such that the moving member and the working member move together.

11. The surgical instrument of claim 10, wherein, in the clutch assembly, when the moving member moves toward proximal ends of the pair of jaws, the close contact between the clutch member and the moving member is released such that the moving member moves with respect to the working member.

12. The surgical instrument of claim 10, wherein the clutch assembly further comprises inclined portions that are formed to be inclined at least in part to have a shape that is farther from center of the clutch assembly toward the distal ends of the pair of jaws, and are formed to come into contact with the clutch member as the moving member moves.

13. The surgical instrument of claim 12, wherein, in the clutch assembly, when the moving member moves toward the distal ends of the pair of jaws, the clutch member also moves in the same direction to come into contact with the inclined portions, and when the moving member moves toward proximal ends of the pair of jaws, the clutch member also moves in the same direction such that a contact state between the clutch member and the inclined portions is released.

14. The surgical instrument of claim 12, wherein the clutch assembly further comprises a first elastic member configured to apply a force to the clutch member in a direction corresponding to the movement direction of the working member.

15. The surgical instrument of claim 12, wherein the clutch assembly further comprises a backward wire configured to transmit power for moving the working member toward proximal ends of the pair of jaws, and the inclined portions are formed to be deformed or moved at least in part based on a movement direction of the backward wire.

16. The surgical instrument of claim 12, wherein the clutch assembly further comprises:

an internal space arranged between the inclined portions in a direction corresponding to the movement direction of the working member;

a backward block arranged in the internal space; and a backward wire connected to the backward block to transmit power for moving the working member toward proximal ends of the pair of jaws.

17. The surgical instrument of claim 16, wherein the backward block is arranged between the inclined portions to prevent at least portions of the inclined portions from being deformed or moved toward each other by a force applied to the inclined portions.

18. The surgical instrument of claim 17, wherein, when the backward block moves along the internal space toward the proximal ends of the pair of jaws, the at least portions of the inclined portions are deformed or moved toward each other.

19. The surgical instrument of claim 16, wherein the clutch assembly further comprises a second elastic member arranged on a side of a proximal end of the backward block.

20. The surgical instrument of claim 16, wherein, when the backward block moves toward the proximal ends of the pair of jaws, the working member moves with respect to the moving member.

21. The surgical instrument of claim 10, wherein the clutch member has a circular cross-section.

* * * * *